United States Patent
Lim

(10) Patent No.: US 12,230,364 B2
(45) Date of Patent: *Feb. 18, 2025

(54) IMMUNOTHERAPY METHODS FOR PATIENTS WHOSE TUMORS CARRY A HIGH PASSENGER GENE MUTATION BURDEN

(71) Applicant: Regeneron Pharmaceuticals, Inc., Tarrytown, NY (US)

(72) Inventor: Wei Keat Lim, Tarrytown, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 39 days.

This patent is subject to a terminal disclaimer.

(21) Appl. No.: 18/186,762

(22) Filed: Mar. 20, 2023

(65) Prior Publication Data

US 2023/0268028 A1    Aug. 24, 2023

Related U.S. Application Data

(63) Continuation of application No. 16/135,913, filed on Sep. 19, 2018, now Pat. No. 11,640,848.

(60) Provisional application No. 62/560,955, filed on Sep. 20, 2017.

(51) Int. Cl.
| | | |
|---|---|---|
| G16B 30/00 | (2019.01) | |
| A61P 35/00 | (2006.01) | |
| C12Q 1/6806 | (2018.01) | |
| C12Q 1/6809 | (2018.01) | |
| C12Q 1/6886 | (2018.01) | |
| G16B 5/00 | (2019.01) | |
| G16B 15/00 | (2019.01) | |

(52) U.S. Cl.
CPC .............. *G16B 30/00* (2019.02); *A61P 35/00* (2018.01); *C12Q 1/6806* (2013.01); *C12Q 1/6809* (2013.01); *C12Q 1/6886* (2013.01); *G16B 5/00* (2019.02); *G16B 15/00* (2019.02); *C12Q 2565/519* (2013.01); *C12Q 2600/106* (2013.01); *C12Q 2600/156* (2013.01); *C12Q 2600/158* (2013.01)

(58) Field of Classification Search
CPC ....................................................... G16B 30/00
USPC ..................................................... 424/155.1
See application file for complete search history.

(56) References Cited

U.S. PATENT DOCUMENTS

| | | | |
|---|---|---|---|
| 4,863,849 A | 9/1989 | Melamede | |
| 4,971,903 A | 11/1990 | Hyman | |
| 5,302,509 A | 4/1994 | Cheeseman | |
| 5,599,675 A | 2/1997 | Brenner | |
| 5,750,341 A | 5/1998 | Macevicz | |
| 5,763,594 A | 5/1998 | Hiatt et al. | |
| 5,798,210 A | 8/1998 | Canard et al. | |
| 5,939,292 A | 8/1999 | Gelfand et al. | |
| 6,001,566 A | 12/1999 | Canard et al. | |
| 6,090,549 A | 7/2000 | Mirzabekov et al. | |
| 6,210,891 B1 | 4/2001 | Nyren et al. | |
| 6,258,568 B1 | 7/2001 | Nyren | |
| 6,401,267 B1 | 6/2002 | Drmanac | |
| 6,620,584 B1 | 9/2003 | Chee et al. | |
| 6,664,079 B2 | 12/2003 | Ju et al. | |
| 6,984,720 B1 | 1/2006 | Korman et al. | |
| 7,034,121 B2 | 4/2006 | Carreno et al. | |
| 7,057,026 B2 | 6/2006 | Barnes et al. | |
| 7,605,238 B2 | 10/2009 | Korman et al. | |
| 11,640,848 B2* | 5/2023 | Lim .................. C12Q 1/6809 702/19 |
| 2005/0037398 A1 | 2/2005 | Gelfand et al. | |
| 2005/0130173 A1 | 6/2005 | Leamon et al. | |
| 2006/0134633 A1 | 6/2006 | Chen et al. | |
| 2009/0088327 A1 | 4/2009 | Rigatti et al. | |
| 2009/0325172 A1 | 12/2009 | Milton et al. | |
| 2010/0028885 A1 | 2/2010 | Balasubramanian et al. | |
| 2015/0203580 A1 | 7/2015 | Papadopoulos et al. | |
| 2017/0022273 A1* | 1/2017 | Zhou ................. C07K 16/3023 |
| 2017/0101472 A1 | 4/2017 | Ullman et al. | |
| 2017/0174779 A1 | 6/2017 | Varghese et al. | |

FOREIGN PATENT DOCUMENTS

| | | |
|---|---|---|
| CN | 105777906 | 7/2016 |
| CN | 106977602 | 7/2017 |
| JP | 2017507650 | 3/2017 |
| WO | 01/23411 | 4/2001 |
| WO | 05/024010 | 3/2005 |

(Continued)

OTHER PUBLICATIONS

Mishra et al (Oncotarget, 2016, 7(49): 81341-81356).*
Berrien-Elliott et al (Cancer Research, 2013, 73(2): 605-616).*
Office Action was mailed on Jun. 24, 2021 by the KR Patent Office for KR Application No. 10-2020-7018681, filed on Jun. 29, 2020 (Applicant—Regeneron Pharmaceuticals, Inc.).
Office Action was mailed on Feb. 23, 2022 by the KR Patent Office for KR Application No. 10-2020-7018681, filed on Jun. 29, 2020 (Applicant—Regeneron Pharmaceuticals, Inc.).
Office Action was mailed on Jun. 17, 2022 by the UA Patent Office for UA Application No. 202002442, filed on Sep. 19, 2018 (Applicant—Regeneron Pharmaceuticals, Inc.) (3 pages).

(Continued)

*Primary Examiner* — Sean E Aeder
(74) *Attorney, Agent, or Firm* — Armstrong Teasdale LLP

(57) ABSTRACT

Methods for selecting a cancer patient for immunotherapy comprise establishing a total passenger gene mutation burden from a tumor of a cancer patient, generating a background distribution for the mutational burden of the tumor, normalizing the total passenger gene mutation burden against the background distribution, and categorizing the cancer patient as an immunotherapy responder when the total passenger gene mutation burden is greater than the mean of the background distribution. When the cancer patient is an immunotherapy responder, the patient may be administered an immunotherapy regimen that comprises activation/inhibition of T cell receptors that promote T cell activation and/or prolong immune cytolytic activities.

45 Claims, 16 Drawing Sheets

Specification includes a Sequence Listing.

(56) References Cited

FOREIGN PATENT DOCUMENTS

| WO | 2015103037 | 7/2015 |
|---|---|---|
| WO | 2017062888 | 4/2017 |
| WO | 2017112775 | 6/2017 |
| WO | 2017151517 | 9/2017 |
| WO | 2017151524 | 9/2017 |
| WO | 2018068028 | 4/2018 |

OTHER PUBLICATIONS

Spencer et al., "Biomarkers for immunotherapy: current developments and challenges", Am Soc Clin Educ Book, May 2016, 35, pp. e493-e503.
Beasley et al., "Immune Checkpoint Inhibitor Therapy as a Novel and Effective Therapy for Aggressive Cutaneous Squamous-cell Carcinoma", Clinical Skin Cancer, 2016, 1(2), pp. 75-81.
Postow et al., "Immune Checkpoint Blockade in Cancer Therapy", J of Clinical Oncology, 2015, 33(17), pp. 1974-1982.
Sharma et al., "The future of immune checkpoint therapy", Science, 2015, 348(6230), pp. 56-61.
Migden, "PD-1 Blockade with Cemiplimab in Advanced Cutaneous Squamous-Cell Carcinoma", The New England Journal of Medicine, 2018, pp. 341-351.
Office Action was mailed on Mar. 21, 2022 by the CA Patent Office for CA Application No. 3,075,927, filed on Sep. 19, 2018 (Applicant—Regeneron Pharmaceuticals, Inc.) (6 pages).
Notification of Reasons for Rejection were mailed on Jul. 20, 2021 by the JP Patent Office for JP Application No. 2020-516633, filed on Sep. 19, 2019 (Applicant—Regeneron Pharmaceuticals, Inc.) (4 pages).
Nakatsura, "Era of cancer immunotherapy has come", Japanese J of Clinical Immunology, 2016, 39(3), pp. 164-171 (abstract).
Topalian et al., "Mechanism-driven biomarkers to guide immune checkpoint blockade in cancer therapy", Nature Reviews Cancer, 2016, 16, pp. 275-287.
Topalian et al., "Immunotherapy: The path to win the war on cancer?", Cell, 2015, 16(2), pp. 185-186.
Written Opinion and Search Report were mailed on Nov. 29, 2021 by the SG Patent Office for SG Application No. 11202002282, filed on Sep. 19, 2018 (Applicant—Regeneron Pharmaceuticals, Inc.) (6 pages of Written Opinion; 3 pages of Search Report).
Decision of Refusal was mailed on Nov. 15, 2021 by the RU Patent Office for RU Application No. 2020113600, filed on Sep. 19, 2018 (Applicant—Regeneron Pharmaceuticals, Inc.) (7 pages of Translation).
Examination Report was mailed on Nov. 10, 2021 by the AU Patent Office for AU Application No. 2018336785, filed on Sep. 19, 2018 (Applicant—Regeneron Pharmaceuticals, Inc.) (3 pages).
Examination Report was mailed on Jul. 7, 2021 by the AU Patent Office for AU Application No. 2018336785, filed on Sep. 19, 2018 (Applicant—Regeneron Pharmaceuticals, Inc.) (5 pages).
Office Action was mailed on Apr. 7, 2021 by the CA Patent Office for CA Application No. 3,075,927, filed on Sep. 19, 2018 (Applicant—Regeneron Pharmaceuticals, Inc.) (5 pages).
Office Action was mailed on Jan. 3, 2022 by the CA Patent Office for CA Application No. 3,075,927, filed on Sep. 19, 2018 (Applicant—Regeneron Pharmaceuticals, Inc.) (4 pages).
Topalian et al., "Mechanism-driven biomarkers to guide immune checkpoint blockade in cancer therapy", Nature Reviews Cancer, 2016, 16(5), pp. 275-287.
Campesato et al., "Comprehensive cancer-gene panels can be used to estimate mutational load and predict clinical benefit to PD-1 blockade in clinical practice", Oncotarget, 2015. Retrieved from the Internet: URL: https://www.ncbi.lm.nih.gov/pmc.articles/PMC4741447/pdf/oncotarget-06-34221.pdf.
Li et al., "Mining the coding and non-coding genome for cancer drivers", Cancer Letters, 2015, 369(2), pp. 307-315.
Mcfarland et al., "The Damaging Effect of Passenger Mutations on Cancer Progression", Cancer Res, 2017, 77 (18), pp. 4763-4772.
Charoentong et al., "Pan-cancer Immunogenomic Analyses Reveal Genotype-Immunophenotype Relationships and Predictors of Response to Checkpoint Blockade", Cell Reports, 2017, 18(1), pp. 248-262.
International Search Report and Written Opinion were mailed on Dec. 19, 2018 by the International Searching Authority for International Application No. PCT/US2018/051755, filed on Sep. 19, 2019 (Applicant—Regeneron Pharmaceuticals, Inc.) (15 pages).
Altschul et al., "Issues in searching molecular sequence databases", Nature Genet, 1994, 6(2), pp. 119-129.
Corpet et al., "Multiple sequence alignment with hierarchical clustering", Nucl Acids Res, 1988, 16, pp. 10881-10890.
Dressman et al., "Transforming single DNA molecules into fluorescent magnetic particles for detection and enumeration of genetic variations", Proc Natl Acad Sci, 2003, 100, pp. 8817-8822.
Higgins et al., "Fast and sensitive multiple sequence alignments on a microcomputer", CABIOS, 1989, 5, pp. 151-153.
Huang et al., "Parallelization of a local Similarity Search Algorithm", Comput Appl Biosci, 1992, 8(2), pp. 155-165.
Mitra et al., "Digital genotyping and haplotyping with polymerase colonies", Proc Natl Acad Sci, 2003, 100(10), pp. 5926-5931.
Pearson et al., "Improved tools for biological sequence comparison", Proc Natl Acad Sci, 1988, 85(8), pp. 2444-2448.
Ronaghi et al., "A sequencing method based on real-time pyrophosphate", Science, 1998, 281, pp. 363.
Shendure et al., "Accurate multiplex polony sequencing of an evolved bacterial genome", Science, 2005, 309(5741), pp. 1728-1732.
Smith et al., "Comparison of biosequences", Advances in Applied Mathematics, 1981, 2(4), pp. 482-489.
Stratton et al., "The cancer genome", Nature, 2009, 458(7239), pp. 719-724.
Rizvi et al., "Mutational landscape determines sensitivity to PD-1 blockade in non-small cell lung cancer", Science, 2015, 348(6230), pp. 124-128.
Yarchoan et al., "Targeting neoantigens to augment antitumour immunity", Nat Rev Cancer, 2017, 17(4), pp. 209-222.

* cited by examiner

FIG. 8

| Gene | PGI | Type | Perc |
|---|---|---|---|
| KDR | 0.94 | skcm | 0.14 |
| PDE4DIP | 0.89 | skcm | 0.15 |
| PDGFRA | 0.88 | skcm | 0.10 |
| TFEB | 0.87 | skcm | 0.03 |
| PBX1 | 0.87 | skcm | 0.04 |
| CRLF2 | 0.86 | skcm | 0.03 |
| RANBP17 | 0.86 | skcm | 0.06 |
| COL1A1 | 0.86 | skcm | 0.12 |
| MLL3 | 0.85 | blca | 0.22 |
| ROS1 | 0.85 | skcm | 0.18 |
| ARID2 | 0.85 | skcm | 0.13 |
| KIAA1549 | 0.84 | skcm | 0.10 |
| PRDM16 | 0.84 | skcm | 0.08 |
| HIP1 | 0.84 | skcm | 0.04 |
| USP6 | 0.83 | skcm | 0.09 |
| NTRK3 | 0.83 | luad | 0.08 |
| SRGAP3 | 0.83 | skcm | 0.10 |
| IL7R | 0.83 | skcm | 0.11 |
| PDGFRB | 0.83 | skcm | 0.06 |
| ZNF331 | 0.83 | skcm | 0.06 |
| POT1 | 0.83 | luad | 0.03 |
| CREB3L2 | 0.82 | skcm | 0.03 |
| PAX7 | 0.81 | stad | 0.03 |
| SLC34A2 | 0.81 | skcm | 0.06 |
| PRDM1 | 0.81 | skcm | 0.06 |
| STL | 0.81 | skcm | 0.04 |
| C15orf55 | 0.81 | skcm | 0.09 |
| BCL11A | 0.81 | skcm | 0.10 |
| LCK | 0.81 | skcm | 0.04 |
| CHN1 | 0.80 | skcm | 0.02 |

| Gene | PGI | Type | Perc |
|---|---|---|---|
| CREB1 | 0.17 | ucec | 0.02 |
| CCND1 | 0.16 | ucec | 0.07 |
| NF2 | 0.16 | * | 0.06 |
| CBFB | 0.16 | brca | 0.02 |
| TCF7L2 | 0.16 | * | 0.08 |
| RPL22 | 0.16 | ucec | 0.13 |
| YWHAE | 0.13 | * | 0.04 |
| APC | 0.12 | * | 0.71 |
| PIK3CA | 0.12 | ucec | 0.54 |
| CIC | 0.11 | * | 0.18 |
| SMARCB1 | 0.10 | stad | 0.04 |
| AKT1 | 0.09 | ucec | 0.03 |
| PBRM1 | 0.09 | * | 0.33 |
| PTEN | 0.05 | * | 0.69 |
| MAX | 0.04 | ucec | 0.05 |
| FLT3 | 0.03 | * | 0.30 |
| PHF6 | 0.02 | ucec | 0.04 |
| NACA | 0.02 | ucec | 0.07 |
| ATRX | 0.01 | * | 0.44 |
| FAM22B | 0.00 | * | 0.02 |
| PIK3R1 | 0.00 | ucec | 0.38 |
| U2AF1 | -0.03 | laml | 0.04 |
| DNMT3A | -0.08 | * | 0.23 |
| VHL | -0.08 | * | 0.48 |
| FIP1L1 | -0.10 | ucec | 0.04 |
| IDH1 | -0.17 | * | 0.76 |
| RUNX1 | -0.17 | * | 0.10 |
| CEBPA | -0.19 | * | 0.07 |
| NPM1 | -0.24 | * | 0.26 |
| IDH2 | -0.28 | laml | 0.10 |

FIG. 12

| # | Gene | # | Gene | # | Gene | # | Gene |
|---|---|---|---|---|---|---|---|
| 1 | MUC16 | 43 | CRB1 | 85 | LAMA2 | 127 | PKP2 |
| 2 | PKHD1L1 | 44 | CNTN5 | 86 | HS3ST4 | 128 | DYSF |
| 3 | PAPPA2 | 45 | ADAMTS20 | 87 | GH1 | 129 | SLC8A1 |
| 4 | CTNND2 | 46 | OR4M1 | 88 | RBP3 | 130 | STON1-GTF2A1L |
| 5 | NEB | 47 | LILRA2 | 89 | SMR3A | 131 | OR5D13 |
| 6 | TRPV5 | 48 | CNTNAP2 | 90 | OR4M2 | 132 | CNTNAP4 |
| 7 | FLG2 | 49 | TNN | 91 | SCN1A | 133 | MAGEA6 |
| 8 | FLG | 50 | LRFN2 | 92 | GRID2 | 134 | OR51A4 |
| 9 | C1orf173 | 51 | GABRG1 | 93 | CFHR4 | 135 | KIAA1210 |
| 10 | MUC17 | 52 | GPR98 | 94 | DMBT1 | 136 | NBPF1 |
| 11 | XIRP2 | 53 | UNC13A | 95 | CSMD1 | 137 | NDST4 |
| 12 | TTN | 54 | DNAH7 | 96 | COL11A2 | 138 | PRIM2 |
| 13 | KRTAP12-3 | 55 | COL6A6 | 97 | RPS4Y2 | 139 | COL11A1 |
| 14 | RNASE3 | 56 | NLRP8 | 98 | PCLO | 140 | DNAH9 |
| 15 | OR2G2 | 57 | LTBP1 | 99 | BCLAF1 | 141 | MAGEC1 |
| 16 | MYH2 | 58 | PRB1 | 100 | ZNF831 | 142 | PLXNA4 |
| 17 | SLC4A10 | 59 | ADCYAP1R1 | 101 | CRISP3 | 143 | C2CD3 |
| 18 | CDH18 | 60 | RELN | 102 | RGS5 | 144 | CALCR |
| 19 | OR4A47 | 61 | OR10S1 | 103 | EPHA7 | 145 | SLCO1B1 |
| 20 | OR10R2 | 62 | ACAN | 104 | OR52B4 | 146 | OR8H1 |
| 21 | TPTE | 63 | NLRP7 | 105 | VWA3B | 147 | ITGAD |
| 22 | OR4N4 | 64 | APOB | 106 | PLCB1 | 148 | CACNA1C |
| 23 | BBOX1 | 65 | ACSM5 | 107 | CD1E | 149 | OR51L1 |
| 24 | OR5A2 | 66 | ZFP14 | 108 | SLC9A4 | 150 | PTPRT |
| 25 | MAGEB18 | 67 | FAM5C | 109 | OR2G3 | 151 | CACNA1I |
| 26 | ADAM2 | 68 | RIT2 | 110 | OR2T1 | 152 | CATSPERD |
| 27 | PDE1C | 69 | DNAH8 | 111 | TMEM132D | 153 | ZFHX4 |
| 28 | TAS2R16 | 70 | OR4C15 | 112 | ZNF804A | 154 | C2orf78 |
| 29 | CD177 | 71 | COL22A1 | 113 | KCNT2 | 155 | CHAT |
| 30 | SORCS3 | 72 | OR11L1 | 114 | NTRK3 | 156 | SPAG17 |
| 31 | GRM8 | 73 | RFX6 | 115 | FAM47A | 157 | UNC13C |
| 32 | HRNR | 74 | PSKH2 | 116 | PTGDR | 158 | POTEA |
| 33 | SPHKAP | 75 | MYH15 | 117 | OR4N2 | 159 | GRIN3A |
| 34 | EPHA6 | 76 | KALRN | 118 | ZNF536 | 160 | FAM5B |
| 35 | CSMD2 | 77 | TNR | 119 | OR2G6 | 161 | MORC1 |
| 36 | FAM83C | 78 | OR4B1 | 120 | LRP1B | 162 | NLRP14 |
| 37 | PEG3 | 79 | FCRL5 | 121 | OR2T6 | 163 | OR8B2 |
| 38 | OR5AC2 | 80 | NUP210L | 122 | ZSCAN1 | 164 | ACSM2B |
| 39 | USP29 | 81 | ZNF99 | 123 | OR5R1 | 165 | IRGC |
| 40 | ZNF208 | 82 | F5 | 124 | TRAT1 | 166 | ADCY8 |
| 41 | COL5A2 | 83 | MYH1 | 125 | OR6F1 | 167 | KIAA1462 |
| 42 | OR52N4 | 84 | EXPH5 | 126 | FIBIN | 168 | VEGFC |

FIG. 12
(continued)

| | | | | | | | |
|---|---|---|---|---|---|---|---|
| 169 | OR5J2 | 211 | MYH8 | 253 | ROBO4 | 295 | SI |
| 170 | GRIN2B | 212 | HSD3B2 | 254 | UBA3 | 296 | AOX1 |
| 171 | FAM47C | 213 | OR8I2 | 255 | NEU4 | 297 | TRHDE |
| 172 | MROH2B | 214 | RTP3 | 256 | SCN3A | 298 | RGS7 |
| 173 | DACH1 | 215 | OR52J3 | 257 | TRIM10 | 299 | OR52B2 |
| 174 | FAM135B | 216 | RP1 | 258 | AK024141 | 300 | BAI3 |
| 175 | TAC1 | 217 | THSD7B | 259 | TMEM200A | 301 | NLRP13 |
| 176 | FER1L6 | 218 | DGKK | 260 | FAM188B | 302 | DGKI |
| 177 | DUSP27 | 219 | CLVS2 | 261 | OR5B17 | 303 | CFHR5 |
| 178 | OR2M3 | 220 | SNTG2 | 262 | HDAC9 | 304 | PDE4DIP |
| 179 | LPA | 221 | NPC1L1 | 263 | NAA11 | 305 | GPR111 |
| 180 | FREM1 | 222 | CDH6 | 264 | LILRB1 | 306 | ZDHHC19 |
| 181 | CD163 | 223 | WDR49 | 265 | OR51M1 | 307 | SPATA31D1 |
| 182 | PRUNE2 | 224 | FAM24A | 266 | TRIM58 | 308 | FSHR |
| 183 | PTPRB | 225 | OR2L13 | 267 | NLRP4 | 309 | CWH43 |
| 184 | NAALAD2 | 226 | OR3A1 | 268 | OR4L1 | 310 | OR9Q2 |
| 185 | OR4D5 | 227 | KANK4 | 269 | OR4K1 | 311 | TENM3 |
| 186 | SPANXN2 | 228 | OR2F1 | 270 | F13A1 | 312 | TMEM132B |
| 187 | HYDIN | 229 | UNC79 | 271 | GABRB3 | 313 | CA10 |
| 188 | TCHHL1 | 230 | SYT4 | 272 | FOLH1B | 314 | PLCH1 |
| 189 | COL9A1 | 231 | ANKRD30A | 273 | SYNDIG1L | 315 | ZCCHC12 |
| 190 | OR8B4 | 232 | POM121L12 | 274 | PXDNL | 316 | LAIR2 |
| 191 | LDB2 | 233 | KCNB2 | 275 | MYH4 | 317 | OR5B2 |
| 192 | KLK5 | 234 | SHROOM3 | 276 | OR2T3 | 318 | OR2T34 |
| 193 | LEPR | 235 | LRRC7 | 277 | TIGD3 | 319 | TLR4 |
| 194 | CSMD3 | 236 | CNGB3 | 278 | OR8H3 | 320 | SIGLEC14 |
| 195 | MYH13 | 237 | CTNNA3 | 279 | MAGI2 | 321 | GCK |
| 196 | ADAM12 | 238 | SPTA1 | 280 | SLC6A19 | 322 | DNAH3 |
| 197 | RIMS2 | 239 | ABCA13 | 281 | CACNA1S | 323 | C6 |
| 198 | USH2A | 240 | ASTN1 | 282 | FSTL5 | 324 | ADAM29 |
| 199 | CDHR1 | 241 | AMER3 | 283 | KDR | 325 | OR2L3 |
| 200 | NEUROD1 | 242 | LY86 | 284 | OR5D14 | 326 | OR5L1 |
| 201 | FAT3 | 243 | ANKS1B | 285 | OR8H2 | 327 | PDILT |
| 202 | SELV | 244 | ACTRT2 | 286 | VN1R4 | 328 | UNC5D |
| 203 | C2orf16 | 245 | NLRP5 | 287 | PREX2 | 329 | RNF133 |
| 204 | CPA3 | 246 | PSG2 | 288 | GIMAP6 | 330 | OR2M7 |
| 205 | SEZ6L2 | 247 | SKP1 | 289 | AHNAK | 331 | GPR123 |
| 206 | ASF1B | 248 | TRIOBP | 290 | UGT3A1 | 332 | OR52E4 |
| 207 | COL19A1 | 249 | SAMD3 | 291 | OR4N5 | 333 | OR2F2 |
| 208 | NPTXR | 250 | DNAH5 | 292 | IMPG1 | 334 | ESRRG |
| 209 | CLEC6A | 251 | MRRF | 293 | OR10A2 | 335 | KCNH1 |
| 210 | CRISP2 | 252 | OC90 | 294 | CDR1 | 336 | PRR23B |

FIG. 12
(continued)

| | | | | | | | |
|---|---|---|---|---|---|---|---|
| 337 | PCDH15 | 379 | SCN2A | 421 | STON2 | 463 | OR52E6 |
| 338 | LRP2 | 380 | SLC5A8 | 422 | RYR2 | 464 | SALL1 |
| 339 | STAB2 | 381 | PARD3B | 423 | GRM7 | 465 | RYR3 |
| 340 | OR9A2 | 382 | CSH2 | 424 | SLCO6A1 | 466 | FUT9 |
| 341 | COL2A1 | 383 | NCKAP1L | 425 | PDGFRA | 467 | ZNF274 |
| 342 | JAM2 | 384 | DAB1 | 426 | TRPC5 | 468 | LCE3D |
| 343 | NPAP1 | 385 | GPR142 | 427 | OR4F17 | 469 | MYT1L |
| 344 | DCAF4L2 | 386 | OR2B6 | 428 | SLC17A6 | 470 | DNM3 |
| 345 | MYLK3 | 387 | SEMA5B | 429 | ARPP21 | 471 | TNXB |
| 346 | MYOCD | 388 | OR10C1 | 430 | CPED1 | 472 | ST6GAL2 |
| 347 | ITGA7 | 389 | ENTHD1 | 431 | OR10G7 | 473 | CCNB3 |
| 348 | OR8K5 | 390 | LCT | 432 | OR2M4 | 474 | DNAH10 |
| 349 | CLSTN2 | 391 | PI16 | 433 | NCKAP5 | 475 | MBL2 |
| 350 | CFTR | 392 | SLC35G3 | 434 | OR5AP2 | 476 | GABRB1 |
| 351 | PCK1 | 393 | SLC5A7 | 435 | KIF4B | 477 | PCDHB4 |
| 352 | TECRL | 394 | FOLH1 | 436 | RP1L1 | 478 | COL17A1 |
| 353 | RYR1 | 395 | PAK7 | 437 | KRTAP13-3 | 479 | TIE1 |
| 354 | PTPRD | 396 | FLT1 | 438 | OR1J4 | 480 | PYDC2 |
| 355 | MXRA5 | 397 | CNR1 | 439 | OR4A15 | 481 | KCNV1 |
| 356 | NPAS4 | 398 | ASXL3 | 440 | BPIFB4 | 482 | BTK |
| 357 | CDS1 | 399 | NLRP3 | 441 | MYO7B | 483 | AMPH |
| 358 | SLC6A18 | 400 | CIB4 | 442 | OR10G8 | 484 | CNGA2 |
| 359 | ROS1 | 401 | ADCY10 | 443 | ITGA4 | 485 | OR4X2 |
| 360 | BLK | 402 | DENND2A | 444 | MYF5 | 486 | BCAS1 |
| 361 | NPFFR2 | 403 | OR51S1 | 445 | SLIT2 | 487 | ADAM22 |
| 362 | OR51T1 | 404 | DNAH11 | 446 | PCDHGA1 | 488 | PHLDB2 |
| 363 | GRXCR1 | 405 | ALPK2 | 447 | SERPINI2 | 489 | WNT3A |
| 364 | SLCO1B3 | 406 | SPATA16 | 448 | ZSWIM2 | 490 | DCDC5 |
| 365 | CAPN13 | 407 | EMILIN3 | 449 | GPC5 | 491 | GAB4 |
| 366 | SELP | 408 | SLC17A8 | 450 | OR2T11 | 492 | OR8B12 |
| 367 | SCN11A | 409 | SIGLEC9 | 451 | OR8K1 | 493 | ELTD1 |
| 368 | TDRD5 | 410 | DCC | 452 | C7 | 494 | LPHN3 |
| 369 | UGT3A2 | 411 | OR4C3 | 453 | CLCN1 | 495 | NXF5 |
| 370 | DZIP3 | 412 | KRTAP12-4 | 454 | CYP11B2 | 496 | OR8G2 |
| 371 | LPAR4 | 413 | KCNK10 | 455 | C8orf34 | 497 | ADAMTS16 |
| 372 | ZDBF2 | 414 | CEACAM8 | 456 | ZNF676 | 498 | FSTL1 |
| 373 | TSHZ2 | 415 | HCN1 | 457 | COMMD1 | 499 | MYCT1 |
| 374 | PCDHGA3 | 416 | NOS1 | 458 | PCDHB7 | 500 | PMFBP1 |
| 375 | HOXB1 | 417 | TPO | 459 | OR11A1 | | |
| 376 | PSG7 | 418 | GRIN2A | 460 | KCNH7 | | |
| 377 | MYO18B | 419 | PPAPDC1A | 461 | MYH3 | | |
| 378 | NKAIN2 | 420 | OR2A12 | 462 | FCRL3 | | |

IMMUNOTHERAPY METHODS FOR PATIENTS WHOSE TUMORS CARRY A HIGH PASSENGER GENE MUTATION BURDEN

CROSS-REFERENCE TO RELATED APPLICATION

This application claims benefit of U.S. Provisional Application No. 62/560,955 filed Sep. 20, 2017, and is hereby incorporated herein by reference in its entirety.

REFERENCE TO SEQUENCE LISTING

The Sequence Listing submitted Sep. 19, 2018 as a text file named "37595_0015U2_Sequence_Listing.txt," created on Sep. 14, 2018, and having a size of 244,317 bytes is hereby incorporated by reference pursuant to 37 C.F.R. § 1.52(e)(5).

FIELD

The disclosure relates generally to the field of immunotherapy. More particularly, the disclosure relates to methods of administering an immunotherapy regimen to patients whose tumors have a high passenger gene mutation burden.

BACKGROUND

Various publications, including patents, patent applications, published patent applications, accession numbers, technical articles and scholarly articles are cited throughout the specification. Each of these cited publications is incorporated by reference, in its entirety and for all purposes, in this document.

Recent studies suggested that patients with higher overall tumor mutational burden (TMB) in their tumors are more likely to benefit from immunotherapy treatment due to the increase in neo-antigen presentation that could elicit an immune response. However, the overall mutational burden includes driver gene mutations that could actually suppress immunogenicity and decrease sensitivity to the treatment.

No existing method has been developed for the purpose of identifying passenger genes and their mutations to assess immunogenicity. These and other shortcomings are addressed in the present disclosure.

SUMMARY

It is to be understood that both the following general description and the following detailed description are exemplary and explanatory only and are not restrictive.

In a first aspect, the disclosure provides a method comprising receiving genetic sequence data, wherein the genetic sequence data comprises a plurality of genes and is derived from a plurality of biological samples collected from subjects having a plurality of disease types, identifying a plurality of mutated genes for each of the plurality of biological samples, wherein each of the mutated genes comprises a genetic sequence having at least one non-synonymous somatic mutation, determining a tumor mutational burden for each biological sample based on a number of mutated genes in each biological sample, for each disease type, determining an average tumor mutational burden of the plurality of mutated genes in the plurality of biological samples based on the determined numbers of mutated genes in each biological sample, for each mutated gene and each disease type, determining a fraction of biological samples comprising the mutated gene, for each mutated gene, determining a correlation coefficient between the average tumor mutational burden and the fraction of biological samples comprising the mutated gene. A higher correlation coefficient indicates that a particular gene is more likely to acquire somatic mutations in the cancer types with higher overall mutation frequency (e.g., passenger gene), whereas a lower correlation coefficient indicates that a particular gene is less likely to acquire somatic mutations in the cancer types with higher overall mutation frequency (e.g., not a passenger gene).

In another aspect, the disclosure provides methods for selecting a cancer patient for immunotherapy. In general, the methods comprise establishing a total passenger gene mutation burden from a tumor of the cancer patient, generating a background distribution for the mutational burden of the tumor, normalizing the total passenger gene mutation burden against the background distribution, and categorizing the cancer patient as an immunotherapy responder when the total passenger gene mutation burden is at least about one and a half standard deviations greater than the mean of the background distribution.

Generating a background distribution may comprise establishing the mutational burden from a plurality of samples of randomly selected genes obtained from the tumor, but the number of randomly selected genes in each sample preferably is equal to the number of passenger genes used to compute the total passenger gene mutation burden. Normalizing the total passenger gene mutation burden against the background distribution may comprise generating a z-score indicating the number of standard deviations from the mean of the background distribution.

The methods may further comprise categorizing a mutated gene in the tumor as a passenger gene. Categorizing a mutated gene in the tumor as a passenger gene may comprise selecting a mutated gene from the tumor and matching the mutated gene to a data structure comprising passenger genes established according to a passenger gene index. The passenger gene index may comprise a correlation coefficient between the fraction of samples comprising the mutated gene obtained from a cancer patient cohort and the median number of mutated genes in each type of tumor within the cancer patient cohort.

The methods may further comprise administering to the cancer patient an immunotherapy regimen. The immunotherapy regimen may comprise administering to the patient an inhibitor of a T cell inhibitory receptor. The immunotherapy regimen may comprise administering to the patient activator of T cell activating receptor.

The immunotherapy regimen may comprise administering to the patient an antibody that binds to PD1. The antibody that binds to PD1 may comprise at least the heavy chain variable region (HCVR) sequence of SEQ ID NO: 21 and a light chain variable region, or may comprise at least the light chain variable region (LCVR) sequence of SEQ ID NO: 22 and a heavy chain variable region. The antibody that binds to PD1 may comprise the HCVR or SEQ ID NO: 21 and the LCVR or SEQ ID NO: 22. That antibody that binds to PD1 may be administered in combination with an antibody that binds to LAG3.

The immunotherapy regimen may comprise administering to the patient an antibody that binds to PDL1. The antibody that binds to PDL1 may comprise at least the HCVR sequence of SEQ ID NO: 122 and a LCVR, or may comprise at least the LCVR sequence of SEQ ID NO: 123 and a HCVR. The antibody that binds to PDL1 may comprise the HCVR or SEQ ID NO: 122 and the LCVR or SEQ ID NO: 123. That antibody that binds to PDL1 may be administered in combination with an antibody that binds to LAG3.

The immunotherapy regimen may comprise administering to the patient an antibody that binds to LAG3. The antibody that binds to LAG3 may comprise at least the HCVR sequence of SEQ ID NO: 93 and a LCVR, or may comprise at least the LCVR sequence of SEQ ID NO: 94 and a HCVR. The antibody that binds to LAG3 may comprise the HCVR or SEQ ID NO: 93 and the LCVR or SEQ ID NO: 94. That antibody that binds to LAG3 may be administered in combination with an antibody that binds to PD1 or with an antibody that binds to PDL1.

Additional advantages will be set forth in part in the description which follows or may be learned by practice. The advantages will be realized and attained by means of the elements and combinations particularly pointed out in the appended claims.

BRIEF DESCRIPTION OF THE DRAWINGS

The accompanying drawings, which are incorporated in and constitute a part of this specification, illustrate embodiments and together with the description, serve to explain the principles of the methods and systems:

FIG. 8 shows the highest (left) and lowest (right) PGI CGC genes, and their corresponding cancer type with the highest percentage (>2%) of mutated sample;

FIG. 12 shows the top 500 passenger genes—highest Passenger Genes Index (PGI).

DETAILED DESCRIPTION

Figure 1:
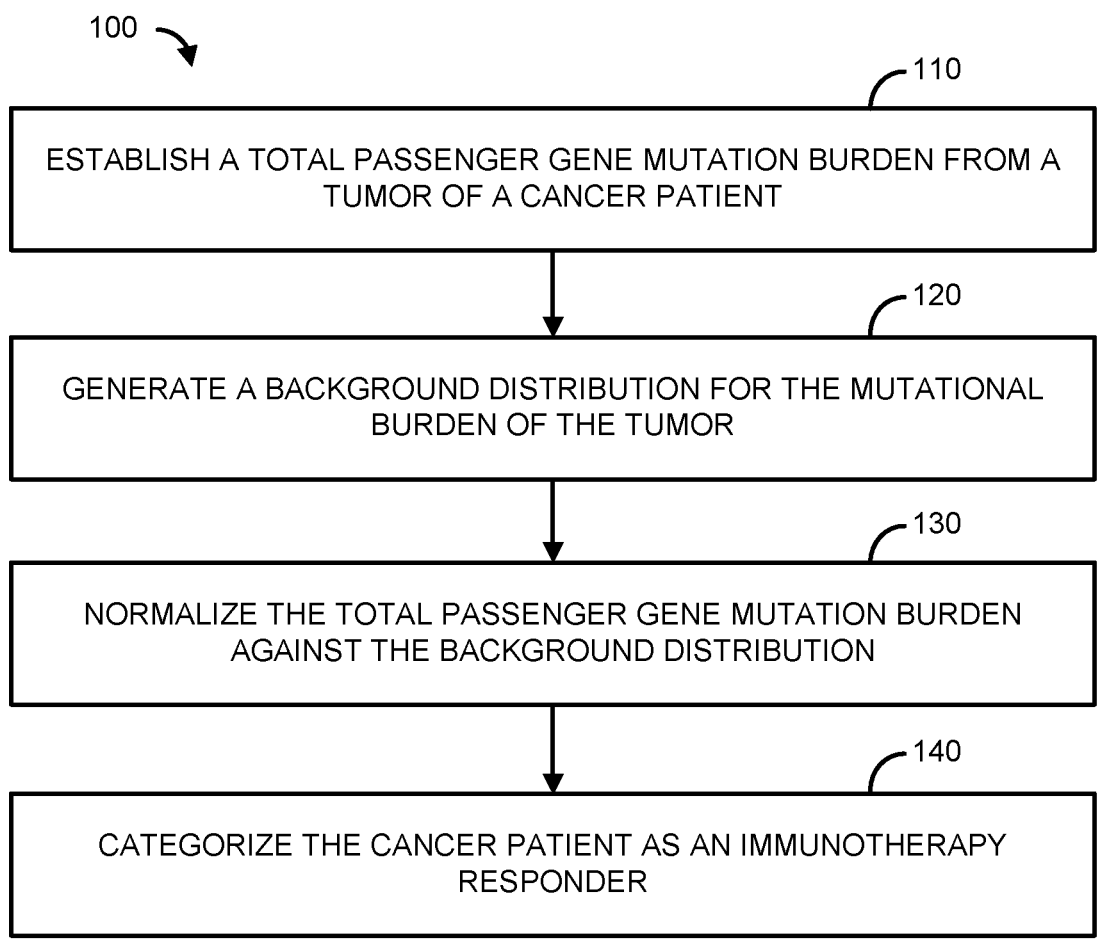
FIG. 1 shows a flowchart illustrating an example method.

Various terms relating to aspects of disclosure are used throughout the specification and claims. Such terms are to be given their ordinary meaning in the art, unless otherwise indicated. Other specifically defined terms are to be construed in a manner consistent with the definition provided herein.

As used in the specification and the appended claims, the singular forms "a," "an" and "the" include plural referents unless the context clearly dictates otherwise.

Inhibiting comprises reducing, decreasing, blocking, preventing, delaying, inactivating, desensitizing, stopping, and/or downregulating activity or expression of a molecule or pathway of interest.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

The terms "subject" and "patient" are used interchangeably and include any animal. Mammals are preferred, including companion (e.g., cat, dog) and farm mammals (e.g., pig, horse, cow), as well as rodents, including mice, rabbits, and rats, guinea pigs, and other rodents. Non-human primates are more preferred, and human beings are highly preferred.

It has been observed in accordance with the disclosure that, in cancer, the total mutational burden of passenger genes, as opposed to the total mutational burden of all genes, serves as an accurate indicator of whether a cancer patient is likely to respond positively to immunotherapy. Tumor mutational burden (TMB) may refer to a number of mutations within the coding region of a tumor genome. Mutated genes were assessed and classified according to their status as a passenger gene by way of a passenger gene index, which was used as a metric to identify passenger genes from a large-scale cancer genome analysis. It was observed that identified passenger genes were enriched for gene families known for excessive passenger mutations, including genes encoding large proteins, genes with low expression level, and genes with late DNA replication time. The total mutational burden of passenger genes positively correlated with tumor immunogenicity and favorably predicted patient clinical outcomes. Accordingly, the disclosure features methods to classify patients according to their passenger gene mutation burden, as part of an immunotherapy regimen.

In cancer biology, driver mutations are understood to be at least casually implicated in cancer formation or cell transformation. And passenger mutations are understood to be those that do not confer a growth advantage or contribute to cancer development. See Stratton MR et al. (2009) Nature. 458:719-24. Thus, passenger genes include genes that comprise passenger mutations. Non-limiting examples of mutations include substitutions, inversions, insertions, and deletions of one or more nucleotides, codons, genes, or chromosomes, as well as copy number variations.

In one aspect, the disclosure features methods and systems for identifying or classifying passenger genes. Identified passenger genes are enriched for families known for excessive passenger mutations, such as extremely large proteins and genes with low expression level or late DNA replication time. In some embodiments, passenger genes can be identified or classified according to a Passenger Gene Index (PGI). Thus, for example, passenger genes can be identified or classified according to a PGI that comprises a correlation coefficient between a fraction of samples obtained from a cancer patient cohort that comprises the mutated gene and the median number of mutated genes in each type of tumor within the cancer patient cohort. Based on identification of passenger genes, a data structure comprising passenger genes can be established.

Individual cancer patients can be screened to determine whether their tumors comprise passenger genes, as well as to determine the total passenger gene mutation burden of their tumor. Based on the patient's passenger gene mutation burden, the patient can be classified according to their capacity to respond positively to immunotherapy. Immunotherapy generally enhances the body's natural immune response to cancer, and includes, but is not limited to, the enhancement of the T cell response to the tumor.

An example of a methodology by which a cancer patient may be assessed for immunotherapy responsiveness is shown in FIG. 1. In general, the methods comprise establishing a total passenger gene mutation burden from a tumor of a cancer patient (110), generating a background distribution for the mutational burden of the tumor (120), normalizing the total passenger gene mutation burden against the background distribution (130), and categorizing the cancer patient as an immunotherapy responder (140).

Also disclosed are methods of treating a cancer patient with an immunotherapy after being assessed for immunotherapy responsiveness. For example, disclosed are methods of treating a cancer patient with an immunotherapy comprising determining if a cancer patient is an immunotherapy responder comprising establishing a total passenger gene mutation burden of the tumor of the patient; generating a background distribution for the mutational burden of the tumor; normalizing the total passenger gene mutation burden against the background distribution; and categorizing the cancer patient as an immunotherapy responder genotype when the total passenger gene mutation burden is at least about one and a half standard deviations greater than the mean of the background distribution; and administering an immunotherapy to the cancer patient categorized as an immunotherapy responder.

Further disclosed are methods for treating a patient with an inhibitor of a T cell inhibitory receptor or a receptor on a tumor cell or a non-immunotherapeutic treatment, wherein the patient is suffering from cancer, the method comprising the steps of: determining whether the patient is an immunotherapy responder by: obtaining or having obtained a biological sample from a tumor of the patient; performing or having performed a genotyping assay on the biological sample to determine if the patient has an immunotherapy responder genotype by, sequencing the biological sample to generate sequence data; establishing, based on the sequence data, a total passenger gene mutation burden of the tumor of the patient; generating, based on the sequence data, a background distribution for the mutational burden of the tumor; normalizing the total passenger gene mutation burden against the background distribution; and categorizing the patient as an immunotherapy responder genotype when the total passenger gene mutation burden is at least about one and a half standard deviations greater than the mean of the background distribution; wherein if the patient has an immunotherapy responder genotype, then administering a therapeutically effective amount of an inhibitor of a T cell inhibitory receptor or a receptor on a tumor cell, wherein if the patient does not have an immunotherapy responder genotype, then administering a non-immunotherapeutic treatment. In some embodiments, a risk of unfavorable clinical outcome for a patient having an immunotherapy responder genotype is lower following the administration of the therapeutically effective amount of the inhibitor of a T cell inhibitory receptor or a receptor on a tumor cell than it would be if the patient were administered the non-immunotherapeutic treatment. In some embodiments, T cell activation and/or immune cytolytic activity in a patient having an immunotherapy responder genotype is higher following the administration of the therapeutically effective amount of the inhibitor of a T cell inhibitory receptor or a receptor on a tumor cell than it would be if the patient were administered the non-immunotherapeutic treatment.

Disclosed are immunotherapies for use in the method of treating a cancer patient, the method comprising determining if a cancer patient is an immunotherapy responder by, establishing a total passenger gene mutation burden of a tumor of the patient; generating a background distribution for the mutational burden of the tumor; normalizing the total passenger gene mutation burden against the background distribution; categorizing the cancer patient as an immunotherapy responder genotype when the total passenger gene mutation burden is at least about one and a half standard deviations greater than the mean of the background distribution; and administering the immunotherapy to the cancer patient categorized as an immunotherapy responder.

In some preferred embodiments, establishing a total passenger gene mutation burden from a tumor of a cancer patient (110) may comprise determining the total passenger gene mutation burden by any sequencing method that is used to determine the coding regions ("exome") of a tumor genome. Whole genome sequencing methods can also be used.

Exome mutations can be determined using sequencing methods known in the art. For example, US 2013/0040863, incorporated herein by reference, describes methods for determining the nucleic acid sequence of a target nucleic acid molecule, including sequencing by synthesis, sequencing by ligation or sequencing by hybridization, including for mutation detection, whole genome sequencing, and exon sequencing. If desired, various amplification methods can be used to generate larger quantities, particularly of limited nucleic acid samples, prior to sequencing.

Sequencing by synthesis (SBS) and sequencing by ligation can be performed using ePCR, as used by 454 Lifesciences (Branford, Conn.) and Roche Diagnostics (Basel, Switzerland). Nucleic acids such as genomic DNA or others of interest can be fragmented, dispersed in water/oil emulsions and diluted such that a single nucleic acid fragment is separated from others in an emulsion droplet. A bead, for example, containing multiple copies of a primer, can be used and amplification carried out such that each emulsion droplet serves as a reaction vessel for amplifying multiple copies of a single nucleic acid fragment. Other methods can be used, such as bridging PCR (Illumina, Inc.; San Diego Calif.), or polony amplification (Agencourt/Applied Biosystems). US 2009/0088327; US 2010/0028885; and US 2009/0325172, each of which is incorporated herein by reference.

Methods for manual or automated sequencing are well known in the art and include, but are not limited to, Sanger sequencing, Pyrosequencing, sequencing by hybridization, sequencing by ligation and the like. Sequencing methods can be performed manually or using automated methods. Furthermore, the amplification methods set forth herein can be used to prepare nucleic acids for sequencing using commercially available methods such as automated Sanger sequencing (available from Applied Biosystems, Foster City, Calif.) or Pyrosequencing (available from 454 Lifesciences, Branford, Conn. and Roche Diagnostics, Basel, Switzerland); for sequencing by synthesis methods commercially available from Illumina, Inc. (San Diego, Calif.) or Helicos (Cambridge, Mass.) or sequencing by ligation methods being developed by Applied Biosystems in its Agencourt platform (see also Ronaghi et al., Science 281:363 (1998); Dressman et al., Proc. Natl. Acad. Sci. USA 100:8817-8822 (2003); Mitra et al., Proc. Natl. Acad. Sci. USA 100:55926-5931 (2003)), incorporated herein by reference.

A population of nucleic acids in which a primer is hybridized to each nucleic acid such that the nucleic acids form templates and modification of the primer occurs in a template directed fashion. The modification can be detected to determine the sequence of the template. For example, the primers can be modified by extension using a polymerase and extension of the primers can be monitored under conditions that allow the identity and location of particular nucleotides to be determined. For example, extension can be monitored and sequence of the template nucleic acids determined using pyrosequencing, which is described in US 2005/0130173, US 2006/0134633, U.S. Pat. Nos. 4,971,903; 6,258,568 and 6,210,891, each of which is incorporated herein by reference, and is also commercially available. Extension can also be monitored according to addition of labeled nucleotide analogs by a polymerase, using methods described, for example, in U.S. Pat. Nos. 4,863,849; 5,302,509; 5,763,594; 5,798,210; 6,001,566; 6,664,079; U.S. 2005/0037398; and U.S. Pat. No. 7,057,026, each of which is incorporated herein by reference. Polymerases useful in sequencing methods are typically polymerase enzymes derived from natural sources. It will be understood that polymerases can be modified to alter their specificity for modified nucleotides as described, for example, in WO 01/23411; U.S. Pat. No. 5,939,292; and WO 05/024010, each of which is incorporated herein by reference. Furthermore, polymerases need not be derived from biological systems. Polymerases that are useful in the invention include any agent capable of catalyzing extension of a nucleic acid primer in a manner directed by the sequence of a template to which the primer is hybridized. Typically polymerases will be protein enzymes isolated from biological systems.

Alternatively, exon sequences can be determined using sequencing by ligation as described, for example, in Shendure et al. Science 309:1728-1732 (2005); U.S. Pat. Nos. 5,599,675; and 5,750,341, each of which is incorporated herein by reference. Sequences of template nucleic acids can be determined using sequencing by hybridization methods such as those described in U.S. Pat. Nos. 6,090,549; 6,401,267 and 6,620,584, each of which is incorporated herein by reference.

If desired, exon sequence products are detected using a ligation assay such as oligonucleotide ligation assay (OLA). Detection with OLA involves the template-dependent ligation of two smaller probes into a single long probe, using a target sequence in an amplicon as the template. In a particular embodiment, a single-stranded target sequence includes a first target domain and a second target domain, which are adjacent and contiguous. A first OLA probe and a second OLA probe can be hybridized to complementary sequences of the respective target domains. The two OLA probes are then covalently attached to each other to form a modified probe. In embodiments where the probes hybridize directly adjacent to each other, covalent linkage can occur via a ligase. One or both probes can include a nucleoside having a label such as a peptide linked label. Accordingly, the presence of the ligated product can be determined by detecting the label. In particular embodiments, the ligation probes can include priming sites configured to allow amplification of the ligated probe product using primers that hybridize to the priming sites, for example, in a PCR reaction.

Alternatively, the ligation probes can be used in an extension-ligation assay wherein hybridized probes are non-contiguous and one or more nucleotides are added along with one or more agents that join the probes via the added nucleotides. Furthermore, a ligation assay or extension-ligation assay can be carried out with a single padlock probe instead of two separate ligation probes.

In some preferred embodiments, generating a background distribution (120) comprises establishing the mutational burden from a plurality of samples of randomly selected genes obtained from the tumor, provided that the number of randomly selected genes in each sample is equal to the number of passenger genes used to compute the total passenger gene mutation burden.

In some preferred embodiments, normalizing the total passenger gene mutation burden against the background distribution (130) comprises generating a z-score indicating the number of standard deviations from the mean of the background distribution. In an alternative embodiment, p-values can be used. Z-scores can be correlated to p-values. For example, a z-score of 1.65 equals a p-value of $p<0.05$ and a z-score of 2.3 equals a p-value of $p<0.01$.

Categorizing the cancer patient as an immunotherapy responder may be according to the relationship of the total passenger gene mutation burden to the mean of the background distribution. For example, the patient may be categorized as an immunotherapy responder when the total passenger gene mutation burden is at least a number of standard deviations greater than the mean of the background distribution. The number of standard deviations can be, for example, at least about 1, at least about 1.5, at least about 2, at least about 2.5, at least about 3, or greater than 3 standard deviations greater than the mean of the background distribution.

In some embodiments, a cancer patient can be suffering from cutaneous squamous cell cancer (CSCC), bladder urothelial carcinoma (BLCA), breast invasive carcinoma (BRCA), cervical squamous cell carcinoma and endocervical adenocarcinoma (CESC), colon/rectum adenocarcinoma (CORE), glioblastoma multiforme (GBM), head and neck squamous cell carcinoma (HNSC), kidney renal clear cell carcinoma (KIRC), kidney renal papillary cell carcinoma (KIRP), acute myeloid leukemia (LAML), liver hepatocellular carcinoma (LIHC), brain lower grade glioma (LGG), lung adenocarcinoma (LUAD), lung squamous cell carcinoma (LUSC), ovarian serous cystadenocarcinoma (OV), pheochromocytoma and paraganglioma (PCPG), prostate adenocarcinoma (PRAD), skin cutaneous melanoma (SKCM), stomach adenocarcinoma.

In some embodiments, the methods further comprise categorizing a mutated gene in the tumor as a passenger gene. Categorizing a mutated gene in the tumor as a passenger gene may comprise selecting a mutated gene from the tumor and matching the mutated gene to a data structure comprising passenger genes established according to a passenger gene index. The passenger gene index may comprises a correlation coefficient between the fraction of samples comprising the mutated gene obtained from a cancer patient cohort and the median number of mutated genes in each type of tumor within the cancer patient cohort.

When a cancer patient is categorized as an immunotherapy responder, the method may further comprise administering to the cancer patient an immunotherapy regimen. In some embodiments, the immunotherapy regimen comprises administering to the patient an inhibitor of a T cell inhibitory receptor or a receptor on a tumor cell. In some embodiments, an inhibitor of T cell inhibitory receptor or receptor on a tumor cell can comprise an antibody or antigen-binding fragment thereof. In some embodiments, the immunotherapy regimen comprises administering to the patient an activator of a T cell receptor that promotes T cell activation and prolongs immune cytolytic activities.

In some embodiments, T cell inhibitory receptors or receptors on a tumor cell, which can be targeted with inhibitors for immunotherapy comprise one or more of PD1, PDL1, CTLA4, LAG3 and TIM3. Thus, in some embodiments, an inhibitor of a T cell inhibitory receptor or a receptor on a tumor cell comprises an antibody or antigen-binding fragment thereof that specifically binds to one or more of PD1, PDL1, CTLA4, LAG3, and TIM3. As part of an immunotherapy regimen, the cancer patient may be administered an antibody or antigen-binding fragment thereof that specifically binds to one or more of PD1, PDL1, CTLA4, LAG3, and TIM3, or may be administered any combination of two or more such antibodies or antigen-binding fragments thereof.

In some embodiments, the immunotherapy regimen comprises administering to the patient an antibody that binds to PD1. In some preferred embodiments, the antibody that binds to PD1 comprises at least the heavy chain variable region (HCVR) sequence of SEQ ID NO:21 and the light chain variable region (LCVR) sequence of SEQ ID NO:22. In embodiments, any of the antibodies or antigen-binding fragments thereof that bind PD1 can be any of the antibodies or antigen-binding fragments thereof described in U.S. application Ser. No. 14/603,776 (Publication No. US 2015-0203579), which is hereby incorporated by reference herein. For example, in some embodiments, the antibody or antigen-binding fragment thereof that binds to PD1 comprises a HCVR having an amino acid sequence from among the sequences listed in Table 1 and a LCVR. In some embodiments, the antibody or antigen-binding fragment thereof that binds to PD1 comprises a LCVR having an amino acid sequence from among the sequences listed in Table 1 and an HCVR. In some embodiments, the antibody or antigen-binding fragment thereof that binds to PD1 comprises an HCVR and LCVR pair as shown in Table 1. Other antibodies that bind to PD1 can be used (or antigen-binding fragments thereof), and these include but are not limited to pembrolizumab, nivolumab, durvalumab, atezolizumab, pidilizumab, camrelizumab, PDR001, MED10680, JNJ-63723283, and MCLA-134.

TABLE 1

Amino Acid Sequence Identifiers for PD1 antibodies

| HCVR SEQ ID NO: | LCVR SEQ ID NO: | HCVR SEQ ID NO: | LCVR SEQ ID NO: |
|---|---|---|---|
| 1 | 2 | 28 | 26 |
| 3 | 4 | 29 | 26 |
| 5 | 6 | 30 | 26 |
| 7 | 8 | 31 | 26 |
| 9 | 10 | 32 | 26 |
| 11 | 12 | 33 | 26 |
| 13 | 14 | 34 | 26 |
| 15 | 16 | 35 | 26 |
| 17 | 18 | 36 | 26 |
| 19 | 20 | 37 | 26 |
| 21 | 22 | 38 | 24 |
| 23 | 24 | 39 | 24 |
| 25 | 26 | 40 | 24 |
| 27 | 26 | | |

In some embodiments, the immunotherapy regimen comprises administering to the patient an antibody that binds to the LAG3 protein (aka CD223). In some embodiments, the antibody that binds to LAG3 comprises at least the HCVR sequence of SEQ ID NO:93 and the LCVR sequence of SEQ ID NO:94. In some embodiments, the antibodies or antigen-binding fragments thereof that bind LAG3 can be any of the antibodies or antigen-binding fragments thereof described in U.S. application Ser. No. 15/289,032 (Publication No. US 2017-0101472), which is hereby incorporated by reference herein. For example, in some embodiments, the antibody or antigen-binding fragment thereof that binds to LAG3 comprises a HCVR having an amino acid sequence from among the sequences listed in Table 2 and a LCVR. In some embodiments, the antibody or antigen-binding fragment thereof that binds to LAG3 comprises a LCVR having an amino acid sequence from among the sequences listed in Table 2 and an HCVR. In some embodiments, the antibody or antigen-binding fragment thereof that binds to LAG3 comprises an HCVR and LCVR pair as shown in Table 2. Other antibodies that bind to LAG3 can be used (or antigen-binding fragments thereof), and these include but are not limited to BMS-986016 and GSK2381781.

TABLE 2

Amino Acid Sequence Identifiers for LAG3 antibodies

| HCVR SEQ ID NO: | LCVR SEQ ID NO: | HCVR SEQ ID NO: | LCVR SEQ ID NO: |
|---|---|---|---|
| 41 | 42 | 81 | 82 |
| 43 | 44 | 83 | 84 |
| 45 | 46 | 85 | 86 |
| 47 | 48 | 87 | 88 |
| 49 | 50 | 89 | 90 |
| 51 | 52 | 91 | 92 |
| 53 | 54 | 93 | 94 |
| 55 | 56 | 95 | 96 |
| 57 | 58 | 97 | 98 |
| 59 | 60 | 99 | 98 |
| 61 | 62 | 100 | 98 |
| 63 | 64 | 101 | 98 |
| 65 | 66 | 102 | 98 |
| 67 | 68 | 103 | 98 |
| 69 | 70 | 104 | 105 |
| 71 | 72 | 106 | 105 |

TABLE 2-continued

Amino Acid Sequence Identifiers for LAG3 antibodies

| HCVR SEQ ID NO: | LCVR SEQ ID NO: | HCVR SEQ ID NO: | LCVR SEQ ID NO: |
|---|---|---|---|
| 73 | 74 | 107 | 105 |
| 75 | 76 | 108 | 109 |
| 77 | 78 | 110 | 111 |
| 79 | 80 | | |

In some embodiments, the immunotherapy regimen comprises administering to the patient an antibody that binds to PDL1. In some preferred embodiments, the antibody that binds to PDL1 comprises at least the HCVR sequence of SEQ ID NO:122 and the LCVR sequence of SEQ ID NO:123. In some embodiments, the antibodies or antigen-binding fragments thereof that bind PDL1 can be any of the antibodies or antigen-binding fragments thereof described in U.S. application Ser. No. 14/603,808 (Publication No. US 2015-0203580), which is hereby incorporated by reference herein. For example, in some embodiments, the antibody or antigen-binding fragment thereof that binds to PDL1 comprises a HCVR having an amino acid sequence from among the sequences listed in Table 3 and a LCVR. In some embodiments, the antibody or antigen-binding fragment thereof that binds to PDL1 comprises a LCVR having an amino acid sequence from among the sequences listed in Table 3 and an HCVR. In some embodiments, the antibody or antigen-binding fragment thereof that binds to PDL1 comprises an HCVR and LCVR pair as shown in Table 3. Other antibodies that bind to PDL1 can be used (or antigen-binding fragments thereof), and these include but are not limited to, one or more of avelumab, atezolizumab, and durvalumab.

TABLE 3

Amino Acid Sequence Identifiers for PDL1 antibodies

| HCVR SEQ ID NO: | LCVR SEQ ID NO: | HCVR SEQ ID NO: | LCVR SEQ ID NO: |
|---|---|---|---|
| 112 | 113 | 137 | 138 |
| 114 | 115 | 139 | 140 |
| 116 | 117 | 141 | 142 |
| 118 | 119 | 143 | 144 |
| 120 | 121 | 145 | 146 |
| 122 | 123 | 147 | 146 |
| 124 | 125 | 148 | 146 |
| 126 | 127 | 149 | 146 |
| 128 | 129 | 150 | 146 |
| 130 | 131 | 151 | 146 |
| 132 | 133 | 152 | 146 |
| 134 | 133 | 153 | 146 |
| 135 | 136 | 154 | 146 |

In some embodiments, the immunotherapy regimen comprises administering to the patient an antibody that binds to CTLA4. In some embodiments, the antibodies or antigen-binding fragments thereof that bind CTLA4 can be any of the antibodies or antigen-binding fragments thereof described in U.S. Provisional Application No. 62/537,753, filed on Jul. 27, 2017, which is hereby incorporated by reference herein. For example, in some embodiments, the antibody or antigen-binding fragment thereof that binds to CTLA4 comprises a HCVR having an amino acid sequence from among the sequences listed in Table 4 and a LCVR. In some embodiments, the antibody or antigen-binding fragment thereof that binds to CTLA4 comprises a LCVR having an amino acid sequence from among the sequences listed in Table 4 and an HCVR. In some embodiments, the antibody or antigen-binding fragment thereof that binds to CTLA4 comprises an HCVR and LCVR pair as shown in Table 4. Other antibodies that bind to CTLA4 can be used (or antigen-binding fragments thereof), and these include but are not limited to, one or more of ipilimumab and tremelimumab, as well as any of the antibodies or antigen-binding fragments thereof disclosed in U.S. Pat. Nos. 6,984,720; 7,605,238; or 7,034,121, all of which are hereby incorporated by reference herein.

TABLE 4

Amino Acid Sequence Identifiers for CTLA4 antibodies

| HCVR | LCVR | HCVR | LCVR |
|---|---|---|---|
| 155 | 156 | 187 | 188 |
| 157 | 158 | 189 | 190 |
| 159 | 160 | 191 | 192 |
| 161 | 162 | 193 | 192 |
| 163 | 164 | 195 | 194 |
| 165 | 166 | 197 | 196 |
| 167 | 168 | 199 | 198 |
| 169 | 170 | 201 | 200 |
| 171 | 172 | 203 | 202 |
| 173 | 174 | 205 | 204 |
| 175 | 176 | 207 | 206 |
| 177 | 178 | 209 | 208 |
| 179 | 180 | 211 | 210 |
| 181 | 182 | 213 | 212 |
| 183 | 184 | 215 | 214 |
| 185 | 186 | 217 | 216 |

In some embodiments, the immunotherapy regimen may comprise administering to the patient a combination of one or more inhibitors of a T cell inhibitory receptor. The combination may comprise a combination of antibodies or a combination of antigen-binding portions of such antibodies, or a combination of antibodies and antigen-binding portions. Thus, for example, the immunotherapy regimen may comprise administering to the patient an antibody that binds to PD1 in combination with a second immunotherapy regimen, such as an antibody that binds to LAG3, or an antibody that binds to PDL1, or an antibody that binds to CTLA. The immunotherapy regimen may comprise administering to the patient an antibody that binds to PDL1 in combination with a second immunotherapy regimen, such as an antibody that binds to LAG3, or an antibody that binds to PD1, or an antibody that binds to CTLA. The immunotherapy regimen may comprise administering to the patient an antibody that binds to LAG3 in combination with a second immunotherapy regimen, such as an antibody that binds to PD1, or an antibody that binds to PDL1, or an antibody that binds to CTLA. The immunotherapy regimen may comprise administering to the patient an antibody that binds to CTLA4 in combination with a second immunotherapy regimen, such as an antibody that binds to LAG3, or an antibody that binds to PDL1, or an antibody that binds to PD1. The antibody that binds to PD1 may comprise any antibody or antigen binding domain described or exemplified herein. The antibody that binds to PD1 may comprise any antibody or antigen binding domain described or exemplified herein. The antibody that binds to PDL1 may comprise any antibody or antigen binding domain described or exemplified herein. The antibody that binds to LAG3 may comprise any antibody or antigen binding domain described or exemplified herein. The antibody that binds to CTLA4 may comprise any antibody or antigen binding domain described or exemplified herein.

In some preferred embodiments, the immunotherapy regimen comprises administering to the patient a combination of an antibody, or antigen binding portion thereof, that binds to PD1 and an antibody, or antigen-binding portion thereof, that binds to LAG3. In some preferred embodiments, the antibody that binds to PD1 comprises at least the heavy chain variable region (HCVR) sequence of SEQ ID NO:21 and the light chain variable region (LCVR) sequence of SEQ ID NO:22, and the antibody that binds to LAG3 comprises at least the HCVR sequence of SEQ ID NO:93 and the LCVR sequence of SEQ ID NO:94.

In some preferred embodiments, the immunotherapy regimen comprises administering to the patient a combination of an antibody, or antigen binding portion thereof, that binds to PDL1 and an antibody, or antigen-binding portion thereof, that binds to LAG3. In some preferred embodiments, the antibody that binds to PDL1 comprises at least the heavy chain variable region (HCVR) sequence of SEQ ID NO:122 and the light chain variable region (LCVR) sequence of SEQ ID NO:123, and the antibody that binds to LAG3 comprises at least the HCVR sequence of SEQ ID NO:93 and the LCVR sequence of SEQ ID NO:94.

In some embodiments, the immunotherapy can be any of the known immunotherapies for cancer. For example, the immunotherapy can be cemiplimab, nivolumab, pembrolizumab, atezolizumab, durvalumab, avelumab, ipilimumab, IFN-alpha, IL-2, or a combination thereof. In some embodiments, the immunotherapy can be an immune checkpoint inhibitor as described throughout or those commonly known in the art. For example, cemiplimab, nivolumab, pembrolizumab, atezolizumab, durvalumab, avelumab are known immune checkpoint inhibitors.

In some alternative embodiments, the immunotherapy regimen comprises administering to the patient an activator of T cell activating receptor. In some preferred embodiments, a T cell activating receptor, which can be targeted with activators for immunotherapy comprise one or more of CD28, CD40L, ICOS and 4-1BB.

Figure 2:
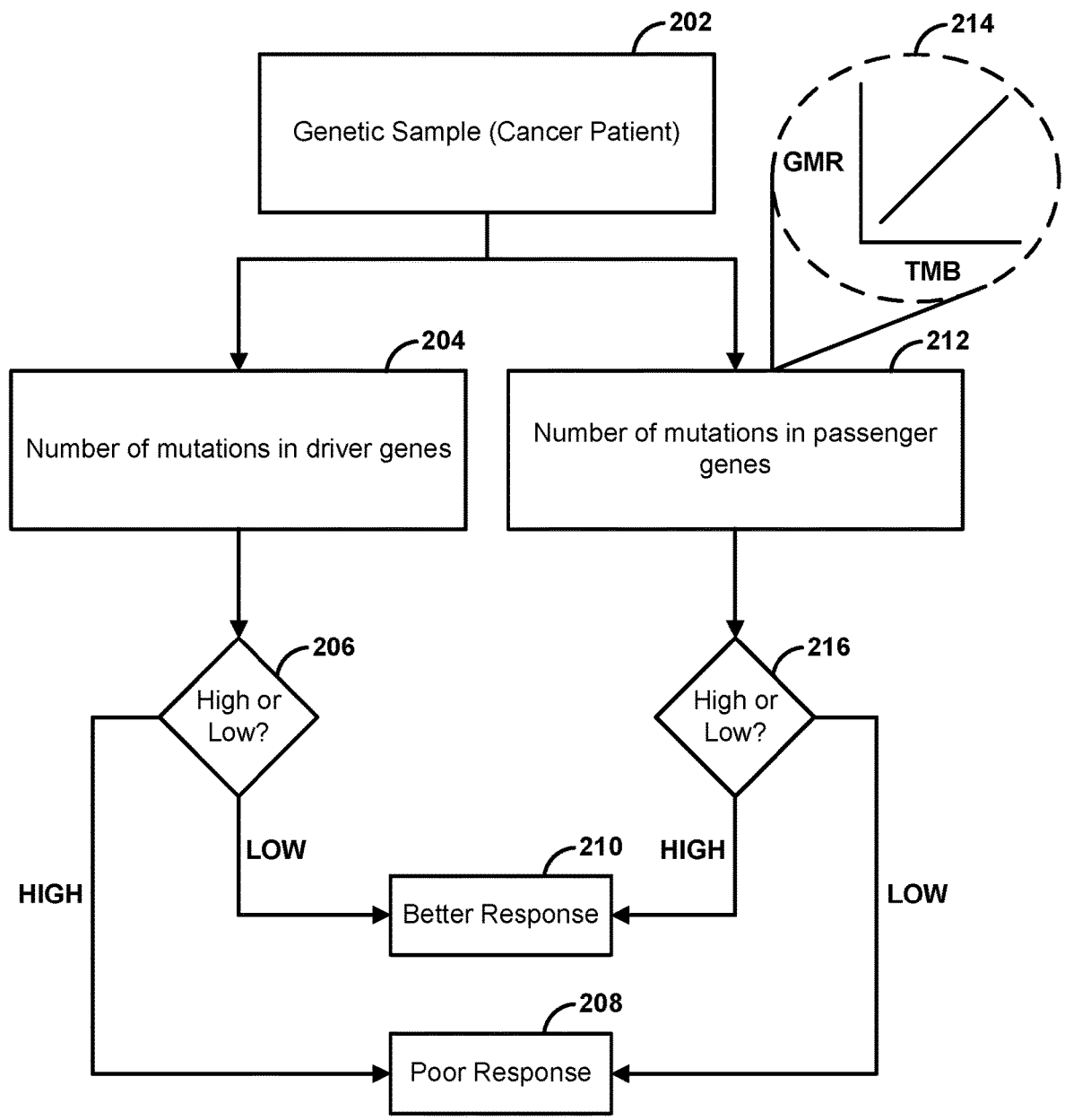
FIG. 2 shows a flowchart illustrating an example method.
Figure 3:
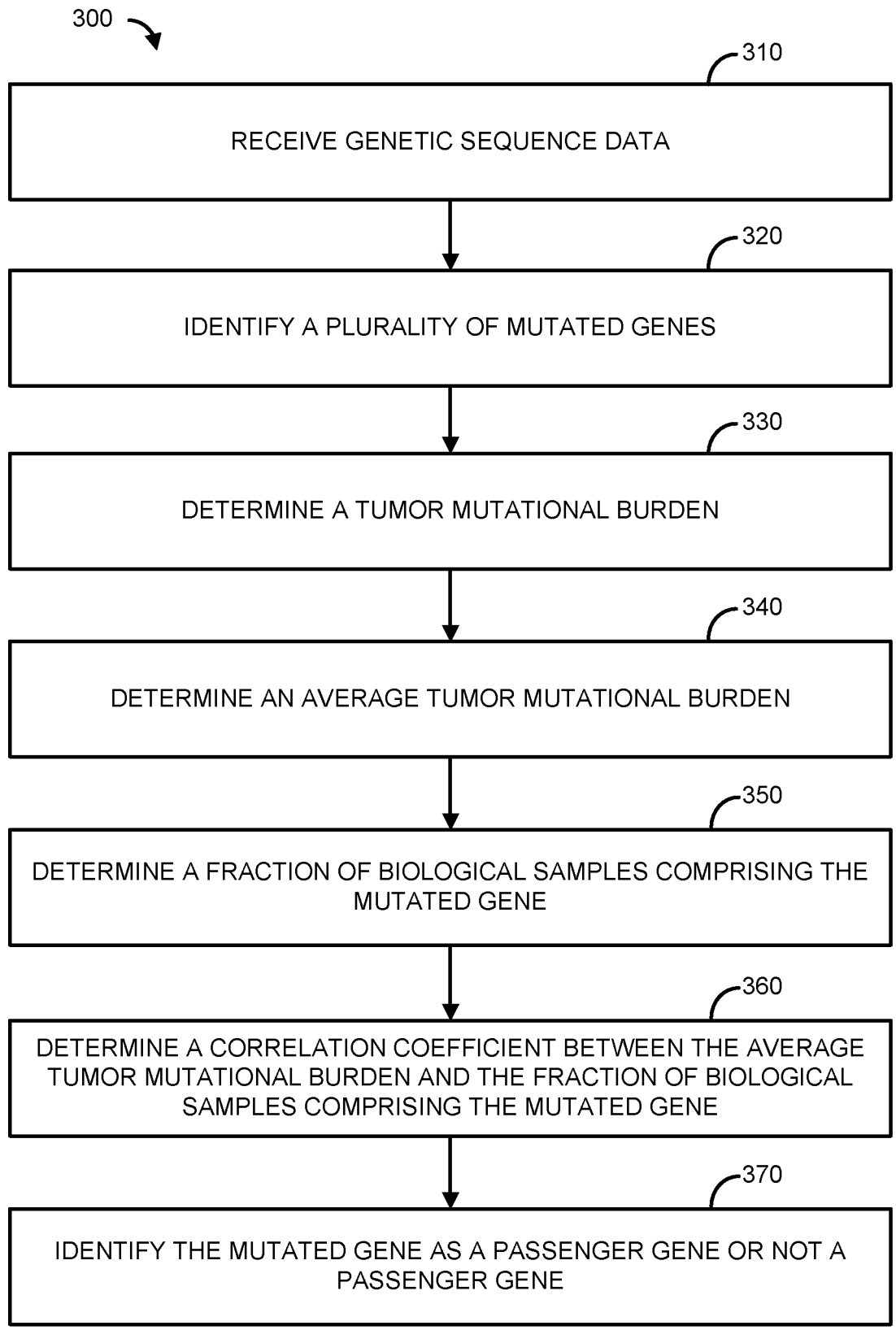
FIG. 3 shows a flowchart illustrating another example method.

An example of a methodology for establishing a total passenger gene mutation burden from a tumor of a cancer patient is shown in FIG. 2 and FIG. 3. A genetic sample can be obtained/received (202). The genetic sample can be from a cancer patient. The genetic sample can be from a tumor of the cancer patient. The genetic sample can be sequenced, resulting in genetic sequence data.

In some embodiments, the sequence data can be obtained or received through any method described herein. For example, the sequence data can be obtained directly, by performing a sequencing process on a sample. Alternatively, or additionally, the sequence data can be obtained indirectly, for example, from a third party, a database and/or a publication. In some embodiments, the sequence data are received at a computer system, for example, from a data storage device or from a separate computer system.

In some embodiments, the sequence data can comprise bulk sequence data. The term "bulk sequencing" or "next generation sequencing" or "massively parallel sequencing" refers to any high throughput sequencing technology that parallelizes the DNA and/or RNA sequencing process. For example, bulk sequencing methods are typically capable of producing more than one million polynucleic acid amplicons in a single assay. The terms "bulk sequencing," "massively parallel sequencing," and "next generation sequencing" refer only to general methods, not necessarily to the acquisition of greater than 1 million sequence tags in a single run. Any bulk sequencing method can be implemented in the disclosed methods and systems, such as reversible terminator chemistry (e.g., Illumina), pyrosequencing using polony emulsion droplets (e.g., Roche), ion semiconductor sequencing (IonTorrent), single molecule sequencing (e.g., Pacific Biosciences), massively parallel signature sequencing, etc.

In some embodiments, the sequence data can be produced by any sequencing method known in the art. For example, in some embodiments the sequencing data are produced using chain termination sequencing, sequencing by ligation, sequencing by synthesis, pyrosequencing, ion semiconductor sequencing, single-molecule real-time sequencing, tag-based sequencing, dilute-'n'-go sequencing, and/or 454 sequencing.

In some embodiments, the sequence data are the result of a process whereby a nucleic acid amplification process is performed to amplify at least part of one or more genomic locus or transcript, followed by the sequencing of the resulting amplification product. Examples of nucleic acid amplification processes useful in the performance of methods disclosed herein include, but are not limited to, polymerase chain reaction (PCR), LATE-PCR, ligase chain reaction (LCR), strand displacement amplification (SDA), transcription mediated amplification (TMA), self-sustained sequence replication (3SR), Qβ replicase based amplification, nucleic acid sequence-based amplification (NASBA), repair chain reaction (RCR), boomerang DNA amplification (BDA) and/or rolling circle amplification (RCA).

In some embodiments, the method includes the step of performing a sequencing process on a sample. Any sample can be used, so long as the sample contains DNA and/or RNA from a tumor of a patient. The source of the sample may be, for example, solid tissue, as from a fresh, frozen and/or preserved organ, tissue sample, biopsy, or aspirate; blood or any blood constituents, serum, blood; bodily fluids such as cerebral spinal fluid, amniotic fluid, peritoneal fluid or interstitial fluid.

The genetic sequence data can be analyzed (204) via a computing device to identity driver genes and to determine a number of mutations in the driver genes. If the number of mutations in the driver genes is high (206), an indication can be generated that the patient will respond to the immunotherapy (210). If the number of mutations in the driver genes is low (206), an indication can be generated poor or no response will be seen with immunotherapy (208). Mutations on driver genes could promote "hallmarks of cancer" e.g., immune escape.

In an alternate embodiment, the genetic sequence data can be analyzed (212) via a computing device to identify passenger genes and to determine a number of mutations in the passenger genes. If the number of mutations in the passenger genes is high (216), an indication can be generated (210) that the patient will respond to the immunotherapy. If the number of mutations in the passenger genes is low (216), an indication can be generated (208) that poor or no response will be seen with immunotherapy. While passenger genes do not have any causal implication in cancer, mutations on passenger genes can be used to assess immunogenicity. In some embodiments, the genetic sequence data can be analyzed (212) to identify passenger genes, determine a number of mutations in the passenger genes, and determine a background distribution for the mutational burden of the tumor. The number of mutations in the passenger genes can be analyzed with regard to the background distribution to determine how many standard deviations (if any) the number of mutations in the passenger genes is from the mean. If the number of standard deviations is high (e.g., at least 1, 1.5, 2, 2.5) (216) the cancer patient can be categorized as a better immunotherapy responder (210). If the number of standard deviations is low (216) the cancer patient can be categorized as a poor immunotherapy responder (208).

In some embodiments, the passenger genes can be identified in large-scale cancer genome analysis according to a metric referred to herein as a Passenger Gene Index (PGI) (212). In some embodiments, the PGI is based on genetic mutation rates (GMR) of the passenger genes being highly correlated with overall cancer mutation frequencies, also referred to as tumor mutational burden (214). Identified passenger genes are enriched for families known for excessive passenger mutations, such as extremely large proteins and genes with low expression level or late DNA replication time. More passenger gene mutations will accumulate in cancer samples/types with higher mutations rates, and the average number of mutated genes per sample in each cancer type can be a surrogate for likelihood of passenger mutations in that cancer type. Thus, PGI can be defined, for each gene, $X_i$, as a correlation between percentage sample with gene $X_i$ mutation and average number of mutated gene per sample in each cancer type. A higher PGI score indicates that a particular gene is more likely to acquire somatic mutations in the cancer types with higher overall mutation frequency. Genes with a low PGI show a weak association between the two variables (e.g., and can be observed in canonical cancer driver genes such as TP53, PIK3CA and KRAS). Genes ranked at the top of the PGI are enriched for gene families known for excessive passenger mutations, e.g., extremely large proteins (>4,000 amino acids), genes spanning large genomic loci (>1 Mb), genes with low expression level, genes with late DNA replication time, and the like. A cumulative distribution function (CDF) of these gene families show sharp uptrend at PGI>0.7, while the genes in Catalogue of Somatic Mutations in Cancer (COSMIC) Cancer Gene Census (CGC) are more uniformly distributed. Two-sample Kolmogorov-Smirnov tests show significant difference in the rank distribution of passenger gene families as compared to that of CGC genes ($p=8.3\times10^{-19}$ for large proteins; $p=2.9\times10^{-12}$ for genomic locus >1 Mb; $p=6.4\times10^{-35}$ for low expression; $p=2.7\times10^{-29}$ for late replication). Similar results are obtained when samples are grouped by mutation rate (instead of cancer type) for computing PGI.

The top passenger genes, based on highest PGI, can be agnostic to tumor type or specific for each tumor type. Thus, in some instances, the top passenger genes can be used generically, regardless of tumor type. Although these top passenger genes do not change regardless of tumor type, the top passenger genes can change over time due to accessibility of additional samples. In some instances, the top passenger genes can vary between tumor types. In some instances, the top passenger genes can be identical between tumor types. Furthermore, if the top passenger genes are identical between tumor types, the ranking within that top passenger gene list can vary. For example, the top 50 passenger genes for breast cancer can be identical to the top 50 passenger genes for lung cancer however the number one passenger gene (meaning highest PGI) for breast cancer can be the number five passenger gene for lung cancer. In some instances, the top 50 passenger genes of one tumor type can comprise 1, 5, 10, 15, 20, 25, 30, 35, 40, 45, 50, up to 100 percent of the top 50 passenger genes of a second tumor type. Depending on what range of PGI is included, a list of top 25, 50, 100, 150, 200, 250, 300, 350, 400, 450, 500, or even 2000 plus passenger genes can be included on a top passenger gene list. In some instances, the top passenger genes do not vary among patients. All patients can use the same passenger gene list and each patient will have a different TMB score.

In an embodiment, illustrated in FIG. 3, a method (300) is disclosed comprising receiving genetic sequence data (310). The genetic sequence data can comprise a plurality of genes and can be derived from a plurality of biological samples collected from subjects having a plurality of disease types. The plurality of disease types can comprise cancers.

In some embodiments, the method (300) can identify a plurality of mutated genes for each of the plurality of biological samples (320), wherein each of the mutated genes comprises a genetic sequence having at least one non-synonymous somatic mutation.

In some embodiments, the method (300) can determine a tumor mutational burden for each biological sample based on a number of mutated genes in each biological sample (330). In a preferred embodiment, determining the tumor mutational burden for each biological sample based on a number of mutated genes in each biological sample can comprise adding a number of mutated genes in each patient sample.

The method (300) can identify a mutation in a gene (passenger or driver), for example, by aligning the mutated sequences with wild type or reference sequences. Various programs and alignment algorithms are described in: Smith and Waterman (1981) Adv. Appl. Math. 2:482; Needleman and Wunsch (1970) J. Mol. Biol. 48:443; Pearson and Lipman (1988) Proc. Natl. Acad. Sci. USA 85:2444; Higgins and Sharp (1988) Gene 73:237-244; Higgins and Sharp (1989) CABIOS 5:151-153; Corpet et al. (1988) Nucl. Acids Res. 16:10881-90; Huang et al. (1992) *Computer Appl. in the Biosci.* 8:155-65; and Pearson et al. (1994). *Meth. Mol. Biol.* 24:307-31, which are herein incorporated by reference. Altschul et al. (1994) *Nature Genet.* 6:119-29 (herein incorporated by reference) present a detailed consideration of sequence alignment methods and homology calculations.

The NCBI Basic Local Alignment Search Tool (BLAST) (Altschul et al. 1990) is available from several sources, including the National Center for Biological Information (NCBI, Bethesda, Md.) and on the Internet, for use in connection with the sequence analysis programs blastp, blastn, blastx, tblastn and tblastx. It can be accessed at <//www.ncbi.nlmn.ih.gov/BLAST/>. A description of how to determine sequence identity using this program is available at <//www.nebi.rlm.nih.gov/BLAST/blast-help.html>.

In some embodiments, for each disease type, the method (300) can determine an average tumor mutational burden of the plurality of mutated genes in the plurality of biological samples based on the determined numbers of mutated genes in each biological sample (340). In a preferred embodiment, determining the average tumor mutational burden of the plurality of mutated genes in the plurality of biological samples based on the determined numbers of mutated genes in each biological sample can comprise adding the tumor mutational burden from each patient sample and dividing by a number of patient samples for each disease type.

In some embodiments, for each mutated gene and each disease type, the method (300) can determine a fraction of biological samples comprising the mutated gene (350).

In some embodiments, for each mutated gene, the method (300) can determine a correlation coefficient between the average tumor mutational burden and the fraction of biological samples comprising the mutated gene (360).

In some embodiments, the method (300) can determine whether the mutated gene is a passenger gene based on the correlation coefficient (370). A higher correlation coefficient indicates that a particular gene is more likely to acquire somatic mutations in the cancer types with higher overall mutation frequency (e.g., passenger gene), whereas a lower correlation coefficient indicates that a particular gene is less likely to acquire somatic mutations in the cancer types with higher overall mutation frequency (e.g., not a passenger gene).

In an alternate embodiment, the method (300) can further comprise generating a list of the mutated genes identified as passenger genes. In aspect preferred embodiment, the list can represent an immunogenicity profile for the selected disease.

Figure 4:
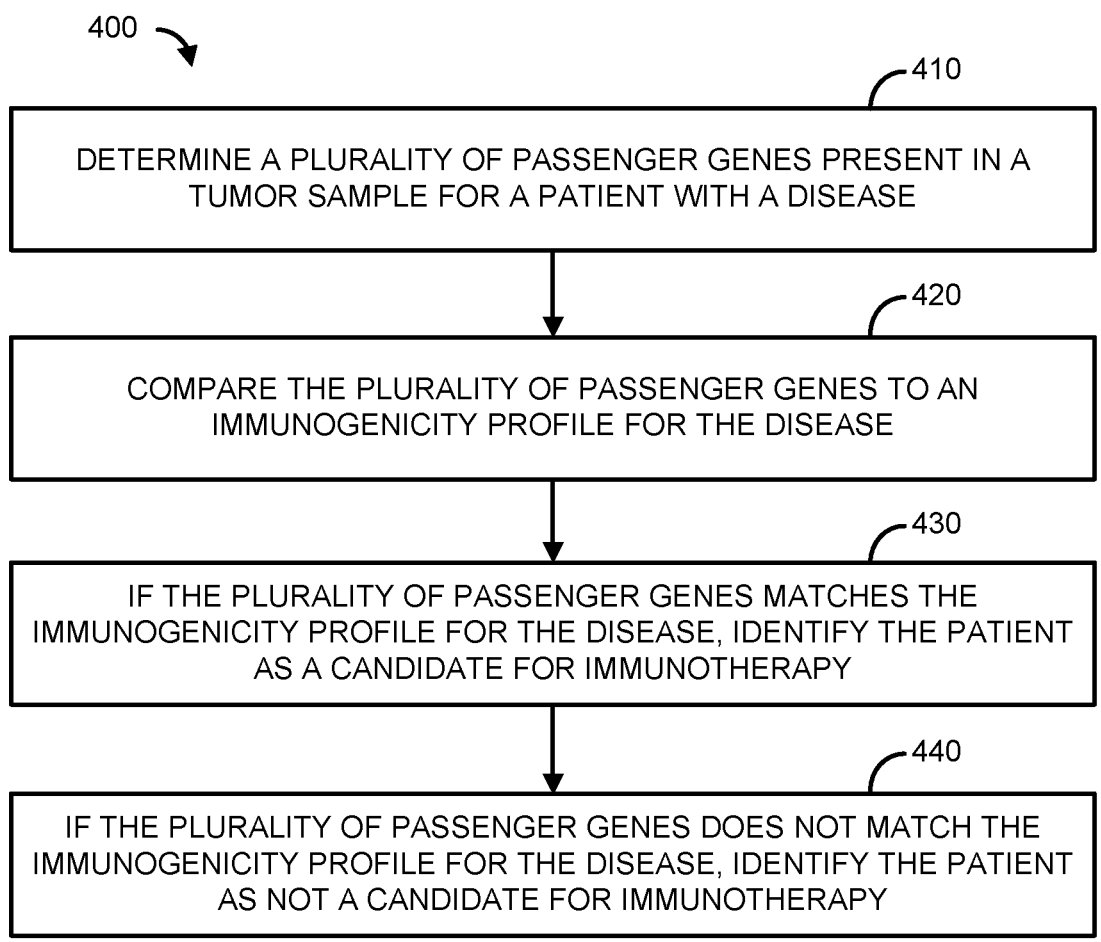
FIG. 4 shows a flowchart illustrating another example method.

In some embodiments, illustrated in FIG. 4, a method for selecting a patient for cancer therapy (400) is disclosed comprising determining a plurality of passenger genes present in a tumor sample for a patient with a disease (410).

In some embodiments, the method (400) can compare the plurality of passenger genes to an immunogenicity profile for the disease (420). In a preferred embodiment, the immunogenicity profile can be generated by performing steps comprising receiving genetic sequence data, wherein the genetic sequence data comprises a plurality of genes and is derived from a plurality of biological samples collected from subjects having a plurality of disease types, identifying a plurality of mutated genes for each of the plurality of biological samples, wherein each of the mutated genes comprises a genetic sequence having at least one non-synonymous somatic mutation, determining a tumor mutational burden for each biological sample based on a number of mutated genes in each biological sample, for each disease type, determining an average tumor mutational burden of the plurality of mutated genes in the plurality of biological samples based on the determined numbers of mutated genes in each biological sample, for each mutated gene and each disease type, determining a fraction of biological samples comprising the mutated gene, for each mutated gene, determining a correlation coefficient between the average tumor mutational burden and the fraction of biological samples comprising the mutated gene. In some embodiments, the mutated gene can be determined to be a passenger gene based on the correlation coefficient. A higher correlation coefficient indicates that a particular gene is more likely to acquire somatic mutations in the cancer types with higher overall mutation frequency (e.g., passenger gene), whereas a lower correlation coefficient indicates that a particular gene is less likely to acquire somatic mutations in the cancer types with higher overall mutation frequency (e.g., not a passenger gene).

A list of the mutated genes identified as passenger genes can be generated, wherein the list represents the immunogenicity profile for the selected disease. In a preferred embodiment, determining the tumor mutational burden for each biological sample based on a number of mutated genes in each biological sample can comprise adding a number of mutated genes in each patient sample. In a preferred embodiment, determining the average tumor mutational burden of the plurality of mutated genes in the plurality of biological samples based on the determined numbers of mutated genes in each biological sample can comprise adding the tumor mutational burden from each patient sample and dividing by a number of patient samples for each disease type.

In some embodiments, PGI can be used to identify passenger genes for particular cancers and then using TMB of the passenger genes, patients can be identified that are responders to specific treatments, such as, but not limited to, anti-PD-1 or a combination of anti-PD-1 and another cancer therapeutic. TMB of passenger genes can also be used to identify responders to other cancer antibody treatments, such as, but not limited to, anti-CD20 (chronic lyphocytic leukemia), anti-HER2 (breast cancer), anti-EGFR (colorectal and head and neck cancer), anti-CD19 (B cell cancers), and anti-CD20 (lymphoma) or combinations of an antibody treatment and another cancer therapeutic. In some embodiments, the other cancer therapeutic can be chemotherapy, an immunomodulatory agent (e.g., a second antibody, a cytokine), radiation, or surgery.

In some embodiments, comparing the plurality of passenger genes to an immunogenicity profile for the disease can comprise determining a number of matches between the plurality of mutated genes and a list of mutated genes in the profile.

In some embodiments, if the plurality of passenger genes matches the immunogenicity profile for the disease (430), the method (400) can identify the patient as a candidate for immunotherapy.

In some embodiments, if the plurality of passenger genes does not match the immunogenicity profile for the disease (440), the method (400) can identify the patient as not a candidate for immunotherapy.

In an alternate embodiment, the method (400) can further comprise enrolling the patient in an immunotherapy program if the patient was identified as a candidate for immunotherapy.

The disclosed immunotherapies can be used in combination with other antibody or antigen-binding fragments thereof as well as other anti-cancer therapies. Combination therapies can be administered simultaneously or sequentially. In some embodiments, two or more therapies can be formulated together with a pharmaceutically acceptable carrier resulting in a pharmaceutical composition. In some embodiments, two or more therapies are formulated individually with a pharmaceutically acceptable carrier resulting in two or more pharmaceutical compositions. By "pharmaceutically acceptable" is meant a material or carrier that would be selected to minimize any degradation of the active ingredient and to minimize any adverse side effects in the subject, as would be well known to one of skill in the art. Examples of carriers include dimyristoylphosphatidyl (DMPC), phosphate buffered saline or a multivesicular liposome. For example, PG:PC:Cholesterol:peptide or PC:peptide can be used as carriers in this invention. Other suitable pharmaceutically acceptable carriers and their formulations are described in Remington: The Science and Practice of Pharmacy (19th ed.) ed. A. R. Gennaro, Mack Publishing Company, Easton, PA 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of composition being administered. These most typically would be standard carriers for administration of drugs to humans, including solutions such as sterile water, saline, and buffered solutions at physiological pH.

Pharmaceutical compositions can also include carriers, thickeners, diluents, buffers, preservatives and the like, as long as the intended activity of the immunotherapy of the invention is not compromised. Pharmaceutical compositions may also include one or more active ingredients (in addition to the composition of the invention) such as antimicrobial agents, anti-inflammatory agents, anesthetics, and the like. The pharmaceutical composition may be administered in a number of ways depending on whether local or systemic treatment is desired, and on the area to be treated.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for optical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. Typically, the final injectable form should be sterile and should be effectively fluid for easy syringability. The pharmaceutical compositions should be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, can be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot on, as an ointment.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a disclosed immunotherapy, and/or pharmaceutically acceptable salts thereof, can also be prepared in powder or liquid concentrate form.

The exact dosage and frequency of administration depends on the particular disclosed peptide, a product of a disclosed method of making, a pharmaceutically acceptable salt, solvate, or polymorph thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compositions.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

Figure 10:
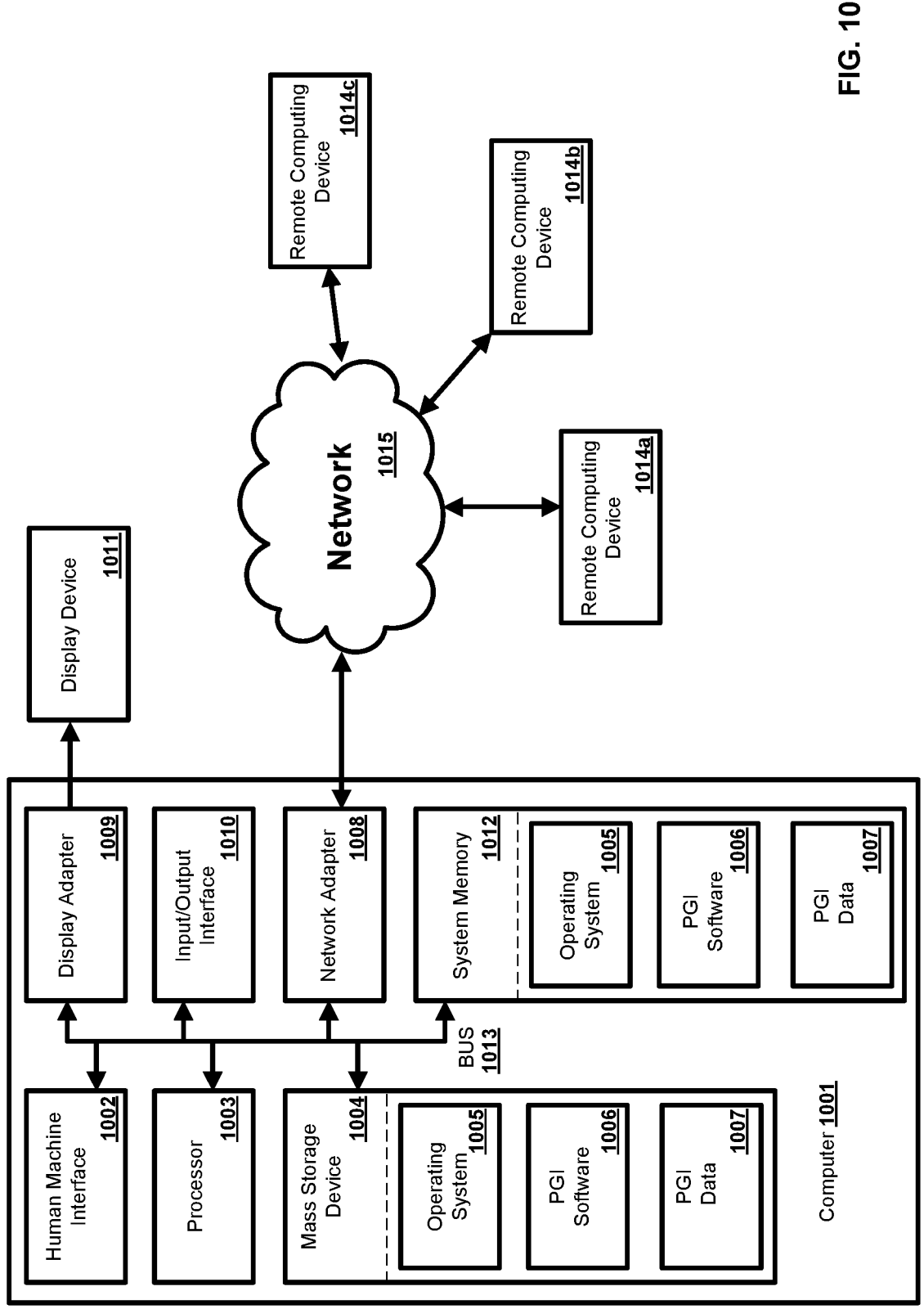
FIG. 10 is a block diagram illustrating an exemplary operating environment for performing the disclosed methods.

In an exemplary embodiment, some or all of the methods and systems can be implemented on one or more computers, such as a computer (1001) as illustrated in FIG. 10 and described below. In some embodiments, the methods and systems disclosed can utilize one or more computers to perform one or more functions in one or more locations. FIG. 10 shows a block diagram illustrating an exemplary operating environment for performing the disclosed methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

In some embodiments, the present methods and systems can be operational with numerous other general purpose or special purpose computing system environments or configurations. Examples of well-known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

In some embodiments, the processing of the disclosed methods and systems can be performed by software components. The disclosed systems and methods can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via a general-purpose computing device in the form of a computer 1001. The components of the computer 1001 can comprise, but are not limited to, one or more processors 1003, a system memory 1012, and a system bus 1013 that couples various system components including the one or more processors 1003 to the system memory 1012. The system can utilize parallel computing.

The system bus 1013 represents one or more of several possible types of bus structures, including a memory bus or memory controller, a peripheral bus, an accelerated graphics port, or local bus using any of a variety of bus architectures. The bus 1013, and all buses specified in this description can also be implemented over a wired or wireless network connection and each of the subsystems, including the one or more processors 1003, a mass storage device 1004, an operating system 1005, PGI software 1006, PGI data 1007, a network adapter 1008, the system memory 1012, an Input/Output Interface 1010, a display adapter 1009, a display device 1011, and a human machine interface 1002, can be contained within one or more remote computing devices 1014*a,b,c* at physically separate locations, connected through buses of this form, in effect implementing a fully distributed system.

The computer 1001 typically comprises a variety of computer readable media. Exemplary readable media can be any available media that is accessible by the computer 1001 and comprises, for example and not meant to be limiting, both volatile and non-volatile media, removable and non-removable media. The system memory 1012 comprises computer readable media in the form of volatile memory, such as random access memory (RAM), and/or non-volatile memory, such as read only memory (ROM). The system memory 1012 typically contains data such as the PGI data 1007 and/or program modules such as the operating system 1005 and the PGI software 1006 that are immediately accessible to and/or are presently operated on by the one or more processors 1003. The PGI data 1007 can comprise read coverage data and/or expected read coverage data.

In some embodiments, the computer 1001 can also comprise other removable/non-removable, volatile/non-volatile computer storage media. By way of example, FIG. 10 illustrates the mass storage device 1004 which can provide non-volatile storage of computer code, computer readable instructions, data structures, program modules, and other data for the computer 1001. For example and not meant to be limiting, the mass storage device 1004 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 1004, including by way of example, the operating system 1005 and the PGI software 1006. Each of the operating system 1005 and the PGI software 1006 (or some combination thereof) can comprise elements of the programming and the PGI software 1006. The PGI data 1007 can also be stored on the mass storage device 1004. The PGI data 1007 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In an alternate embodiment, the user can enter commands and information into the computer 1001 via an input device (not shown). Examples of such input devices comprise, but are not limited to, a keyboard, pointing device (e.g., a "mouse"), a microphone, a joystick, a scanner, tactile input devices such as gloves, and other body coverings, and the like. These and other input devices can be connected to the one or more processors 1003 via the human machine interface 1002 that is coupled to the system bus 1013, but can be connected by other interface and bus structures, such as a parallel port, game port, an IEEE 1394 Port (also known as a Firewire port), a serial port, or a universal serial bus (USB).

In an alternate embodiment, the display device 1011 can also be connected to the system bus 1013 via an interface, such as the display adapter 1009. It is contemplated that the computer 1001 can have more than one display adapter 1009 and the computer 1001 can have more than one display device 1011. For example, a display device can be a monitor, an LCD (Liquid Crystal Display), or a projector. In addition to the display device 1011, other output peripheral devices can comprise components such as speakers (not shown) and a printer (not shown) which can be connected to the computer 1001 via the Input/Output Interface 1010. Any step and/or result of the methods can be output in any form to an output device. Such output can be any form of visual representation, including, but not limited to, textual, graphical, animation, audio, tactile, and the like. The display 1011 and computer 1001 can be part of one device, or separate devices.

The computer 1001 can operate in a networked environment using logical connections to one or more remote computing devices 1014a,b,c. By way of example, a remote computing device can be a personal computer, portable computer, smartphone, a server, a router, a network computer, a peer device or other common network node, and so on. Logical connections between the computer 1001 and a remote computing device 1014a,b,c can be made via a network 1015, such as a local area network (LAN) and/or a general wide area network (WAN). Such network connections can be through the network adapter 1008. The network adapter 1008 can be implemented in both wired and wireless environments. Such networking environments are conventional and commonplace in dwellings, offices, enterprise-wide computer networks, intranets, and the Internet.

For purposes of illustration, application programs and other executable program components such as the operating system 1005 are illustrated herein as discrete blocks, although it is recognized that such programs and components reside at various times in different storage components of the computing device 1001, and are executed by the one or more processors 1003 of the computer. In an aspect, at least a portion of the PGI software 1006 and/or the PGI data 1007 can be stored on and/or executed on one or more of the computing device 1001, the remote computing devices 1014a,b,c, and/or combinations thereof. Thus the PGI software 1006 and/or the PGI data 1007 can be operational within a cloud computing environment whereby access to the PGI software 1006 and/or the PGI data 1007 can be performed over the network 1015 (e.g., the Internet). Moreover, in an aspect the PGI data 1007 can be synchronized across one or more of the computing device 1001, the remote computing devices 1014a,b,c, and/or combinations thereof.

An implementation of the PGI software 1006 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ Artificial Intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

The following examples are provided to describe the disclosure in greater detail. They are intended to illustrate, not to limit, the disclosure.

Example 1

Passenger Gene Index

The method of Passenger Gene Index (PGI) involves all TCGA samples binned by cancer type, and the median number of mutated genes was determined for each bin. Mutations were limited only to nonsilent somatic mutations by comparing solid tumors to the blood derived or solid normal counterparts, with the exception in acute myeloid leukemia where blood derived tumors were compared to the solid tissue normal. Mutation profiles were constructed as a binary matrix such that a bit is set if any locus correspond to the gene harbors a mutation in that patient. PGI is computed for each gene $X_i$, as Pearson correlation between fraction of sample with gene $X_i$ mutation and the median number of mutated gene in each cancer type. Before computing the correlations, an infinitesimal amount of uniformly distributed noise was added to the sample fraction with mutation to avoid issues with all zero entries.

Example 2

Z-Score for Driver and Passenger Gene Tumor Mutational Burden

The method of Z-score for driver/passenger TMB involves the following. To compute z-score for a TMB, background distribution of the TMB was first established using 1000 randomly selected gene sets of equal size. The numbers of mutated driver/passenger gene were then compared to the background distribution to compute the z-score, indicating how many standard deviations the number is from the mean of the background. Driver genes were downloaded from COSMIC Cancer Gene Census on Jan. 22, 2015, and passenger genes were defined as top n genes ranked by PGI derived from TCGA data.

Example 3

Passenger Gene Tumor Mutational Burden and Immunotherapy Responsiveness

Figure 5:
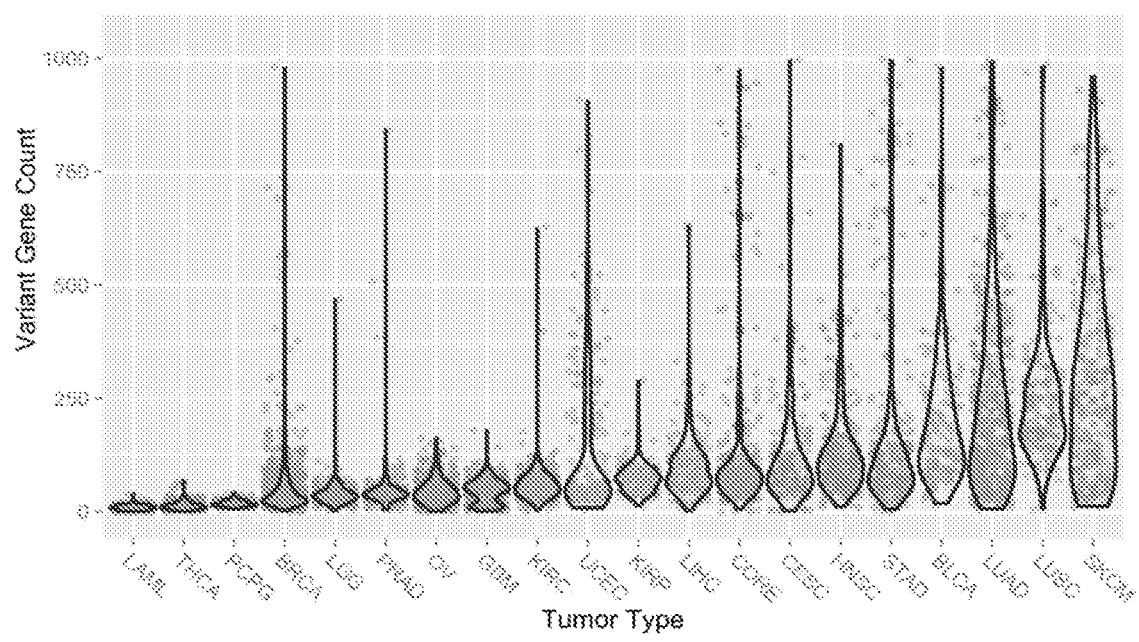
FIG. 5 illustrates an overview of passenger gene characteristics.

To compute Passenger Gene Index (PGI), a list was compiled of nonsilent somatic mutations from 6,685 samples across 20 TCGA tumor types. Somatic mutations were determined by comparing tumor genome to that of the germ line, e.g. blood derived normal sample from the same patient. The median number of altered genes per sample ranged from 9 in acute myeloid leukemia to 289 in skin cutaneous melanoma, representing over 32-fold difference between the lowest and the highest mutation rate cancers (FIG. 5). This is consistent with previous observations that skin and lung cancer samples have the highest mutation rates, due to the exposure to environmental mutagens. FIG. 5 shows the number of nonsilent somatic mutations per sample in 6,685 TCGA cancer exomes.

The 20 cancer types included in this study are bladder urothelial carcinoma (BLCA), breast invasive carcinoma (BRCA), cervical squamous cell carcinoma and endocervical adenocarcinoma (CESC), colon/rectum adenocarcinoma (CORE), glioblastoma multiforme (GBM), head and neck squamous cell carcinoma (HNSC), kidney renal clear cell carcinoma (KIRC), kidney renal papillary cell carcinoma (KIRP), acute myeloid leukemia (LAML), liver hepatocellular carcinoma (LIHC), brain lower grade glioma (LGG), lung adenocarcinoma (LUAD), lung squamous cell carcinoma (LUSC), ovarian serous cystadenocarcinoma (OV), pheochromocytoma and paraganglioma (PCPG), prostate adenocarcinoma (PRAD), skin cutaneous melanoma (SKCM), stomach adenocarcinoma (STAD), thyroid carcinoma (THCA), and uterine corpus endometrioid carcinoma (UCEC).

Figure 6:
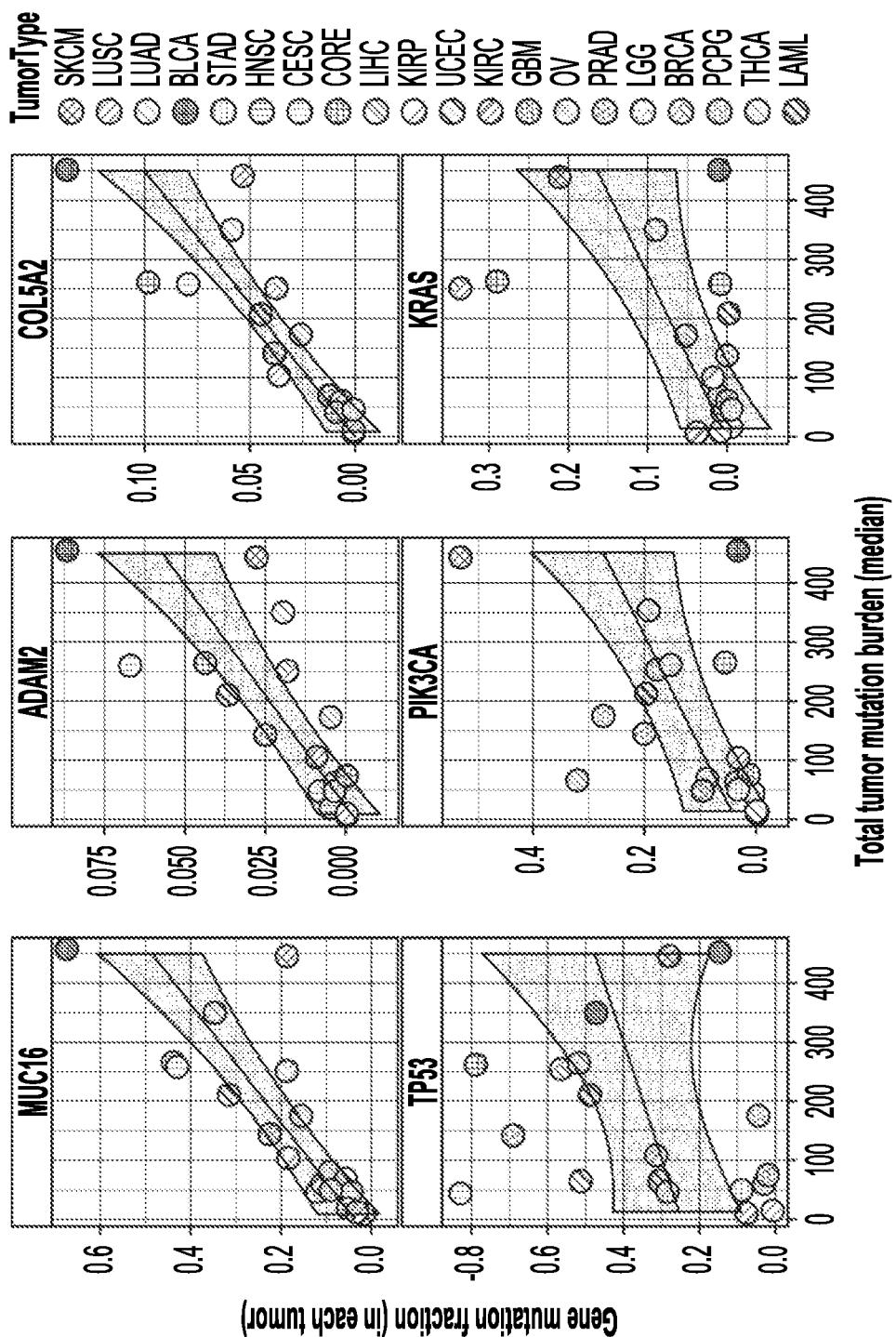
FIG. 6 shows scatter plots for the fraction of patients with the gene variant (y-axis) and average number of total mutated gene (x-axis) in each cancer type.

It was hypothesized that more passenger mutations will accumulate in cancer types with higher overall mutation rates, and the average number of altered genes per sample in each cancer type can be a surrogate for likelihood of passenger mutations in that cancer type. PGI was defined for each gene, $X_i$, as a correlation between percentage sample with gene $X_i$ variant and average number of altered gene per sample in each cancer type. A higher PGI score indicated that a particular gene is more likely to acquire somatic mutations in the cancer types with higher overall mutation frequency. Passenger genes show strong linear relationship of the two variables, while weak associations were observed in canonical cancer genes such as TP53, PIK3CA and KRAS (FIG. 6). FIG. 6 illustrates scatter plots for a fraction of patients with the gene variant (y-axis) and average number of total mutated gene (x-axis) in each cancer type. The top row shows a strong linear relationship in the top passenger genes (MUC16 r=0.979; ADAM2 r=0.972; COL5A2 r=0.968), and the bottom row shows weak association of the 2 variables in canonical cancer genes (TP53 r=0.301; PIK3CA r=0.120; KRAS r=0.222).

Figure 7:
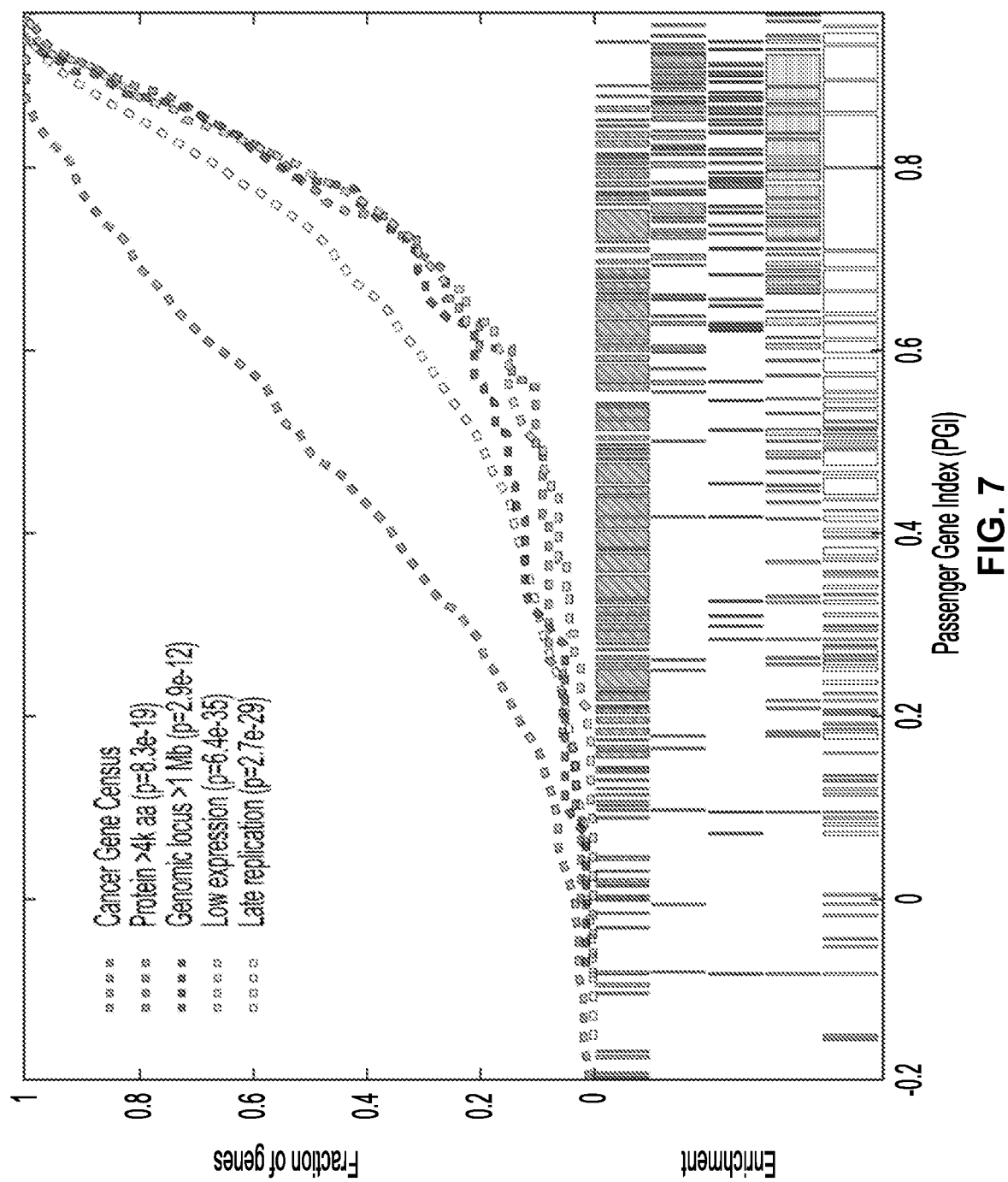
FIG. 7 shows enrichment along the Passenger Gene Index (PGI) scale for cancer driver genes and various other gene groups.

Genes ranked at the top of the PGI are enriched for gene families known for excessive passenger mutations, e.g., extremely large proteins (>4,000 amino acids), genes spanning large genomic loci (>1 Mb), genes with low expression level, and genes with late DNA replication time. A cumulative distribution function (CDF) of these gene families show a sharp uptrend at PGI>0.7, while the driver genes in Catalogue of Somatic Mutations in Cancer (COSMIC) Cancer Gene Census (CGC) are more uniformly distributed (FIG. 7). FIG. 7 illustrates enrichment along the PGI scale for cancer driver genes and various other gene groups. The dotted lines (upper) show the fraction of genes at different PGI, and the vertical lines (lower) indicate the rank of individual genes. A two-sample Kolmogorov-Smirnov test was used to examine the difference in gene distribution for each group, as compared to the cancer genes distribution. The two-sample Kolmogorov-Smirnov tests showed significant difference in the rank distribution of passenger gene families as compared to that of CGC genes ($p=8.3\times10^{-19}$ for large proteins; $p=2.9\times10^{-12}$ for genomic locus >1 Mb; $p=6.4\times10^{-35}$ for low expression; $p=2.7\times10^{-29}$ for late replication). Similar results were observed when samples were grouped by mutation rate (instead of cancer type) for computing PGI. While some CGC genes also possess high PGI score, they are not validated for their top altered TCGA cancer types. For instance, KDR (kinase insert domain receptor) has the highest rate of mutation in melanoma (14% in SKCM) but KDR is only known for its causal implication in non-small-cell lung carcinoma and angiosarcoma. Similarly, we did not see any validated cases in the highest altered cancer type for the top 30 CGC genes. In contrast, 16 out of the 30 CGC driver genes with the lowest PGI are validated in their corresponding altered cancer type (FIG. 8). FIG. 8 shows that low PGI CGC genes are more likely to be validated in the altered cancer type. FIG. 8 shows the highest (left) and lowest (right) PGI CGC genes, and their corresponding cancer type with the highest percentage (>2%) of mutated sample. The acronyms marked with an asterisk are the cancer type validated by CGC for the gene. None of the cancer in the highest PGI CGC genes is validated, and 16/30 cancer types in the lowest PGI CGC genes are validated.

Figure 9A:
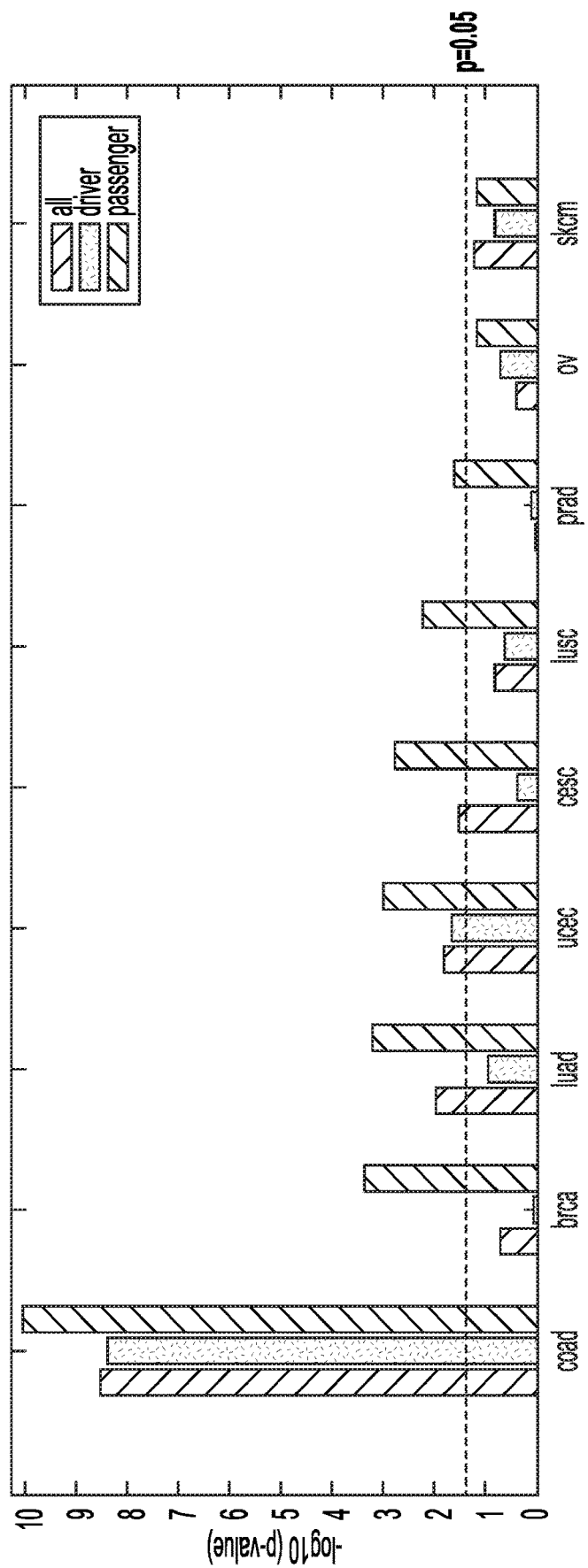
FIGS. 9A-C are graphical representations of a) local immune cytolytic activities, b) TCR read count and c) clinical outcome of patient cohorts.

PGI was applied as a metric to select passenger genes and use the tumor mutational burden (TMB) of the selected passenger genes to stratify patient cohort that is more likely to respond to immunotherapy. To demonstrate this approach, local immune cytolytic activities and T-cell receptor (TCR) read count were used as the surrogate for immunogenicity, and tested if there is any immunogenicity difference between high and low TMB patients in TCGA data. For each patient, the TMB was computed in 3 different approaches, namely (i) conventional total TMB, (ii) TMB by driver genes, and (iii) TMB by passenger genes. To quantify the cytolytic activities, we adopted a simple RNA-based metric that based on gene expression level of two key cytolytic effectors, granzyme A (GZMA) and perforin (PRF1). The cytolytic activities were found significantly different ($p<0.05$ by Mann-Whitney U test) between high and low passenger TMB patients in 7 different cancer types (colon adenocarcinoma, $p<4.6\times10^{-11}$; breast invasive carcinoma, $p<5.0\times10^{-4}$; lung adenocarcinoma, $p<7.7\times10^{-4}$; uterine corpus endometrioid carcinoma, $p<9.9\times10^{-4}$; cervical squamous cell carcinoma, $p<2.2\times10^{-3}$; lung squamous cell carcinoma, $p<5.7\times10^{-3}$; prostate adenocarcinoma, $p<2.1\times10^{-2}$), and the differences are more significant as compared to those using total TMB and driver gene TMB in the corresponding cancer types (FIG. 9A).

Figure 9B:
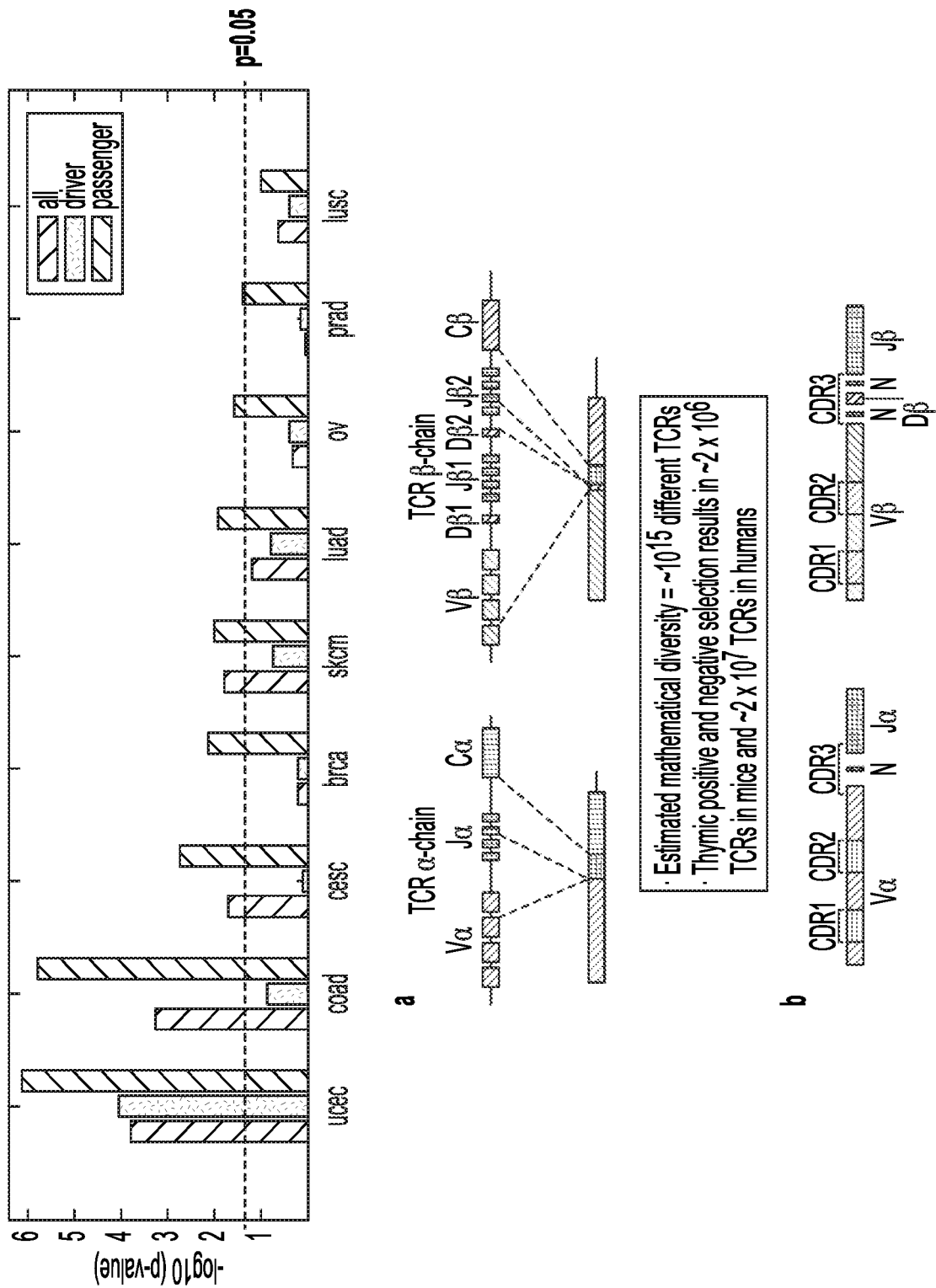

TCR is responsible for the recognition of peptide-MHC complexes and its diversity is directly associated to the number of foreign or mutated proteins, e.g. neo-antigens from cancer cells. TCRβ repertoire analysis was performed using TCGA RNA-seq data, and compared TCRβ read count between high and low passenger TMB patients. As shown in FIG. 9B, the detected number of TCRβ read count were significantly different between high and low passenger TMB patients in 8 different cancer types (uterine corpus endometrioid carcinoma, $p<3.2\times10^{-6}$; colon adenocarcinoma, $p<4.5\times10^{-6}$; cervical squamous cell carcinoma, $p<2.4\times10^{-3}$; breast invasive carcinoma, $p<7.3\times10^{-3}$; skin cutaneous melanoma, $p<9.2\times10^{-3}$; lung adenocarcinoma, $p<1.5\times10^{-2}$;

ovarian serous cystadenocarcinoma, $p<2.7\times10^{-2}$; prostate adenocarcinoma, $p<3.8\times10^{-2}$). In agreement with the observation in cytolytic activities, the TCRβ differences are more significant between the groups segregated by passenger TMB, as compared to those using total TMB and driver TMB.

Figure 9C:
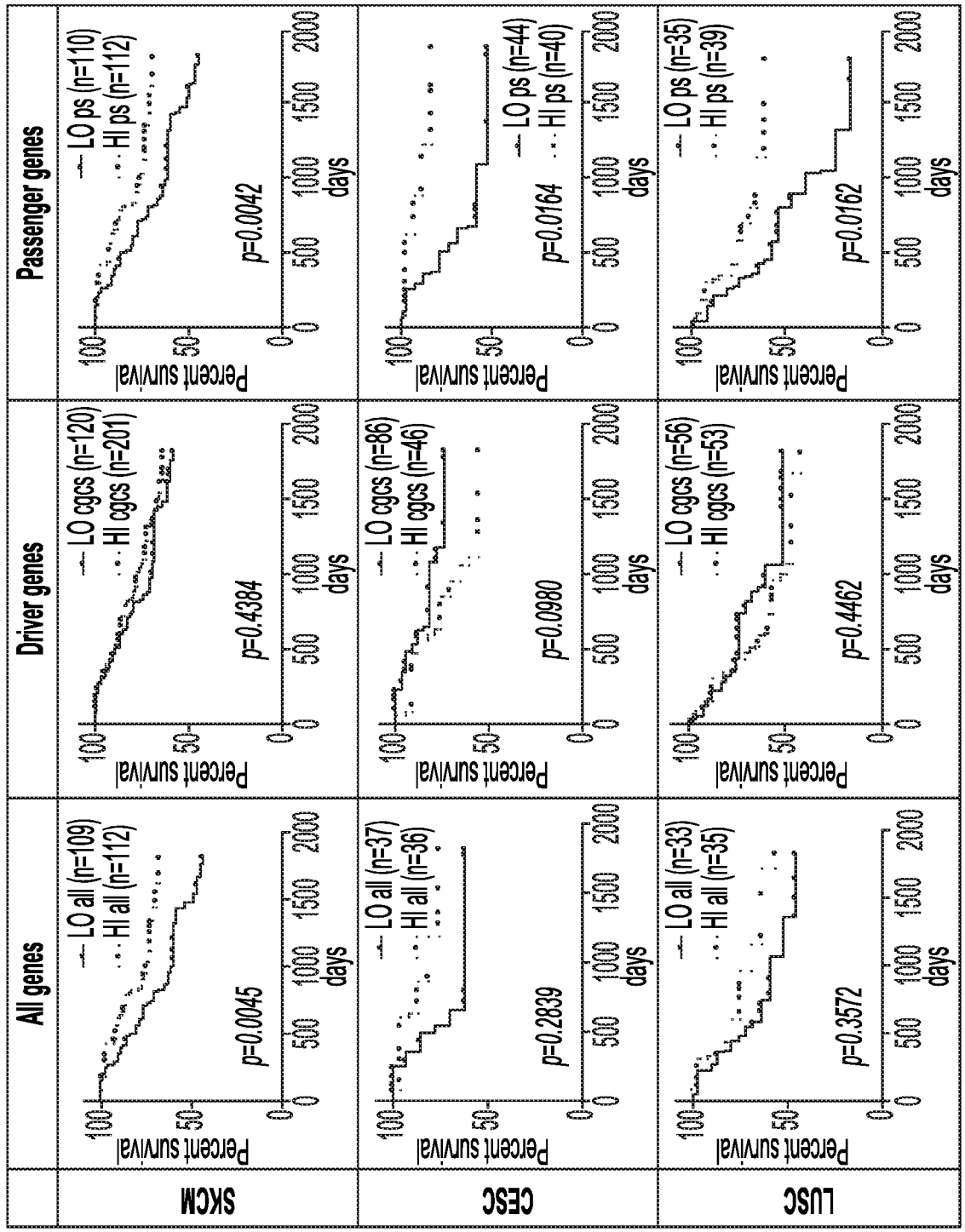

Finally, tests were done to see if there is any survival advantage associated with TMB in TCGA data. In cervical and lung squamous cell carcinoma (CESC and LUSC), although not statistically significant, total TMB shows positive association trend with better survival outcome, while driver TMB is associated with worse prognosis (FIG. 9C). FIG. 9C illustrates clinical outcome of patient cohorts segregated by mutation load of: (i) all genes, (ii) driver genes, and (iii) passenger genes in skin cutaneous melanoma (SKCM), cervical squamous cell carcinoma (CESC) and endocervical adenocarcinoma, and lung squamous cell carcinoma (LUSC) yield significant survival differences only in patient cohorts segregated by passenger TMB but not total/driver TMB. SKCM shows significant difference in patient survival between high and low total/passenger TMB groups.

Only when the passenger TMB was used, the difference of the survival outcome between the high and low TMB patient groups was statistically significant in both CESC and LUSC. In skin cutaneous melanoma (SKCM), patient stratification using passenger and total TMB both show similar significant separation in survival curves, indicating that there is very little or no driver gene mutation that strongly impact the immunogenicity suppression in melanoma. Using an independent dataset of CTLA-4 blockade in metastatic melanoma, 110 patients were segregated into two groups of equal size by mutation burden. Stratification using TMB of 200 passenger genes improved the clinical benefit rate of the selected patient group from a baseline of 24.55% to 36.36% (Fisher's Exact Test p=0.0035). Patient stratification using the total TMB yields the same improvement in clinical benefit, further corroborate the observations in cytolytic activities, TCR detection, and survival advantage for melanoma using TCGA data.

Figure 11:
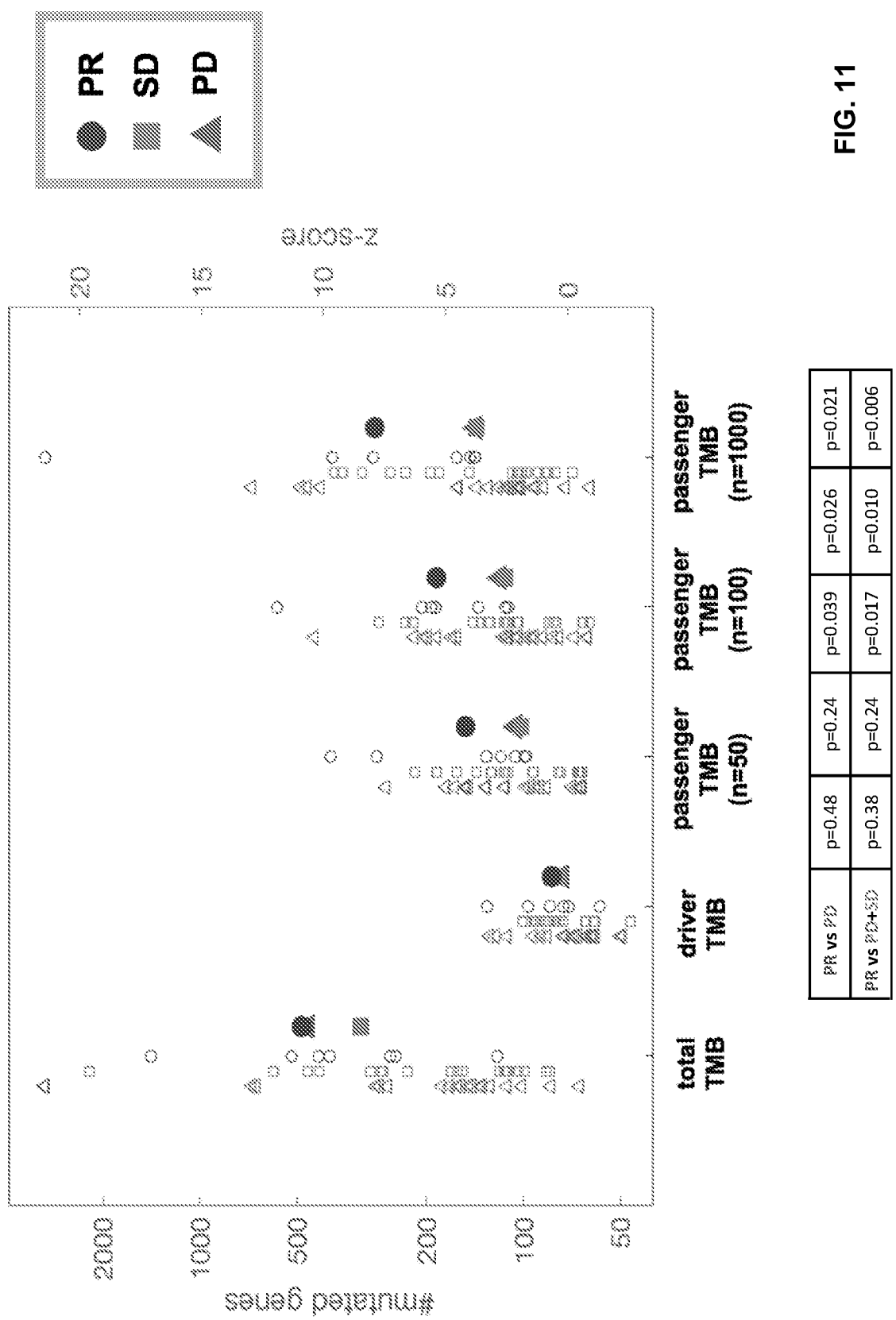
FIG. 11 is TMB of the patient cohort in phase 1 clinical study.

FIG. 11 shows the TMB of the patient cohort in an anti-PD1 phase 1 clinical study. Closed circles, closed squares, and closed triangles indicate patients with partial response (PR), stable disease (SD), and progressive disease (PD) respectively. Hollow shapes show data for individual patients, and solid shapes show the average in each PR/SD/PD groups. Total TMBs are shown as the total number of mutated genes (left y-axis) and driver/passenger TMBs are shown in z-score (right y-axis). Both PR-vs-PD and PR-vs-PD+SD show statistically significant differences in the passenger TMB, invariantly of the number of top (50/100/1000) passenger genes used. PR group does not yield significant difference in the total or driver TMB.

Example 4

Passenger Gene Tumor Mutational Burden and Clinical Immunotherapy Response

To evaluate the clinical response of various malignancies to immunotherapy, the somatic mutation data from phase 1 study of a monoclonal human antibody to PD-1 (Programmed Death-1) were used, as single therapy and in combination with other anti-cancer therapies. In total, clinical response data are available from 74 patients with advanced malignancies (n=8 with partial response, PR; n=29 with stable disease, SD; n=37 with progressive disease, PD). Total TMB is denoted as the total number of mutated genes, and driver/passenger TMBs are represented in z-scores in order to normalize for the total TMB of the patients. Z-scores are computed by comparing the number of mutated driver/passenger genes to the background distribution using randomly selected genes of equal size. Higher z-scores indicate higher mutation burden in the selected driver/passenger gene sets despite the total TMB background. The total TMB and z-score of driver TMB do not differentiate PR from other patient groups, while the passenger TMB z-scores in PR patients are significantly higher as compared to those in PD or PD+SD patient groups. Results are consistent in TMBs computed using top 50, 100, 500 (FIG. 12) and 1000 passenger genes.

I claim:

1. A method of treating a cancer patient with an antibody that binds to LAG3, comprising administering the antibody that binds to LAG3 to the cancer patient, whereby the cancer patient has been determined to have a tumor having a total passenger gene mutational burden that is greater than a background mutational burden of the tumor.

2. The method according to claim 1, wherein the background mutational burden is determined based on randomly selected genes of the tumor, and wherein a number of the randomly selected genes is equal to a number of passenger genes used to determine the total passenger gene mutational burden.

3. The method according to claim 1, wherein the total passenger gene mutational burden is determined based on one or more passenger genes having a genetic mutation rate that is highly correlated with overall tumor mutation frequencies.

4. The method according to claim 1, wherein the cancer comprises a skin cancer, a lung cancer, or a blood-derived cancer.

5. The method according to claim 4, wherein the skin cancer comprises melanoma or cutaneous squamous cell cancer.

6. The method according to claim 4, wherein the lung cancer comprises lung adenocarcinoma, lung squamous cell carcinoma, or non-small cell lung carcinoma.

7. The method according to claim 4, wherein the blood-derived cancer comprises leukemia or acute myeloid leukemia.

8. The method according to claim 1, wherein the cancer comprises melanoma.

9. The method according to claim 1, wherein the cancer comprises non-small cell lung carcinoma.

10. The method according to claim 1, wherein the antibody that binds to LAG3 comprises a heavy chain variable region (HCVR) comprising the amino acid sequence of SEQ ID NO: 93.

11. The method according to claim 10, wherein the cancer comprises a skin cancer, a lung cancer, or a blood-derived cancer.

12. The method according to claim 11, wherein the skin cancer comprises melanoma or cutaneous squamous cell cancer.

13. The method according to claim 11, wherein the lung cancer comprises lung adenocarcinoma, lung squamous cell carcinoma, or non-small cell lung carcinoma.

14. The method according to claim 11, wherein the blood-derived cancer comprises leukemia or acute myeloid leukemia.

15. The method according to claim 10, wherein the cancer comprises melanoma.

16. The method according to claim 10, wherein the cancer comprises non-small cell lung carcinoma.

17. The method according to claim 1, wherein the passenger gene mutational burden is determined to be greater than the background mutational burden by:
establishing the total passenger gene mutational burden of the tumor;
generating the background mutational burden; and
normalizing the total passenger gene mutational burden against the background mutational burden.

18. The method according to claim 1, the method further comprising administering an antibody that binds to PD1 to the cancer patient.

19. The method according to claim 18, wherein the cancer comprises a skin cancer, a lung cancer, or a blood-derived cancer.

20. The method according to claim 19, wherein the skin cancer comprises melanoma or cutaneous squamous cell cancer.

21. The method according to claim 19, wherein the lung cancer comprises lung adenocarcinoma, lung squamous cell carcinoma, or non-small cell lung carcinoma.

22. The method according to claim 19, wherein the blood-derived cancer comprises leukemia or acute myeloid leukemia.

23. The method according to claim 18, wherein the cancer comprises melanoma.

24. The method according to claim 18, wherein the cancer comprises non-small cell lung carcinoma.

25. The method according to claim 18, wherein the antibody that binds to PD1 comprises an HCVR comprising the amino acid sequence of SEQ ID NO: 21.

26. The method according to claim 25, wherein the cancer comprises a skin cancer, a lung cancer, or a blood-derived cancer.

27. The method according to claim 26, wherein the skin cancer comprises melanoma or cutaneous squamous cell cancer.

28. The method according to claim 26, wherein the lung cancer comprises lung adenocarcinoma, lung squamous cell carcinoma, or non-small cell lung carcinoma.

29. The method according to claim 26, wherein the blood-derived cancer comprises leukemia or acute myeloid leukemia.

30. The method according to claim 25, wherein the cancer comprises melanoma.

31. The method according to claim 25, wherein the cancer comprises non-small cell lung carcinoma.

32. The method according to claim 18, wherein the antibody that binds to PD1 comprises cemiplimab.

33. The method according to claim 32, wherein the cancer comprises a skin cancer, a lung cancer, or a blood-derived cancer.

34. The method according to claim 33, wherein the skin cancer comprises melanoma or cutaneous squamous cell cancer.

35. The method according to claim 33, wherein the lung cancer comprises lung adenocarcinoma, lung squamous cell carcinoma, or non-small cell lung carcinoma.

36. The method according to claim 33, wherein the blood-derived cancer comprises leukemia or acute myeloid leukemia.

37. The method according to claim 32, wherein the cancer comprises melanoma.

38. The method according to claim 32, wherein the cancer comprises non-small cell lung carcinoma.

39. The method according to claim 1, wherein the antibody that binds to LAG3 comprises a light chain variable region (LCVR) comprising the amino acid sequence of SEQ ID NO: 94.

40. The method according to claim 39, wherein the cancer comprises a skin cancer, a lung cancer, or a blood-derived cancer.

41. The method according to claim 40, wherein the skin cancer comprises melanoma or cutaneous squamous cell cancer.

42. The method according to claim 40, wherein the lung cancer comprises lung adenocarcinoma, lung squamous cell carcinoma, or non-small cell lung carcinoma.

43. The method according to claim 40, wherein the blood-derived cancer comprises leukemia or acute myeloid leukemia.

44. The method according to claim 39, wherein the cancer comprises melanoma.

45. The method according to claim 39, wherein the cancer comprises non-small cell lung carcinoma.

\* \* \* \* \*

SEQUENCE LISTING

```
Sequence total quantity: 217
SEQ ID NO: 1              moltype = AA  length = 121
FEATURE                   Location/Qualifiers
REGION                    1..121
                          note = synthetic construct; antigen binding domain
source                    1..121
                          mol_type = protein
                          organism = synthetic construct
SEQUENCE: 1
EVQLLESGGG LVQPGGSLRL SCSASGFTFS SYTMNWVRQA PGKGLEWVSG ISDTGGNTYY   60
TDSVKGRFTV SRDNSKNTLS LQMNSLRAED TAVYYCAKDQ GGSYPYYFHY WGQGSLVTVS  120
S                                                                 121

SEQ ID NO: 2              moltype = AA  length = 108
FEATURE                   Location/Qualifiers
REGION                    1..108
                          note = synthetic construct; antigen binding domain
source                    1..108
                          mol_type = protein
                          organism = synthetic construct
SEQUENCE: 2
DIQMTQSPSS LSASVGDRVT ITCRASQSIS SYLIWYQQKP GTAPKFLIYA ASSLQSGVPS   60
RFSGCGSGTD FTLTISSLQP EDFATYYCQQ SYSTPPITFG QGTRLEIK               108

SEQ ID NO: 3              moltype = AA  length = 122
FEATURE                   Location/Qualifiers
REGION                    1..122
                          note = synthetic construct; antigen binding domain
```

```
source                  1..122
                        mol_type = protein
                        organism = synthetic construct
SEQUENCE: 3
EVQLVESGGG LVQPGGSLRL SCAASGFTVS NNYMSWVRQA PGKGLEWVSV IYSGGFTYYT    60
DSVKGRFTIS RHNSKNTLYL QMNSLRAEDT AVYYCARYYY DTSDYWTFFD YWGQGTLVTV   120
SS                                                                  122

SEQ ID NO: 4            moltype = AA   length = 107
FEATURE                 Location/Qualifiers
REGION                  1..107
                        note = synthetic construct; antigen binding domain
source                  1..107
                        mol_type = protein
                        organism = synthetic construct
SEQUENCE: 4
EIVMTQSPAT LSVSPGERAT LSCRASQSVS SNLAWYQQKP GQAPRLLIYG ASTRATGIPA    60
RFSGSGSGTE FTLTISSLQS GDFAVYYCQQ YNNWPLTFGG GTKVEIN                 107

SEQ ID NO: 5            moltype = AA   length = 122
FEATURE                 Location/Qualifiers
REGION                  1..122
                        note = synthetic construct; antigen binding domain
source                  1..122
                        mol_type = protein
                        organism = synthetic construct
SEQUENCE: 5
EVQLVESGGG LVQPGGSLRL SCAASGFTVS NNYMSWVRQA PGKGLEWVSV IYSGGFTYYT    60
DSVKGRFTIS RHNSKNTLYL QMNSLRAEDT AVYYCARYYY DTSDYWTFFD YWGQGTLVTV   120
SS                                                                  122

SEQ ID NO: 6            moltype = AA   length = 107
FEATURE                 Location/Qualifiers
REGION                  1..107
                        note = synthetic construct; antigen binding domain
source                  1..107
                        mol_type = protein
                        organism = synthetic construct
SEQUENCE: 6
EIVMTQSPAT LSVSPGERAT LSCRASQSVS SNLAWYQQKP GQAPRLLIYG ASTRATGIPA    60
RFSGSGSGTE FTLTISSLQS GDFAVYYCQQ YNNWPLTFGG GTKVEIN                 107

SEQ ID NO: 7            moltype = AA   length = 119
FEATURE                 Location/Qualifiers
REGION                  1..119
                        note = synthetic construct; antigen binding domain
source                  1..119
                        mol_type = protein
                        organism = synthetic construct
SEQUENCE: 7
QVQLVESGGG VVQSGRSLRL SCAASGFTFS SYGMHWVRQA PGKGLEWVAV IWYDGSNIYY    60
SDSVKGRFTI SRANSKNTLY LQMNSLRAED TAVYYCARPG HWNYFFEYWG QGTLVTVSS   119

SEQ ID NO: 8            moltype = AA   length = 108
FEATURE                 Location/Qualifiers
REGION                  1..108
                        note = synthetic construct; antigen binding domain
source                  1..108
                        mol_type = protein
                        organism = synthetic construct
SEQUENCE: 8
DIQMTQSPSS LSASVGDRVT ITCRASQSIN NYLNWYQQKP GKAPKLLIYT ASSLQSGVPS    60
RFSGSGSGTD FTLTISSLQP EDFATYYCQQ SYSTPPLTFG QGTQLEIK                108

SEQ ID NO: 9            moltype = AA   length = 122
FEATURE                 Location/Qualifiers
REGION                  1..122
                        note = synthetic construct; antigen binding domain
source                  1..122
                        mol_type = protein
                        organism = synthetic construct
SEQUENCE: 9
EVQLVESGGG LVQPGGSLRL SCGASGFTFR NYDMHWVRQI TGKGLEWVSA IGSAGDTYYP    60
DSVKGRFTIS RENAKNSLYL QMNSLRVGDT AVYYCTRDIH CSSTRCYGMD VWGQGTTVTV   120
SS                                                                  122
```

```
SEQ ID NO: 10              moltype = AA   length = 108
FEATURE                    Location/Qualifiers
REGION                     1..108
                           note = synthetic construct; antigen binding domain
source                     1..108
                           mol_type = protein
                           organism = synthetic construct
SEQUENCE: 10
DIQMTQSPSS LSASVGDRVT ITCRASQSIS NYLNWYQQKP GKAPKLLIYA ASSLQSGVPS    60
RFSGSGSGTD FTLTISSLQP EDFATYYCQQ SYSTPPITFG QGTRLEIK                108

SEQ ID NO: 11              moltype = AA   length = 130
FEATURE                    Location/Qualifiers
REGION                     1..130
                           note = synthetic construct; antigen binding domain
source                     1..130
                           mol_type = protein
                           organism = synthetic construct
SEQUENCE: 11
EVQLVESGGG LVKPGGSLRL SCAASGFKFS NEWMSWVRQA PGKGLEWVGR IKSKTDGGTT    60
DYAAPVKGRF TISRDDSKNT LYLQMNSLKT EDTAVYYCTT DQDFWSGYYT GADYYGMDVW   120
GQGTMVTVSS                                                         130

SEQ ID NO: 12              moltype = AA   length = 108
FEATURE                    Location/Qualifiers
REGION                     1..108
                           note = synthetic construct; antigen binding domain
source                     1..108
                           mol_type = protein
                           organism = synthetic construct
SEQUENCE: 12
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPPITFG QGTRLEIK                108

SEQ ID NO: 13              moltype = AA   length = 116
FEATURE                    Location/Qualifiers
REGION                     1..116
                           note = synthetic construct; antigen binding domain
source                     1..116
                           mol_type = protein
                           organism = synthetic construct
SEQUENCE: 13
QMQLQQWGAG LLKPSETLSL TCVVYGGSLN GYYWSWIRQS PGKGLEWIGE IDHSGSTNYN    60
PSLKNRVTMS VDTSKIQFSL KLTSVTVADT AVYYCAREGL LPFDYWGQGT LVTVSS       116

SEQ ID NO: 14              moltype = AA   length = 108
FEATURE                    Location/Qualifiers
REGION                     1..108
                           note = synthetic construct; antigen binding domain
source                     1..108
                           mol_type = protein
                           organism = synthetic construct
SEQUENCE: 14
EIVLTQSPGT LSLSPGERVT LSCRASQSVY SNYLAWYQQN PGQAPRLLIY AASNRATGIP    60
DRFSGSGSGT DFTLTISRLE PEDFAVYYCH QYATSPWTFG QGTKVEIK                108

SEQ ID NO: 15              moltype = AA   length = 123
FEATURE                    Location/Qualifiers
REGION                     1..123
                           note = synthetic construct; antigen binding domain
source                     1..123
                           mol_type = protein
                           organism = synthetic construct
SEQUENCE: 15
QLQLQESGPD LVKPSDTLSL TCTVSDDSIS STTYYWAWIR QPPGKGLEWI GSMSYNGNNY    60
YNPSLKSRVA ISAGTSQKQF SLKLTSVTAA DTAVYHCARH LGYNGNWYPF DFWGQGILVT   120
VSS                                                                123

SEQ ID NO: 16              moltype = AA   length = 108
FEATURE                    Location/Qualifiers
REGION                     1..108
                           note = synthetic construct; antigen binding domain
source                     1..108
                           mol_type = protein
                           organism = synthetic construct
SEQUENCE: 16
EIVLTQSPGT LSLSPGERAT LSCRASQSVS SSYLAWYQQK PGQAPRLLIY GASSRTTGIP    60
DRFSGSGSGT DFTLTISRLE PEDFAVYYCQ QYGSSPWTFG QGTKVEIK                108
```

```
SEQ ID NO: 17          moltype = AA  length = 122
FEATURE                Location/Qualifiers
REGION                 1..122
                       note = synthetic construct; antigen binding domain
source                 1..122
                       mol_type = protein
                       organism = synthetic construct
SEQUENCE: 17
EVQVVESGGG LVEPGRSLRL SCKASGFTFD DYAMHWVRQT PGKALEWVSG INWSGNNIGY   60
ADSVKGRFTI SKDDAKNSLY LQMNSLRPED TALYYCTKDI SITGTLDAFD VWGQGTMVTV  120
SS                                                                 122

SEQ ID NO: 18          moltype = AA  length = 107
FEATURE                Location/Qualifiers
REGION                 1..107
                       note = synthetic construct; antigen binding domain
source                 1..107
                       mol_type = protein
                       organism = synthetic construct
SEQUENCE: 18
DIQMTQSPIS VSASVGDRVT ITCRASQGIS NWLAWYQQKP GIAPKLLIYS ASSLQSGVPS   60
RFRGSGSGTD FTLTIGSLQP EDFATYYCQQ AHSFPLTFGG GTKVEIK                107

SEQ ID NO: 19          moltype = AA  length = 116
FEATURE                Location/Qualifiers
REGION                 1..116
                       note = synthetic construct; antigen binding domain
source                 1..116
                       mol_type = protein
                       organism = synthetic construct
SEQUENCE: 19
QVQLVESGGG VVQPGRSLRL SCAASGFTFS SYGMHWVRQA PGKGLEWVAI IWSDGDSEYN   60
LDSVKGRFTI SRDNSKNTLY LQMNSLRVED SAVYYCARDR DLEDIWGQGT MVTVSS      116

SEQ ID NO: 20          moltype = AA  length = 107
FEATURE                Location/Qualifiers
REGION                 1..107
                       note = synthetic construct; antigen binding domain
source                 1..107
                       mol_type = protein
                       organism = synthetic construct
SEQUENCE: 20
DIQMTQSPSS LSASVGDRVT ITCRASQGIR NDLGWYQQKP GKAPKRLIYA ASNLQSGVPS   60
RFSGSGSGTE FTLTISSLQP EDFATYYCLQ HNSYPLTFGG GTKVEIK                107

SEQ ID NO: 21          moltype = AA  length = 117
FEATURE                Location/Qualifiers
REGION                 1..117
                       note = synthetic construct; antigen binding domain
source                 1..117
                       mol_type = protein
                       organism = synthetic construct
SEQUENCE: 21
EVQLLESGGV LVQPGGSLRL SCAASGFTFS NFGMTWVRQA PGKGLEWVSG ISGGGRDTYF   60
ADSVKGRFTI SRDNSKNTLY LQMNSLKGED TAVYYCVKWG NIYFDYWGQG TLVTVSS     117

SEQ ID NO: 22          moltype = AA  length = 107
FEATURE                Location/Qualifiers
REGION                 1..107
                       note = synthetic construct; antigen binding domain
source                 1..107
                       mol_type = protein
                       organism = synthetic construct
SEQUENCE: 22
DIQMTQSPSS LSASVGDSIT ITCRASLSIN TFLNWYQQKP GKAPNLLIYA ASSLHGGVPS   60
RFSGSGSGTD FTLTIRTLQP EDFATYYCQQ SSNTPFTFGP GTVVDFR                107

SEQ ID NO: 23          moltype = AA  length = 121
FEATURE                Location/Qualifiers
REGION                 1..121
                       note = synthetic construct; antigen binding domain
source                 1..121
                       mol_type = protein
                       organism = synthetic construct
SEQUENCE: 23
EVQLVESGGG VVRPGGSLRL SCAASGFTFD DYGMSWVRQV PGKGLEWVSG ISWNDGKTVY   60
AESVKGRFII SRDNAKNSLY LEMNSLRAED TALYYCARDW QYLIERYFDY WGQGTLVTVS  120
S                                                                  121
```

```
SEQ ID NO: 24           moltype = AA  length = 108
FEATURE                 Location/Qualifiers
REGION                  1..108
                        note = synthetic construct; antigen binding domain
source                  1..108
                        mol_type = protein
                        organism = synthetic construct
SEQUENCE: 24
EIVLTQSPGT LSLSPGERAT LSCRASQSVS SSYLAWYQQK PGQAPRLLIY GASSRATGIP   60
DRFSGSGSGT DFTLTISRLE PEDFAVYYCQ QYGSSPWTFG QGTKVEIK               108

SEQ ID NO: 25           moltype = AA  length = 121
FEATURE                 Location/Qualifiers
REGION                  1..121
                        note = synthetic construct; antigen binding domain
source                  1..121
                        mol_type = protein
                        organism = synthetic construct
SEQUENCE: 25
EVQLVESGGG VVRPGGSLRL SCTASGFTFD DYGMSWVRQA PGKGLEWISG IGWTGGRSSY   60
ADSVRGRFTI SRDNAKNSLY LQMNSLGAED TALYYCARDR QWLVQWYFDY WGQGTLVTVS  120
S                                                                 121

SEQ ID NO: 26           moltype = AA  length = 108
FEATURE                 Location/Qualifiers
REGION                  1..108
                        note = synthetic construct; antigen binding domain
source                  1..108
                        mol_type = protein
                        organism = synthetic construct
SEQUENCE: 26
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ SYSTPPITFG QGTRLEIK               108

SEQ ID NO: 27           moltype = AA  length = 121
FEATURE                 Location/Qualifiers
REGION                  1..121
                        note = synthetic construct; antigen binding domain
source                  1..121
                        mol_type = protein
                        organism = synthetic construct
SEQUENCE: 27
EVQLVESGGR VVRPGGSLRL SCAASGFTFD DYGMSWVRQL PGKGLEWVAG ISWNDGKTVY   60
AESVKGRFII SRDNAKNSLH LEMNSLRAED TALYYCARDW QYLIDRYFDF WGQGTLVTVS  120
S                                                                 121

SEQ ID NO: 28           moltype = AA  length = 121
FEATURE                 Location/Qualifiers
REGION                  1..121
                        note = synthetic construct; antigen binding domain
source                  1..121
                        mol_type = protein
                        organism = synthetic construct
SEQUENCE: 28
EVQLVESGGG LVQPGGSLRL SCAASGFTFD DYAMHWVRQA PGKGLEWVSG IGWSSGSIGY   60
ADSVKGRFTI SRDNAKNSLY LQMDSLRPED SALYYCAKAY TFMITLYFDY WGQGTLVTVS  120
S                                                                 121

SEQ ID NO: 29           moltype = AA  length = 121
FEATURE                 Location/Qualifiers
REGION                  1..121
                        note = synthetic construct; antigen binding domain
source                  1..121
                        mol_type = protein
                        organism = synthetic construct
SEQUENCE: 29
EVQLVESGGG LVQPGRSLRL SCAASGFTFD DYDMHWVRQA PGKGLEWVSG SGWNRGSLGY   60
ADSVKGRFTI SRDNAKKSLY LQMNSVRVED TALYYCAKGF VVVSAAYFDY WGQGTLVTVS  120
S                                                                 121

SEQ ID NO: 30           moltype = AA  length = 121
FEATURE                 Location/Qualifiers
REGION                  1..121
                        note = synthetic construct; antigen binding domain
source                  1..121
                        mol_type = protein
                        organism = synthetic construct
```

```
SEQUENCE: 30
QVQLVQSGAE VKRPGSSVKV SCKVSGVTFR NFAIIWVRQA PGQGLEWMGG IIPFFSAANY    60
AQSFQGRVTI TPDESTSTAF MELASLRSED TAVYYCAREG ERGHTYGFDY WGQGTLVTVS   120
S                                                                   121

SEQ ID NO: 31          moltype = AA   length = 121
FEATURE                Location/Qualifiers
REGION                 1..121
                       note = synthetic construct; antigen binding domain
source                 1..121
                       mol_type = protein
                       organism = synthetic construct
SEQUENCE: 31
EVQLVESGGG LVQSGRSLRL SCAASGFTFD DYAMHWVRQP PGKGLEWVSG INWNRGRTGY    60
ADSVKGRFTI SRDNAKNSLY LQMNDLRVED TALYYCAKAE QWLDEGYFDY WGQGTLVTVS   120
S                                                                   121

SEQ ID NO: 32          moltype = AA   length = 121
FEATURE                Location/Qualifiers
REGION                 1..121
                       note = synthetic construct; antigen binding domain
source                 1..121
                       mol_type = protein
                       organism = synthetic construct
SEQUENCE: 32
EVQLVESGGG LVQRGGSLRL SCAASGFSFS SYAMNWVRQA PGKGLEWVST ISDSGGSTYY    60
ADSVKGRFTI SRDNSKNTLS LQMNSLRAED TAVYYCAKDQ GGSYPYYFHY WGQGTLVTVS   120
S                                                                   121

SEQ ID NO: 33          moltype = AA   length = 121
FEATURE                Location/Qualifiers
REGION                 1..121
                       note = synthetic construct; antigen binding domain
source                 1..121
                       mol_type = protein
                       organism = synthetic construct
SEQUENCE: 33
EVQLVESGGG LVQPGRSLRL SCAASGFTFE DYAMHWVRQA PGKGLEWVSG IGWSNVKIGY    60
ADSVKGRFTI SRDNVRNSLY LQMNSLRTED TAFYYCVKAY TSMLTLYFDY WGQGTLVTVS   120
S                                                                   121

SEQ ID NO: 34          moltype = AA   length = 118
FEATURE                Location/Qualifiers
REGION                 1..118
                       note = synthetic construct; antigen binding domain
source                 1..118
                       mol_type = protein
                       organism = synthetic construct
SEQUENCE: 34
QVQLVQSGAE VKRPGASVKV SCKASGYTFT SFYMYWVRQA PGQGLEWMGI INPSDGSTSN    60
AQKFQGRVTM TRDTSTSTVY MELSSLRSED TAVYYCARRV AGDIFDIWGQ GTMVTVSS    118

SEQ ID NO: 35          moltype = AA   length = 119
FEATURE                Location/Qualifiers
REGION                 1..119
                       note = synthetic construct; antigen binding domain
source                 1..119
                       mol_type = protein
                       organism = synthetic construct
SEQUENCE: 35
QVQLQESGPG LVKPSETLSL TCTVSGGSIS SYHWNWIRQS PGKGLEWIGY IYYIGSTDYN    60
PSLESRVTIS VDTSKNQFSL KLSSVTAADT AVYYCARVPV GATGASDVWG QGTMVTVSS   119

SEQ ID NO: 36          moltype = AA   length = 121
FEATURE                Location/Qualifiers
REGION                 1..121
                       note = synthetic construct; antigen binding domain
source                 1..121
                       mol_type = protein
                       organism = synthetic construct
SEQUENCE: 36
EVQLVESGGS VVRPGGSLRL SCVVSGFTFE DYGLSWVRQI PGKGLEWVSG ISWTGGNTGY    60
ADSVKGRFTI SRDNAKNSLY LQMNSLRAED TALYHCTRDR QWLMQWYFDY WGQGTLVTVS   120
S                                                                   121

SEQ ID NO: 37          moltype = AA   length = 119
FEATURE                Location/Qualifiers
REGION                 1..119
                       note = synthetic construct; antigen binding domain
```

```
source                          1..119
                                mol_type = protein
                                organism = synthetic construct
SEQUENCE: 37
QVQLVESGGG VVQPGRSLRL SCSASGFTFS AYAMHWVRQA PGKGLEWVAA ISYGGSDKYY    60
ADSVKGRFTI SRDNSKNTLY LQMNSLRTDD TAVYYCAKSA HWNFFFDYWG QGTLVTVSS    119

SEQ ID NO: 38                   moltype = AA  length = 121
FEATURE                         Location/Qualifiers
REGION                          1..121
                                note = synthetic construct; antigen binding domain
source                          1..121
                                mol_type = protein
                                organism = synthetic construct
SEQUENCE: 38
EVQLVESGGG LVQPGRSLRL SCVASGFALH DYAMHWVRQV PGKGLEWVSS ISWNSGVIGY    60
ADSLKGRFTI SRDNAKNSLY LQMNSLRAED TALYYCAKGS GSYYVSWFDP WGQGTLVTVS   120
S                                                                  121

SEQ ID NO: 39                   moltype = AA  length = 123
FEATURE                         Location/Qualifiers
REGION                          1..123
                                note = synthetic construct; antigen binding domain
source                          1..123
                                mol_type = protein
                                organism = synthetic construct
SEQUENCE: 39
QLQLQESGPG LVQPSETLSL TCTVSGDSIS STAYHWDWIR QPPGKGLEWI GTITYNGNTY    60
FNPSLKSRVT ISVDTSKNQF SLKLLSMTAA ETAVFYCARH LGYNSDFFPF DFWGQGTLVT   120
VSS                                                                123

SEQ ID NO: 40                   moltype = AA  length = 119
FEATURE                         Location/Qualifiers
REGION                          1..119
                                note = synthetic construct; antigen binding domain
source                          1..119
                                mol_type = protein
                                organism = synthetic construct
SEQUENCE: 40
EVQLVESGGG LVRPGGSLRL SCAASGFTFS TYAMAWVRQT PGKGLEGVSA IGGSGDSTYY    60
VDSVKGRFTI SRDNSKSTLF LQMNSLRAED TAVYYCVKVR NYDGSFDIWG QGTMVTVSS    119

SEQ ID NO: 41                   moltype = AA  length = 124
FEATURE                         Location/Qualifiers
REGION                          1..124
                                note = synthetic construct; antigen binding domain
source                          1..124
                                mol_type = protein
                                organism = synthetic construct
SEQUENCE: 41
EVQLLESGGG LVQPGGSLRL SCVASGFTFS TYAMSWVRQA PGMGLEWVSS ISGSGRNTYY    60
ADSVKGRFTI SRDNSKNTLF LQMNSLRAED TAVYYCAKES VTGTSSYYYG VDVWGQGTTV   120
TVSS                                                               124

SEQ ID NO: 42                   moltype = AA  length = 107
FEATURE                         Location/Qualifiers
REGION                          1..107
                                note = synthetic construct; antigen binding domain
source                          1..107
                                mol_type = protein
                                organism = synthetic construct
SEQUENCE: 42
DIQMTQSPSS LSASVGDRVT ITCRASQSIS SYLNWYHQKP GKAPKLLIYA ASSLQNGVPS    60
RFSGSGSGTD FTLTISSLQP EDFASYYCQQ SYRTPLTFGG GTKVEIK                 107

SEQ ID NO: 43                   moltype = AA  length = 128
FEATURE                         Location/Qualifiers
REGION                          1..128
                                note = synthetic construct; antigen binding domain
source                          1..128
                                mol_type = protein
                                organism = synthetic construct
SEQUENCE: 43
QVQLEESGGG VVQPGRSLRL SCAASGFTFS WYGMHWVRQA PGKGLEWVAL IWYDGTNKKY    60
GDSVKGRFTI SRDNSKNTVY LQMNSLRAED TAVYYCARDC GHSGNDRGTY YYYYGMDVWG   120
QGTTVTVS                                                           128

SEQ ID NO: 44                   moltype = AA  length = 108
FEATURE                         Location/Qualifiers
```

-continued

```
REGION                  1..108
                        note = synthetic construct; antigen binding domain
source                  1..108
                        mol_type = protein
                        organism = synthetic construct
SEQUENCE: 44
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPPITFG QGTRLEIK               108

SEQ ID NO: 45           moltype = AA  length = 119
FEATURE                 Location/Qualifiers
REGION                  1..119
                        note = synthetic construct; antigen binding domain
source                  1..119
                        mol_type = protein
                        organism = synthetic construct
SEQUENCE: 45
QVQLQQWGAG LLKPSETLSL TCAVYGGSFS GYYWNWIRQP PGKGLEWVGE ISHRGTTNYN    60
PSLKSRVTIS LDTSKNQFSL KLTSVTAADT AVYYCSRDEE LEFRFFDYWG QGTLVTVSS    119

SEQ ID NO: 46           moltype = AA  length = 107
FEATURE                 Location/Qualifiers
REGION                  1..107
                        note = synthetic construct; antigen binding domain
source                  1..107
                        mol_type = protein
                        organism = synthetic construct
SEQUENCE: 46
EIVLTQSPAT LSLSPGERAT LSCRASQSVS SYLAWYQQKP GQAPRLLVYG ASNRATGIPA    60
RFSGSGSGTD FTLTISSLEP EDFAFYYCQQ RSNWPLTFGG GTKVEIK                107

SEQ ID NO: 47           moltype = AA  length = 119
FEATURE                 Location/Qualifiers
REGION                  1..119
                        note = synthetic construct; antigen binding domain
source                  1..119
                        mol_type = protein
                        organism = synthetic construct
SEQUENCE: 47
QLQLQESGPG LVKPSETLSL TCTVSGDSII SNSYYWGWIR QPPGKGLEWI GNFFYTGATY    60
YNPSLKSRVT ISADTSKNQF SLKLSSVTAA DTALYYCASY NRNYRFDPWG QGTLVTVSS    119

SEQ ID NO: 48           moltype = AA  length = 108
FEATURE                 Location/Qualifiers
REGION                  1..108
                        note = synthetic construct; antigen binding domain
source                  1..108
                        mol_type = protein
                        organism = synthetic construct
SEQUENCE: 48
DIQMTQSPSS LSASVGDRVT ITCRASQSIS SYLNWYQQKP GKAPKLLIYA ASSLQSGVPS    60
RFSGSGSGTD FTLTISSLQP EDFATYFCQQ SYSTPPITFG QGTRLEIK               108

SEQ ID NO: 49           moltype = AA  length = 127
FEATURE                 Location/Qualifiers
REGION                  1..127
                        note = synthetic construct; antigen binding domain
source                  1..127
                        mol_type = protein
                        organism = synthetic construct
SEQUENCE: 49
QVQLQQWGAG LLKPSETLSL TCAVYGGSFS TYYWSWIRQP PGKGLEWIGE INHSGNADYN    60
PSLKSRVSIS VDTSKNQFSL RLSSVTAADT AIYYCARAGY CSSPTCYSYY YFGMDVWGQG   120
TTVTVSS                                                            127

SEQ ID NO: 50           moltype = AA  length = 108
FEATURE                 Location/Qualifiers
REGION                  1..108
                        note = synthetic construct; antigen binding domain
source                  1..108
                        mol_type = protein
                        organism = synthetic construct
SEQUENCE: 50
EIVLTQSPGT LSLSLGERAT LSCRASQSVI SSFLAWYQQK PGQAPRLLIY GASSRATGFP    60
DRFSGSGSGT DFTLTIRRLE PEDFAVYYCQ QYGNSPWTFG QGTKVEIK               108

SEQ ID NO: 51           moltype = AA  length = 129
FEATURE                 Location/Qualifiers
```

| | | |
|---|---|---|
| REGION | 1..129 | |
| | note = synthetic construct; antigen binding domain | |
| source | 1..129 | |
| | mol_type = protein | |
| | organism = synthetic construct | |

SEQUENCE: 51
```
QVTLKESGPV LVKPTETLTL TCTVSGFSLS NAGMGVSWVR QPPGKALEWL AHIFSNDEKS    60
YSTSLRTRLT ISKDTSKSQV VLTVTNLDPV DTATYFCARI PEFTSSSWAL YYFYGMDVWG   120
QGTTVTSS                                                            129
```

| | | |
|---|---|---|
| SEQ ID NO: 52 | moltype = AA  length = 108 | |
| FEATURE | Location/Qualifiers | |
| REGION | 1..108 | |
| | note = synthetic construct; antigen binding domain | |
| source | 1..108 | |
| | mol_type = protein | |
| | organism = synthetic construct | |

SEQUENCE: 52
```
EIVLTQSPGT LSLSPGESAT LSCRASQSIT STYFAWYQQK PGQAPRLLIY ATSSRATGVP    60
DRFSGSGSGT DFTLTISRLE PDDFAVYYCQ QYGRSPWTFG QGTKVEVK                108
```

| | | |
|---|---|---|
| SEQ ID NO: 53 | moltype = AA  length = 121 | |
| FEATURE | Location/Qualifiers | |
| REGION | 1..121 | |
| | note = synthetic construct; antigen binding domain | |
| source | 1..121 | |
| | mol_type = protein | |
| | organism = synthetic construct | |

SEQUENCE: 53
```
QVQLVQSGAE VKKPGASVKV SCKASGYTFT SYGISWVRQA PGQGLEWMGW ISAYNDNTNY    60
AQKLQGRVTM TADTSTNTAY MELRSLRSDD TAIYYCVRWN WGSVYWYFDL WGRGTLVTVS   120
S                                                                   121
```

| | | |
|---|---|---|
| SEQ ID NO: 54 | moltype = AA  length = 108 | |
| FEATURE | Location/Qualifiers | |
| REGION | 1..108 | |
| | note = synthetic construct; antigen binding domain | |
| source | 1..108 | |
| | mol_type = protein | |
| | organism = synthetic construct | |

SEQUENCE: 54
```
EIVLTQSPGT LSLSPGERAT LSCRASQIIS SSYFAWYQQK PGQAPRLLIY GASSRATGIP    60
DRFSGSVSGT DFTLTISRLE PEDFAMYFCQ QYGNSPWTFG QGTKVEIK                108
```

| | | |
|---|---|---|
| SEQ ID NO: 55 | moltype = AA  length = 117 | |
| FEATURE | Location/Qualifiers | |
| REGION | 1..117 | |
| | note = synthetic construct; antigen binding domain | |
| source | 1..117 | |
| | mol_type = protein | |
| | organism = synthetic construct | |

SEQUENCE: 55
```
QITLKESGPT LVKPTQTLTL TCTFSGFSLN THRVGVGWIR QPPGKALEWL ALIYGNDVKN    60
YSPSLETRLT IAKDTSKNQV VLTMTNMDPV DTATYFCSYI TGEGMYWGQG TLVTVSS      117
```

| | | |
|---|---|---|
| SEQ ID NO: 56 | moltype = AA  length = 111 | |
| FEATURE | Location/Qualifiers | |
| REGION | 1..111 | |
| | note = synthetic construct; antigen binding domain | |
| source | 1..111 | |
| | mol_type = protein | |
| | organism = synthetic construct | |

SEQUENCE: 56
```
DVVMTQSPLS LSVTLGQPAS ISCRSSQNLM YSDGNTYLNW FHQRPGQSPR RLIYKVSNRD    60
SGVPDRFSGS GSGTDFTLKI SRVEAEDVGV YYCMQGTHWY TFGQGTKLEI K            111
```

| | | |
|---|---|---|
| SEQ ID NO: 57 | moltype = AA  length = 119 | |
| FEATURE | Location/Qualifiers | |
| REGION | 1..119 | |
| | note = synthetic construct; antigen binding domain | |
| source | 1..119 | |
| | mol_type = protein | |
| | organism = synthetic construct | |

SEQUENCE: 57
```
QVQLQQWGAG LLKPSETLSL TCAVYGGSFS GYYWSWIRQP PGKGLEWIGE INHRGNTNYN    60
PSLKSRVTIS LDTSKKQFSL NLSSVTAADT AMYYCTRDEE QELRFLDYWG QGTLVTVSS    119
```

| | | |
|---|---|---|
| SEQ ID NO: 58 | moltype = AA  length = 107 | |
| FEATURE | Location/Qualifiers | |

```
REGION                      1..107
                            note = synthetic construct; antigen binding domain
source                      1..107
                            mol_type = protein
                            organism = synthetic construct
SEQUENCE: 58
EIVLTQSPAT LSLSPGERAT LSCRASQDIS TYLAWYQQRA GQAPRLLIYG ASNRATGIPA    60
RFSGSGSGTD FTLTISSLEP EDFAFYYCQQ RSNWPLTFGG GTEVEIK                 107

SEQ ID NO: 59               moltype = AA   length = 122
FEATURE                     Location/Qualifiers
REGION                      1..122
                            note = synthetic construct; antigen binding domain
source                      1..122
                            mol_type = protein
                            organism = synthetic construct
SEQUENCE: 59
QVQLQQWGAG LLKPSETLSL TCVVHGGSFS GYYWNWIRQP PGKGLEWIGE INHRGNTNYN    60
PSLKSRVTVS EDTSKNQFSL KLSSLTAADT AVYYCVRGED YDFWSDYYND YWGQGTLVTV   120
SS                                                                 122

SEQ ID NO: 60               moltype = AA   length = 107
FEATURE                     Location/Qualifiers
REGION                      1..107
                            note = synthetic construct; antigen binding domain
source                      1..107
                            mol_type = protein
                            organism = synthetic construct
SEQUENCE: 60
EIVLTQSPAT LSLSPGERAT LSCRASQTIS SYLAWHQQKP GQAPRLLIYD ASKRATGIPA    60
RFSGSGSGTD FTLTITSLEP EDFAVYYCQQ RSNWPLTFGG GTKVEIK                 107

SEQ ID NO: 61               moltype = AA   length = 124
FEATURE                     Location/Qualifiers
REGION                      1..124
                            note = synthetic construct; antigen binding domain
source                      1..124
                            mol_type = protein
                            organism = synthetic construct
SEQUENCE: 61
QVQLQQWGAG LLPPSETLSL ICAVYGGSFS GYYWSWIRQP PGKGLEWIGE INHRGSTNYN    60
PSLKSRATIS VDTSKNQFSL KLSSVTAADT AVYYCSRGED YYDSSGYSYY FDWGQGTLV    120
TVSS                                                               124

SEQ ID NO: 62               moltype = AA   length = 107
FEATURE                     Location/Qualifiers
REGION                      1..107
                            note = synthetic construct; antigen binding domain
source                      1..107
                            mol_type = protein
                            organism = synthetic construct
SEQUENCE: 62
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPLTFGG GTKVEIK                 107

SEQ ID NO: 63               moltype = AA   length = 122
FEATURE                     Location/Qualifiers
REGION                      1..122
                            note = synthetic construct; antigen binding domain
source                      1..122
                            mol_type = protein
                            organism = synthetic construct
SEQUENCE: 63
QVQLQQWGAG LLRPSETLSL TCAVYGGSFS GYYWNWIRQS PGTGLEWIGE INHRGNINFN    60
PSLKSRVTIS EDTSKNQFSL RLNSVTAADT AVYYCARGED YDIWSGYYRE YWGQGTLVTV   120
SS                                                                 122

SEQ ID NO: 64               moltype = AA   length = 107
FEATURE                     Location/Qualifiers
REGION                      1..107
                            note = synthetic construct; antigen binding domain
source                      1..107
                            mol_type = protein
                            organism = synthetic construct
SEQUENCE: 64
EIVLTQSPAT LSLSPGERAT LSCRASQSVS SYLAWYQQKP GQAPRLLIYD ASKRATGIPA    60
RFSGSGSGTD FTLTISSLEP EDFAVYYCQQ RSNWPLAFGG GTKVEIK                 107

SEQ ID NO: 65               moltype = AA   length = 119
```

```
                          FEATURE                 Location/Qualifiers
                          REGION                  1..119
                                                  note = synthetic construct; antigen binding domain
                          source                  1..119
                                                  mol_type = protein
                                                  organism = synthetic construct
SEQUENCE: 65
QVQLQQWGAG LLKPSETLSL TCAVYGGSFS EFYWNWIRQP PEKGLEWIGE INHRGNTNYN    60
PSLKSRVTIS VDMSKNQFSL QLNSVTVADT ALYYCAFGYD FRSSYEDVWG QGTTVTVSS    119

SEQ ID NO: 66             moltype = AA   length = 107
FEATURE                   Location/Qualifiers
REGION                    1..107
                          note = synthetic construct; antigen binding domain
source                    1..107
                          mol_type = protein
                          organism = synthetic construct
SEQUENCE: 66
EIVLTQSPAT LSLSPGERAT LSCRASQDIS TYLAWHQQKP GQPPRLLIYG SSNRATGIPA    60
RFSGSGSGTD FTLTISSLEP EDFAVYYCQQ RSNWPLTFGG GTKVEIK                107

SEQ ID NO: 67             moltype = AA   length = 124
FEATURE                   Location/Qualifiers
REGION                    1..124
                          note = synthetic construct; antigen binding domain
source                    1..124
                          mol_type = protein
                          organism = synthetic construct
SEQUENCE: 67
EVQLLESGGG LVQPGGSLRL SCAASGFTFR SYAMSWVRQA PGKGLEWVSV ISGGGGRTYY    60
TDSVKGRFTI SRDNSKSMLY LQMNSLRAED TAIYYCAKER VTGIDHYYYG VDVWGQGTTV   120
TVSS                                                               124

SEQ ID NO: 68             moltype = AA   length = 107
FEATURE                   Location/Qualifiers
REGION                    1..107
                          note = synthetic construct; antigen binding domain
source                    1..107
                          mol_type = protein
                          organism = synthetic construct
SEQUENCE: 68
DIQMTQSPSS LSASVGDRVT ITCRASQSIS SYLNWYQQKP GKAPKLLIYA TSSLQSGVPS    60
RFSGSASGTD FTLAISSLQP EDFATYYCQQ SYTTPLTFGG GTKVEIK                107

SEQ ID NO: 69             moltype = AA   length = 130
FEATURE                   Location/Qualifiers
REGION                    1..130
                          note = synthetic construct; antigen binding domain
source                    1..130
                          mol_type = protein
                          organism = synthetic construct
SEQUENCE: 69
EVQLVESGGG LVQPGGSLRL SCAASGFTFS SYEMNWVRQA PGKGLEWVSY ISSSGNTKDY    60
AGSVKGRVTI SRDNAKNLLY LQMNSLRAED TAVYHCARDG GHYDILTGSM SYYYYALDVW   120
GQGTTVTVSS                                                         130

SEQ ID NO: 70             moltype = AA   length = 108
FEATURE                   Location/Qualifiers
REGION                    1..108
                          note = synthetic construct; antigen binding domain
source                    1..108
                          mol_type = protein
                          organism = synthetic construct
SEQUENCE: 70
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPPITFG QGTRLEIK                108

SEQ ID NO: 71             moltype = AA   length = 121
FEATURE                   Location/Qualifiers
REGION                    1..121
                          note = synthetic construct; antigen binding domain
source                    1..121
                          mol_type = protein
                          organism = synthetic construct
SEQUENCE: 71
EVQLVESGGG LVQPGGSLRL SCAASGFTFK TYAMSWVRQA PGRGLEWVSG ISGSGSTSYY    60
ADSVKGRFTI SRDNYKKTLS LQMNSLRAED TAVYYCALDI MATVGGLFNN WGQGTLVTVS   120
S                                                                  121
```

```
SEQ ID NO: 72             moltype = AA  length = 108
FEATURE                   Location/Qualifiers
REGION                    1..108
                          note = synthetic construct; antigen binding domain
source                    1..108
                          mol_type = protein
                          organism = synthetic construct
SEQUENCE: 72
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYGSSPWTFG QGTKVEIK                 108

SEQ ID NO: 73             moltype = AA  length = 120
FEATURE                   Location/Qualifiers
REGION                    1..120
                          note = synthetic construct; antigen binding domain
source                    1..120
                          mol_type = protein
                          organism = synthetic construct
SEQUENCE: 73
QVQLVQSGAE VKKPGSSVKV SCKASGGTFS RHTISWVRQA PGQGLEWMGG IIPIFGTANY    60
AHKFQGRVTI TTDESTSTAY MELSSLRSED TAVYYCARAP YTRQGYFDLW GRGTLVTVSS    120

SEQ ID NO: 74             moltype = AA  length = 113
FEATURE                   Location/Qualifiers
REGION                    1..113
                          note = synthetic construct; antigen binding domain
source                    1..113
                          mol_type = protein
                          organism = synthetic construct
SEQUENCE: 74
DIVMTQSPDS LAVSLGERAT INCKSSQSVL YSSNNKNYLA WYQQKPGQPP KLLIYWASTR    60
ESGVPDRFSG SGSGTDFTLT ISSLQAEDVA VYYCQQDYST PWTFGQGTKV EIK           113

SEQ ID NO: 75             moltype = AA  length = 118
FEATURE                   Location/Qualifiers
REGION                    1..118
                          note = synthetic construct; antigen binding domain
source                    1..118
                          mol_type = protein
                          organism = synthetic construct
SEQUENCE: 75
QVQLVQSGAE VKKPGASVKV SCKASGYTFT NYYIHWVRQA PGQGLDWMGI INPGGGNTNY    60
AQKFLGRVTM TRDTSTTTVY MELSSLRSED TAIYYCAREN WNSYFDNWGQ GTLVTVSS      118

SEQ ID NO: 76             moltype = AA  length = 113
FEATURE                   Location/Qualifiers
REGION                    1..113
                          note = synthetic construct; antigen binding domain
source                    1..113
                          mol_type = protein
                          organism = synthetic construct
SEQUENCE: 76
DIVMTQSPDS LAVSLGERAT INCKSSQSVL YSSNNKNFLA WYQQKPGQPP KLLIYWASTR    60
ESGVPDRFSG SGSGTDFTLT ISSLQAEDVA LYYCQQYYGA PWTFGQGTKV EIK           113

SEQ ID NO: 77             moltype = AA  length = 119
FEATURE                   Location/Qualifiers
REGION                    1..119
                          note = synthetic construct; antigen binding domain
source                    1..119
                          mol_type = protein
                          organism = synthetic construct
SEQUENCE: 77
QVQLVQSGAE VKKPGSSVKV SCKASGGTFS SYTINWVRQA PGQGLEWMGG IIPIFGIANY    60
AQKFQGRVTI TTDESTNTAY MELSSLRSED TAIYYCARAR YGSGSYDYWG QGTLVTVSS     119

SEQ ID NO: 78             moltype = AA  length = 113
FEATURE                   Location/Qualifiers
REGION                    1..113
                          note = synthetic construct; antigen binding domain
source                    1..113
                          mol_type = protein
                          organism = synthetic construct
SEQUENCE: 78
DIVMTQSPDS LAVSLGERAT INCKSSQSVL YTSNNKNYLA WYQQKPGQPP KLLIYWASTR    60
ESGVPDRFSG SGSGTDFTLT ISSLQAEDVA VYYCQQYYNT PWTFGQGTKV EIK           113

SEQ ID NO: 79             moltype = AA  length = 120
FEATURE                   Location/Qualifiers
```

```
REGION                  1..120
                        note = synthetic construct; antigen binding domain
source                  1..120
                        mol_type = protein
                        organism = synthetic construct
SEQUENCE: 79
QITLKESGPT LVKPTQTLTL TCTFSGFSLS TNGVGVGWIR QPPGKALEWL GIIYWNDDKR    60
YSPSLRSRLT ITKDTSKNQV VLTMTNMDPV DTATYYCAHR GLFGGWFDPW GQGTLVTVSS   120

SEQ ID NO: 80           moltype = AA  length = 107
FEATURE                 Location/Qualifiers
REGION                  1..107
                        note = synthetic construct; antigen binding domain
source                  1..107
                        mol_type = protein
                        organism = synthetic construct
SEQUENCE: 80
DIQMTQSPSS LSASVGDRVT ITCRASQSIS RYLNWYQQKP GKAPNLLIFA ASSLQSGVPS    60
RFSGSGSGTD FTLTISSLQP EDFATYFCQQ SYNTPLTFGG GTKVEIK                107

SEQ ID NO: 81           moltype = AA  length = 122
FEATURE                 Location/Qualifiers
REGION                  1..122
                        note = synthetic construct; antigen binding domain
source                  1..122
                        mol_type = protein
                        organism = synthetic construct
SEQUENCE: 81
EVQLVESGGG LVQPGGSLRL SCAISGFTFR SYAMTWVRQA PGKALEWVSV ISGSGGNTYY    60
ADSVKGRFTV SRDNSRNTLY LQMNSLRAED TAVYFCSKVA AANNYYYALD VWGQGTTVTV   120
SS                                                                 122

SEQ ID NO: 82           moltype = AA  length = 112
FEATURE                 Location/Qualifiers
REGION                  1..112
                        note = synthetic construct; antigen binding domain
source                  1..112
                        mol_type = protein
                        organism = synthetic construct
SEQUENCE: 82
DIVMTQSPLS LPVTPGEPAS ISCRSSQSLL HSNGYKYLDW YLQKPGQSPQ LLIYLVSNRA    60
SGVPDRFSGS GSGTDFTLKI SRVEAEDVGV YYCMQALQTP YTFGQGTKLE IK           112

SEQ ID NO: 83           moltype = AA  length = 127
FEATURE                 Location/Qualifiers
REGION                  1..127
                        note = synthetic construct; antigen binding domain
source                  1..127
                        mol_type = protein
                        organism = synthetic construct
SEQUENCE: 83
QVQLVESGGG VVQPGRSLRL SCVASGFTFS NYGMHWVRQA PGKGLEWVAV IWNDGSNKYY    60
ADSVKGRFTI SRDNSKNTLY LQVSSLRADD TAVYYCARDG EVEYSSSNYN YYGLDVWGQG   120
TTVTVSS                                                            127

SEQ ID NO: 84           moltype = AA  length = 107
FEATURE                 Location/Qualifiers
REGION                  1..107
                        note = synthetic construct; antigen binding domain
source                  1..107
                        mol_type = protein
                        organism = synthetic construct
SEQUENCE: 84
DIQMTQSPSS LSASVGDRVT ITCQASQDIS NYLNWYQQKP GKAPKLLIYD ASNLETGVPS    60
RFSGSGSGTD FTFTISSLQP EDIVTYYCQQ YDDLPITFGQ GTRLEIK                107

SEQ ID NO: 85           moltype = AA  length = 125
FEATURE                 Location/Qualifiers
REGION                  1..125
                        note = synthetic construct; antigen binding domain
source                  1..125
                        mol_type = protein
                        organism = synthetic construct
SEQUENCE: 85
EVQLVESGGG LVQPGGSLRL SCAASGFSFH NFAMNWVRQA PGKGLEWVSV ITGSGTSTHY    60
ADSVKGRFTI SRDNSKKTLY LQMNSLRAED TAVYYCAKDR GYDYSGSYYN WFDPWGQGTL   120
VTVSS                                                              125
```

```
SEQ ID NO: 86           moltype = AA  length = 109
FEATURE                 Location/Qualifiers
REGION                  1..109
                        note = synthetic construct; antigen binding domain
source                  1..109
                        mol_type = protein
                        organism = synthetic construct
SEQUENCE: 86
DIQMTQSPSS LSASVGDRIT ITCRASQSIS SYLNWYQQKP GKAPKLLIFA ASNLQSGVPS    60
RFSGSGSGTD FTLTISSLQP EDFATYYCQQ SYSTPSLFTF GPGTKVDIK               109

SEQ ID NO: 87           moltype = AA  length = 128
FEATURE                 Location/Qualifiers
REGION                  1..128
                        note = synthetic construct; antigen binding domain
source                  1..128
                        mol_type = protein
                        organism = synthetic construct
SEQUENCE: 87
EVQLVESGGG LVQPGGSLRL SCAVSGFTFS SYEMNWVRQA PGKGLEWVSH ISSSGSTIYY    60
ADSVKGRFTM SRDNAKNSLY LQMNSLRAED TAVYYCARDG NIWSGYYAAY YFYGMDVWGQ   120
GTTVTVSS                                                            128

SEQ ID NO: 88           moltype = AA  length = 112
FEATURE                 Location/Qualifiers
REGION                  1..112
                        note = synthetic construct; antigen binding domain
source                  1..112
                        mol_type = protein
                        organism = synthetic construct
SEQUENCE: 88
DIVMTQTPLS SPVTLGQPAS ISCRSSQSLV HSDGKTYLSW LQQRPGQPPR LLIYKISNRF    60
SGVPDRISGS GAGTDFTLKI SRVEAEDVGV YYCMQAVQFP RTFGQGTKVE IK           112

SEQ ID NO: 89           moltype = AA  length = 122
FEATURE                 Location/Qualifiers
REGION                  1..122
                        note = synthetic construct; antigen binding domain
source                  1..122
                        mol_type = protein
                        organism = synthetic construct
SEQUENCE: 89
QVQLQQWGAG LLNPSETLSL TCAVYGGAFS DYYWNWIRQP PGKGLEWIGE INHRGSTNYN    60
PSLKSRVTIS VDTSKNQFSL RMSSVTAADA AVYYCARGED YDIWNGYYQE KWGQGTLVTV   120
SS                                                                  122

SEQ ID NO: 90           moltype = AA  length = 107
FEATURE                 Location/Qualifiers
REGION                  1..107
                        note = synthetic construct; antigen binding domain
source                  1..107
                        mol_type = protein
                        organism = synthetic construct
SEQUENCE: 90
EIVLTQSPAT LSLSPGERAT LSCRASQSIS TYLAWYQQKP GQAPRLLIYD ASKRATGIPA    60
RFSGSGSGTD FTLTISSLEP EDFVVYYCHQ RSNWPLTFGG GTKVEIK                 107

SEQ ID NO: 91           moltype = AA  length = 117
FEATURE                 Location/Qualifiers
REGION                  1..117
                        note = synthetic construct; antigen binding domain
source                  1..117
                        mol_type = protein
                        organism = synthetic construct
SEQUENCE: 91
QVQLQESGPG LVKPSETLSL TCTVSGGSFS SYYWSWLRQP PGKGLEWIGY IFYSGSTDYN    60
PSLKSRVTIS VDTSKKQFSL KLTSVTAADT AVYYCARTIS TWWFAPWGQG TLVTVSS      117

SEQ ID NO: 92           moltype = AA  length = 106
FEATURE                 Location/Qualifiers
REGION                  1..106
                        note = synthetic construct; antigen binding domain
source                  1..106
                        mol_type = protein
                        organism = synthetic construct
SEQUENCE: 92
EIVMTQSPAT LSVSPGGRAT LSCRASQSVS NNVAWYQQKP GQAPRLLIYG ASTRATGIPG    60
RFSGSGSGTE FTLTISSLQS EDFAVYSCQQ YNNWLTFGGG TKVEIK                  106
```

```
SEQ ID NO: 93              moltype = AA   length = 123
FEATURE                    Location/Qualifiers
REGION                     1..123
                           note = synthetic construct; antigen binding domain
source                     1..123
                           mol_type = protein
                           organism = synthetic construct
SEQUENCE: 93
QVQLVESGGG VVQPGRSLRL SCVASGFTFS SYGMHWVRQA PGKGLEWVAI IWYDGSNKYY    60
ADSVKGRFTI SRDNSKNTQY LQMNSLRAED TAVYYCASVA TSGDFDYYGM DVWGQGTTVT   120
VSS                                                                 123

SEQ ID NO: 94              moltype = AA   length = 107
FEATURE                    Location/Qualifiers
REGION                     1..107
                           note = synthetic construct; antigen binding domain
source                     1..107
                           mol_type = protein
                           organism = synthetic construct
SEQUENCE: 94
EIVLTQSPAT LSLSPGERTT LSCRASQRIS TYLAWYQQKP GQAPRLLIYD ASKRATGIPA    60
RFSGSGSGTG FTLTISSLEP EDFAVYYCQQ RSNWPLTFGG GTKVEIK                 107

SEQ ID NO: 95              moltype = AA   length = 119
FEATURE                    Location/Qualifiers
REGION                     1..119
                           note = synthetic construct; antigen binding domain
source                     1..119
                           mol_type = protein
                           organism = synthetic construct
SEQUENCE: 95
EVQLVQSGAE VRKPGESLKI SCKGSGYSFT NYWIVWVRQM PGKGLEWMGI IYPGDSDTRY    60
SPSFQGQVTI SADKSISTAY LQWSSLKASD TAMYYCARRD TIFPSYPLWG QGTLVTVSS    119

SEQ ID NO: 96              moltype = AA   length = 112
FEATURE                    Location/Qualifiers
REGION                     1..112
                           note = synthetic construct; antigen binding domain
source                     1..112
                           mol_type = protein
                           organism = synthetic construct
SEQUENCE: 96
DIVMTQSPLS LPVTPGEPAS ISCRSSQSLL NSNGYNFLDW YLQKPGQSPQ LLIYLVSNRA    60
SGVPDRFSGS GSGTDFTLKI SRVEAEDIGV YYCMQALQTP ITFGQGTRLE IK           112

SEQ ID NO: 97              moltype = AA   length = 120
FEATURE                    Location/Qualifiers
REGION                     1..120
                           note = synthetic construct; antigen binding domain
source                     1..120
                           mol_type = protein
                           organism = synthetic construct
SEQUENCE: 97
QITLKESGPT LVKPTQTLTL TCTFSGFSLS TNGVGVGWIR QPPGKALEWL TLIYWNENKH    60
YSPSLKNRIT ITKDTSKNQV VLTMTNLDPV DTATYYCVHR GWLGAIFAYW GQGTLVTVSS   120

SEQ ID NO: 98              moltype = AA   length = 108
FEATURE                    Location/Qualifiers
REGION                     1..108
                           note = synthetic construct; antigen binding domain
source                     1..108
                           mol_type = protein
                           organism = synthetic construct
SEQUENCE: 98
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPPITFG QGTRLEIK                108

SEQ ID NO: 99              moltype = AA   length = 126
FEATURE                    Location/Qualifiers
REGION                     1..126
                           note = synthetic construct; antigen binding domain
source                     1..126
                           mol_type = protein
                           organism = synthetic construct
SEQUENCE: 99
EVQLVESGGG LVQPGGSLRL SCAASGFTFT SYAMTWVRQA PGKGLEWVSD ISGSGGRTYY    60
ADSVKGRFTI SRDNSKNMLY LQMNILRAED TAVYHCAKGT GQQVDLYNYY YALDVWGQGT   120
TVTVSS                                                              126
```

```
SEQ ID NO: 100          moltype = AA   length = 129
FEATURE                 Location/Qualifiers
REGION                  1..129
                        note = synthetic construct; antigen binding domain
source                  1..129
                        mol_type = protein
                        organism = synthetic construct
SEQUENCE: 100
QVQLVESGGG VVQPGRSLRL SCAASGFTFS YYGMHWVRQA PGKGLEWVAV IWYDGSNKHY    60
ADSVKGRFTI SRDNSKNTLY LQMNSLRADD TAVYYCARDK GISGIKGGSY YYYYAMDVWG   120
QGTTVTVSS                                                           129

SEQ ID NO: 101          moltype = AA   length = 120
FEATURE                 Location/Qualifiers
REGION                  1..120
                        note = synthetic construct; antigen binding domain
source                  1..120
                        mol_type = protein
                        organism = synthetic construct
SEQUENCE: 101
EVQLVESGGG LVKPGGSLRL SCAASGFTFS NAWMTWVRQA PGKGLEWVGR IKNKIDGGTT    60
DYAAPVKGRF TISRDDSKNT VYLQMNSLKT EDTAVYYCST VDYNWYFDFW GRGTLVTVSS   120

SEQ ID NO: 102          moltype = AA   length = 129
FEATURE                 Location/Qualifiers
REGION                  1..129
                        note = synthetic construct; antigen binding domain
source                  1..129
                        mol_type = protein
                        organism = synthetic construct
SEQUENCE: 102
QVQLVESGGG VVQPGRSLRL SCAASGFTFS FFGMHWVRQA PGKGLEWVAL IWYDGTNENY    60
ADSVKGRFTI SRDNSKSTLY LQMNSLRAED TAVYYCARDR GVATFTRGNY YYNYGMDVWG   120
QGTTVTVSS                                                           129

SEQ ID NO: 103          moltype = AA   length = 129
FEATURE                 Location/Qualifiers
REGION                  1..129
                        note = synthetic construct; antigen binding domain
source                  1..129
                        mol_type = protein
                        organism = synthetic construct
SEQUENCE: 103
QVQLVESGGG VVQPGRSLRL SCAASGFTFS FYGMHWVRQA PGKGLEGVAV IWYDGSNKYY    60
ADSVKGRFTI SRDNSKNMLY LQMTSLRAED TAVYYCARDS GKTGTGITGY SYYYGMDVWG   120
QGTTVTVSS                                                           129

SEQ ID NO: 104          moltype = AA   length = 118
FEATURE                 Location/Qualifiers
REGION                  1..118
                        note = synthetic construct; antigen binding domain
source                  1..118
                        mol_type = protein
                        organism = synthetic construct
SEQUENCE: 104
QLQLQESGPG LVKPSETLSL TCTVSGGSII TNSYYWGWIR QPPGKGLEWI GSIYYSGRTY    60
YNPSLESRVT ISVDTSKNQF SLKLTSVTAA DTAIYYCARE GDPSLDPWGQ GTLVTVSS     118

SEQ ID NO: 105          moltype = AA   length = 108
FEATURE                 Location/Qualifiers
REGION                  1..108
                        note = synthetic construct; antigen binding domain
source                  1..108
                        mol_type = protein
                        organism = synthetic construct
SEQUENCE: 105
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYGSSPWTFG QGTKVEIK                108

SEQ ID NO: 106          moltype = AA   length = 121
FEATURE                 Location/Qualifiers
REGION                  1..121
                        note = synthetic construct; antigen binding domain
source                  1..121
                        mol_type = protein
                        organism = synthetic construct
```

```
SEQUENCE: 106
EVQLVESGGD LVQPGGSLRL SCAASGFTFS TYAMNWVRQA PGKGLEWVSH ISGSGGNSYS      60
ADSVKGRFTI SRDNSKNTLY LQMNSLRAED TAIYYCSLDI MATVGGLFAY WGQGTLVTVS     120
S                                                                    121

SEQ ID NO: 107          moltype = AA   length = 131
FEATURE                 Location/Qualifiers
REGION                  1..131
                        note = synthetic construct; antigen binding domain
source                  1..131
                        mol_type = protein
                        organism = synthetic construct
SEQUENCE: 107
QVQLVESGGG VVQPGRSLRL SCVASGFIFS FYGMHWVRQA PDKGLEWVAV IWYDGSNEYY      60
ADSVKGRFTI SRDNSKNTLY LQMNSLRAED TAVYYCGRDQ GISYYDILTG NYNYYYGVDV     120
WGQGTTVTVS S                                                         131

SEQ ID NO: 108          moltype = AA   length = 119
FEATURE                 Location/Qualifiers
REGION                  1..119
                        note = synthetic construct; antigen binding domain
source                  1..119
                        mol_type = protein
                        organism = synthetic construct
SEQUENCE: 108
QVQLQQWGAG LLKPSETLSL TCAVYGGSFS GYYWNWIRQP PGKGLEWVGE ISHRGSTNYN      60
PSLKSRVTIS LDTSKNQFSL KLTSVTAADT AVYYCSRDEE LEFRFFDYWG QGTLVTVSS     119

SEQ ID NO: 109          moltype = AA   length = 107
FEATURE                 Location/Qualifiers
REGION                  1..107
                        note = synthetic construct; antigen binding domain
source                  1..107
                        mol_type = protein
                        organism = synthetic construct
SEQUENCE: 109
EIVLTQSPAT LSLSPGERAT LSCRASQSVS SYLAWYQQKP GQAPRLLVYG ASNRATGIPA      60
RFSGSGSGTD FTLTISSLEP EDFAFYYCQQ RSNWPLTFGG GTKVEIK                  107

SEQ ID NO: 110          moltype = AA   length = 124
FEATURE                 Location/Qualifiers
REGION                  1..124
                        note = synthetic construct; antigen binding domain
source                  1..124
                        mol_type = protein
                        organism = synthetic construct
SEQUENCE: 110
EVQLVESGGG LVQPGGSLRL SCVASGFTFS LYAMTWVRQV PGKGLEWVST ISGSGGGTYY      60
TDSVKGRFTI SRDNSKNTLY LQMNSLRADD TAVFYCTKES TTGTYSYFYG MDVWGQGTTV     120
TVSS                                                                 124

SEQ ID NO: 111          moltype = AA   length = 107
FEATURE                 Location/Qualifiers
REGION                  1..107
                        note = synthetic construct; antigen binding domain
source                  1..107
                        mol_type = protein
                        organism = synthetic construct
SEQUENCE: 111
DIQMTQSPSS LSASVGDRVT ITCRASQTIS SYLNWYQQKP GKAPKLLIYA ASSLQSGVPS      60
RFSGSGSGTD FTLTLSGLQP EDFATYYCQQ SYSTPLTFGG GTKVEIK                  107

SEQ ID NO: 112          moltype = AA   length = 121
FEATURE                 Location/Qualifiers
REGION                  1..121
                        note = synthetic construct; antigen binding domain
source                  1..121
                        mol_type = protein
                        organism = synthetic construct
SEQUENCE: 112
EVQLVESGGG LVQPGGSLRL SCAASGFTFS RFWMSWVRQA PGKGLEWVAN INQDGTEKYY      60
VDSVKGRFTI SRDNAKNSLY LQMNSLRAGD TAVYYCANTY YDFWSGHFDY WGQGTLVTVS     120
S                                                                    121

SEQ ID NO: 113          moltype = AA   length = 107
FEATURE                 Location/Qualifiers
REGION                  1..107
                        note = synthetic construct; antigen binding domain
```

```
source                        1..107
                              mol_type = protein
                              organism = synthetic construct
SEQUENCE: 113
DIQMTQSPST LSASVGDRVT ITCRASQSIS NWLAWYQQKP GKAPKLLIYK ASSLESGVPS    60
RFSGSGSGTE FTLTISSLQP DDFATYYCQQ YHSYSYTFGQ GTKLEIK                 107

SEQ ID NO: 114                moltype = AA  length = 121
FEATURE                       Location/Qualifiers
REGION                        1..121
                              note = synthetic construct; antigen binding domain
source                        1..121
                              mol_type = protein
                              organism = synthetic construct
SEQUENCE: 114
QEHLVESGGG VVQPGRSLRL SCEASGFTFS NFGMHWVRQA PGKGLEWVAA LWSDGSNKYY    60
ADSVKGRVTI SRDNSKNTLY LQMNSLRAED TAVYYCARGR GAPGIPIFGY WGQGTLVTVS   120
S                                                                   121

SEQ ID NO: 115                moltype = AA  length = 107
FEATURE                       Location/Qualifiers
REGION                        1..107
                              note = synthetic construct; antigen binding domain
source                        1..107
                              mol_type = protein
                              organism = synthetic construct
SEQUENCE: 115
DIQMTQSPSS LSASVGDRVT ITCRASQGIR NDLGWYQQKP GKAPKRLIYT ASSLQSGVPS    60
RFSGSGSGTE FTLTISSLQP EDFATYYCLQ HNSYPLTFGG GTKVAIK                 107

SEQ ID NO: 116                moltype = AA  length = 130
FEATURE                       Location/Qualifiers
REGION                        1..130
                              note = synthetic construct; antigen binding domain
source                        1..130
                              mol_type = protein
                              organism = synthetic construct
SEQUENCE: 116
EVQLVESGGG LVKPGGSLRL SCAASGFTFS NAWMSWVRQA PGKGLEWVGR IKRKTDGGTT    60
DYAAPVKGRF TISRDDSKNT LHLQMNSLKT EDTAVYYCTT DDIVVVPAVM REYYFGMDVW   120
GQGTTVTVSS                                                          130

SEQ ID NO: 117                moltype = AA  length = 107
FEATURE                       Location/Qualifiers
REGION                        1..107
                              note = synthetic construct; antigen binding domain
source                        1..107
                              mol_type = protein
                              organism = synthetic construct
SEQUENCE: 117
DIQMTQSPSS LSASVGDRVT ITCRTSQGIR NDLGWYQQKP GKAPKRLIYA ASSLQSGVPS    60
RFSGSGSGTE FTLTISSLQP EDFATYYCLQ HNNYPYTFGQ GTKLEIK                 107

SEQ ID NO: 118                moltype = AA  length = 121
FEATURE                       Location/Qualifiers
REGION                        1..121
                              note = synthetic construct; antigen binding domain
source                        1..121
                              mol_type = protein
                              organism = synthetic construct
SEQUENCE: 118
QVQLVQSGAE VKKPGASVQV SCKASGYSFT GYYIHWVRQA PGQGLEWMGW INPNSGTKKY    60
AHKFQGRVTM TRDTSIDTAY MILSSLISDD TAVYYCARDE DWNFGSWFDS WGQGTLVTVS   120
S                                                                   121

SEQ ID NO: 119                moltype = AA  length = 112
FEATURE                       Location/Qualifiers
REGION                        1..112
                              note = synthetic construct; antigen binding domain
source                        1..112
                              mol_type = protein
                              organism = synthetic construct
SEQUENCE: 119
DIVMTQTPLS SPVTLGQPAS ISCRSSQTLV HGDGNTYLSW IQQRPGQPPR LLIYKVSNQF    60
SGVPDRFSGS GAGTDFTLKI SRVEAEDVGL YFCMQATHFP ITFGQGTRLE IK           112
```

```
SEQ ID NO: 120          moltype = AA   length = 121
FEATURE                 Location/Qualifiers
REGION                  1..121
                        note = synthetic construct; antigen binding domain
source                  1..121
                        mol_type = protein
                        organism = synthetic construct
SEQUENCE: 120
QVHLVQSGAE VKKPGASVKV SCKASGYTFT GYYIHWVRQA PGHGLEWMGW LNPNTGTTKY      60
IQNFQGRVTM TRDTSSSTAY MELTRLRSDD TAVYYCARDE DWNYGSWFDT WGQGTLVTVS     120
S                                                                    121

SEQ ID NO: 121          moltype = AA   length = 112
FEATURE                 Location/Qualifiers
REGION                  1..112
                        note = synthetic construct; antigen binding domain
source                  1..112
                        mol_type = protein
                        organism = synthetic construct
SEQUENCE: 121
DIVMTQTPLS SPVTLGQPAS ISCRSSPSLV HSDGNTYLSW LQQRPGQPPR LLIYKISNRF      60
SGVPDRFSGS GAGTDFTLKI SRVEAEDVGV YYCMQATHFP ITFGQGTRLE IR             112

SEQ ID NO: 122          moltype = AA   length = 120
FEATURE                 Location/Qualifiers
REGION                  1..120
                        note = synthetic construct; antigen binding domain
source                  1..120
                        mol_type = protein
                        organism = synthetic construct
SEQUENCE: 122
EVQLVESGGG VVRPGGSLRL SCAASGFTFD DYGMTWVRQA PGRGLEWVSG IHWHGKRTGY      60
ADSVKGRFTI SRDNAKKSLY LQMNSLKGED TALYHCVRGG MSTGDWFDPW GQGTLVIVSS    120

SEQ ID NO: 123          moltype = AA   length = 108
FEATURE                 Location/Qualifiers
REGION                  1..108
                        note = synthetic construct; antigen binding domain
source                  1..108
                        mol_type = protein
                        organism = synthetic construct
SEQUENCE: 123
DIQMTQSPSS LSASLGDRVT ITCRASQSIN SYLNWYQQKP GKAPKLLIYY ASSLQSGVPS      60
RFSGSGSGTE FTLTISNLQP EDFATYYCQQ SYSTPPITFG QGTRLEIK                 108

SEQ ID NO: 124          moltype = AA   length = 120
FEATURE                 Location/Qualifiers
REGION                  1..120
                        note = synthetic construct; antigen binding domain
source                  1..120
                        mol_type = protein
                        organism = synthetic construct
SEQUENCE: 124
EVQLVESGGG VVRPGGSLRL SCAASGFTFD DYGMTWVRQV PGKGLEWVSG IHWSGRSTGY      60
ADSVKGRFTI SRDNAKNSLY LQMNSLRAED TALYYCARGG MSTGDWFDPW GQGTLVTVSS    120

SEQ ID NO: 125          moltype = AA   length = 108
FEATURE                 Location/Qualifiers
REGION                  1..108
                        note = synthetic construct; antigen binding domain
source                  1..108
                        mol_type = protein
                        organism = synthetic construct
SEQUENCE: 125
DIQMTQSPSS LSASVGDRVT ITCRASQSIS SYLNWYQQKP GKAPKLLIYY ASSLQSGVPS      60
RFSGSGSGTD FTLTISSLQP EDFATYYCQQ SYSTPPITFG QGTRLEIK                 108

SEQ ID NO: 126          moltype = AA   length = 115
FEATURE                 Location/Qualifiers
REGION                  1..115
                        note = synthetic construct; antigen binding domain
source                  1..115
                        mol_type = protein
                        organism = synthetic construct
SEQUENCE: 126
EVQLVESGGG LVQPGGSLRL SCAASGFTVG SNYMNWVRQA PGKGLEWVSV IYSGGSTYYA      60
DSVKGRFTIS RLTSKNTLYL QMSSLRPEDT AVYYCARGIR GLDVWGQGTT VTVSS         115
```

```
SEQ ID NO: 127          moltype = AA   length = 108
FEATURE                 Location/Qualifiers
REGION                  1..108
                        note = synthetic construct; antigen binding domain
source                  1..108
                        mol_type = protein
                        organism = synthetic construct
SEQUENCE: 127
DIQMTQSPSS LSASVGDRVT ITCRASQTIN IYLNWYQQKP GRAPRLLIYA ASSLQSGVPS   60
RFSGSGSGTD FTLTISSLQP EDFATYYCHQ SYSTPPITFG QGTRLEIK              108

SEQ ID NO: 128          moltype = AA   length = 115
FEATURE                 Location/Qualifiers
REGION                  1..115
                        note = synthetic construct; antigen binding domain
source                  1..115
                        mol_type = protein
                        organism = synthetic construct
SEQUENCE: 128
EERLVESGGD LVQPGGSLRL SCAASGITVG TNYMNWVRQA PGKGLEWVSV ISSGGNTHYA   60
DSVKGRFIMS RQTSKNTLYL QMNSLETEDT AVYYCARGIR GLDVWGQGTM VTVSS       115

SEQ ID NO: 129          moltype = AA   length = 108
FEATURE                 Location/Qualifiers
REGION                  1..108
                        note = synthetic construct; antigen binding domain
source                  1..108
                        mol_type = protein
                        organism = synthetic construct
SEQUENCE: 129
DIQMTQSPSS LSASVGDRVT ITCRASQSMS SYLNWYQQKP GRAPKLLIFA ASSLQSGVPS   60
RFSGSGSGTD FTLTISSLQP EDFATYYCQQ SYSTPPITFG QGTRLEIK              108

SEQ ID NO: 130          moltype = AA   length = 118
FEATURE                 Location/Qualifiers
REGION                  1..118
                        note = synthetic construct; antigen binding domain
source                  1..118
                        mol_type = protein
                        organism = synthetic construct
SEQUENCE: 130
QVQLVQSGAE VKMPGSSVRV SCKASGGIFS SSTISWVRQA PGQGLEWMGE IIPVFGTVNY   60
AQKFQDRVIF TADESTTTAY MELSSLKSGD TAVYFCARNW GLGSFYIWGQ GTMVTVSS    118

SEQ ID NO: 131          moltype = AA   length = 108
FEATURE                 Location/Qualifiers
REGION                  1..108
                        note = synthetic construct; antigen binding domain
source                  1..108
                        mol_type = protein
                        organism = synthetic construct
SEQUENCE: 131
EIVLTQSPGT LSLSPGERAT LSCRASQSFN FNYLAWYQQK PGQAPRLLIY GASSRATGIP   60
DRFSGSGSGT DFTLTINRLE PEDFGVFYCQ QYESAPWTFG QGTKVEIK              108

SEQ ID NO: 132          moltype = AA   length = 115
FEATURE                 Location/Qualifiers
REGION                  1..115
                        note = synthetic construct; antigen binding domain
source                  1..115
                        mol_type = protein
                        organism = synthetic construct
SEQUENCE: 132
EVQLVESGGD LVHPGRSLRL SCAASGFPFD EYAMHWVRQV PGKGLEWVSG ISWSNNNIGY   60
ADSVKGRFTI SRDNAKNSLY LQMNSLRPED TAFYYCAKSG IFDSWGQGTL VTVSS       115

SEQ ID NO: 133          moltype = AA   length = 105
FEATURE                 Location/Qualifiers
REGION                  1..105
                        note = synthetic construct; antigen binding domain
source                  1..105
                        mol_type = protein
                        organism = synthetic construct
SEQUENCE: 133
DIQMTQSPSS LSASVGDRVT ITCRASQSIS SYLNWYQQKP GKLLIYAASS LQSGVPSRFS   60
GGGSGTDFTL TISSLRPEDF ATYYCQQSYC TPPITFGQGT RLEIK                 105

SEQ ID NO: 134          moltype = AA   length = 118
FEATURE                 Location/Qualifiers
```

| | | |
|---|---|---|
| REGION | 1..118 | |
| | note = synthetic construct; antigen binding domain | |
| source | 1..118 | |
| | mol_type = protein | |
| | organism = synthetic construct | |

SEQUENCE: 134
```
EVQLVESGGG VVQPGRSLRL SCAASGFTFS SYGMHWVRQA PGKGLEWVTL ISYEGRNKYY   60
ADSVKGRFTI SRDNSKNTLY LQMNSLRAED TAVYYCAKDR TLYGMDVWGQ GTTVTVSS   118
```

| | | |
|---|---|---|
| SEQ ID NO: 135 | moltype = AA length = 121 | |
| FEATURE | Location/Qualifiers | |
| REGION | 1..121 | |
| | note = synthetic construct; antigen binding domain | |
| source | 1..121 | |
| | mol_type = protein | |
| | organism = synthetic construct | |

SEQUENCE: 135
```
QVTLRESGPA LVKTTQTLTL TCTFSGFSLS TNRMCVTWIR QPPGKALEWL ARIDWDGVKY   60
YNTSLKTRLT ISKDTSKNQV VLTMTNMDPV DTATFYCARS TSLTFYYFDY WGQGTLVTVS  120
S                                                                121
```

| | | |
|---|---|---|
| SEQ ID NO: 136 | moltype = AA length = 108 | |
| FEATURE | Location/Qualifiers | |
| REGION | 1..108 | |
| | note = synthetic construct; antigen binding domain | |
| source | 1..108 | |
| | mol_type = protein | |
| | organism = synthetic construct | |

SEQUENCE: 136
```
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ SYSTPPITFG QGTRLEIK              108
```

| | | |
|---|---|---|
| SEQ ID NO: 137 | moltype = AA length = 115 | |
| FEATURE | Location/Qualifiers | |
| REGION | 1..115 | |
| | note = synthetic construct; antigen binding domain | |
| source | 1..115 | |
| | mol_type = protein | |
| | organism = synthetic construct | |

SEQUENCE: 137
```
EVQLVESGGG LVQPGGSLRL SCAASEFTVG TNHMNWVRQA PGKGLEWVSV IYSGGNTFYA   60
DSVKGRFTIS RHTSKNTLYL QMNSLTAEDT AVYYCARGLG GMDWGQGTT VTVSS       115
```

| | | |
|---|---|---|
| SEQ ID NO: 138 | moltype = AA length = 107 | |
| FEATURE | Location/Qualifiers | |
| REGION | 1..107 | |
| | note = synthetic construct; antigen binding domain | |
| source | 1..107 | |
| | mol_type = protein | |
| | organism = synthetic construct | |

SEQUENCE: 138
```
DIQMTQSPSS LSASVGDRVT ITCRASQVIS NYLAWYQQKP GKVPRLLIYA ASTLQSGVPS   60
RFSGSGSGTD FTLTISSLQP EDVATYYCQK YNSAPRTFGQ GTKVEIK               107
```

| | | |
|---|---|---|
| SEQ ID NO: 139 | moltype = AA length = 120 | |
| FEATURE | Location/Qualifiers | |
| REGION | 1..120 | |
| | note = synthetic construct; antigen binding domain | |
| source | 1..120 | |
| | mol_type = protein | |
| | organism = synthetic construct | |

SEQUENCE: 139
```
EVQLVESGGG LVQRGESLRL YCAASGFTFS KYWMNWVRQA PGKGLEWVAN IKGDGSEKYY   60
VDSVKGRFTI SRDNAKNSLY LQMNSLRAED TAVYYCARDY WGSGYYFDFW GQGTLVTVSS  120
```

| | | |
|---|---|---|
| SEQ ID NO: 140 | moltype = AA length = 107 | |
| FEATURE | Location/Qualifiers | |
| REGION | 1..107 | |
| | note = synthetic construct; antigen binding domain | |
| source | 1..107 | |
| | mol_type = protein | |
| | organism = synthetic construct | |

SEQUENCE: 140
```
DIQMTQSPSS LSASVGDRVT ITCRASQNIN NYLNWYQQKP GKAPKLLIYA ASSFQNAVPS   60
RFSGSGSGTD FTLTISSLQP EDFATYYCQQ SYNTPLTFGG GTKVEIK               107
```

| | | |
|---|---|---|
| SEQ ID NO: 141 | moltype = AA length = 130 | |
| FEATURE | Location/Qualifiers | |

```
REGION                  1..130
                        note = synthetic construct; antigen binding domain
source                  1..130
                        mol_type = protein
                        organism = synthetic construct
SEQUENCE: 141
EVQLVESGGG LVQSGGSLRL SCAASGFTFS SYWMSWVRQA PGKGLEWVAN IKQDGSEKYY     60
VDSVKGRFTI SRDNAKNSLY LQMNSLRADD TAVYYCARDD IVVVPAPMGY YYYYFGMDVW    120
GQGTTVTVSS                                                          130

SEQ ID NO: 142          moltype = AA  length = 107
FEATURE                 Location/Qualifiers
REGION                  1..107
                        note = synthetic construct; antigen binding domain
source                  1..107
                        mol_type = protein
                        organism = synthetic construct
SEQUENCE: 142
DIQMTQSPSS LSASVGDRVT ITCRASQGIR NDLGWYQQKP GKAPKRLIYA ASSLQSGVPS     60
RFSGSGSGTE FTLTISSLQP EDFATYYCLQ HNSYPYTFGQ GTKLEIK                 107

SEQ ID NO: 143          moltype = AA  length = 123
FEATURE                 Location/Qualifiers
REGION                  1..123
                        note = synthetic construct; antigen binding domain
source                  1..123
                        mol_type = protein
                        organism = synthetic construct
SEQUENCE: 143
EVQLVESGGG LVQPGRSLRL SCAASGFTFD DFAMHWVRQA PGKGLEWVSG ISWTGGNMDY     60
ANSVKGRFTI SREDAKNSLY LQMNSLRAAD TALYYCVKDI RGIVATGGAF DIWGRGTMVT    120
VSS                                                                 123

SEQ ID NO: 144          moltype = AA  length = 107
FEATURE                 Location/Qualifiers
REGION                  1..107
                        note = synthetic construct; antigen binding domain
source                  1..107
                        mol_type = protein
                        organism = synthetic construct
SEQUENCE: 144
DIQMTQSPSS LSASVGDRVT ISCRASQTIS TYLNWFQQKP GKAPKLLIYV VSSLQSGVPS     60
RFSGSGSGTD FTLTISSLQP EDFATYYCQQ SYSTPFTFGP GTKVDIK                 107

SEQ ID NO: 145          moltype = AA  length = 115
FEATURE                 Location/Qualifiers
REGION                  1..115
                        note = synthetic construct; antigen binding domain
source                  1..115
                        mol_type = protein
                        organism = synthetic construct
SEQUENCE: 145
EVQLVESGGG LVQPGGSLRL SCAASGFTVG TNYMNWVRQA PGKGLEWISV IYSGGSTFYA     60
DSVKGRFTIS RQTSQNTLYL QMNSLRPEDT AVYYCARGIR GFDIWGQGTM VTVSS         115

SEQ ID NO: 146          moltype = AA  length = 108
FEATURE                 Location/Qualifiers
REGION                  1..108
                        note = synthetic construct; antigen binding domain
source                  1..108
                        mol_type = protein
                        organism = synthetic construct
SEQUENCE: 146
DIQMTQSPSS LSASVGDRVT ITCRASQSIS SYLNWYQQKP GKAPKLLIYA ASSLQSGVPS     60
RFSGSGSGTD FTLTISSLQP EDFATYYCQQ SYSTPPITFG QGTRLEIK                108

SEQ ID NO: 147          moltype = AA  length = 115
FEATURE                 Location/Qualifiers
REGION                  1..115
                        note = synthetic construct; antigen binding domain
source                  1..115
                        mol_type = protein
                        organism = synthetic construct
SEQUENCE: 147
EVQLVESGGG LVQPGGSLRL SCAASGFTIS TNYMNWVRQA PGKGLEWVAV IYSSGSTYYI     60
DSVKGRFTIS RLTSKNTVYL QMSSLNSEDT AVYYCARGIR GFDIWGQGTM VTVSS         115

SEQ ID NO: 148          moltype = AA  length = 124
FEATURE                 Location/Qualifiers
```

| | |
|---|---|
| REGION | 1..124 |
| | note = synthetic construct; antigen binding domain |
| source | 1..124 |
| | mol_type = protein |
| | organism = synthetic construct |

SEQUENCE: 148
```
EVQLVESGGG LVQPGRSLRL SCAASGFTID DSAMHWVRQT PGKGLEWVSG ISWKSGSIGY    60
ADSVRGRFTI SRDNAKNSLY LQMNSLRVED TALYYCVKDI RGNWNYGGNW FDPWGQGTLV   120
TVSS                                                                124
```

| | |
|---|---|
| SEQ ID NO: 149 | moltype = AA length = 115 |
| FEATURE | Location/Qualifiers |
| REGION | 1..115 |
| | note = synthetic construct; antigen binding domain |
| source | 1..115 |
| | mol_type = protein |
| | organism = synthetic construct |

SEQUENCE: 149
```
EVQLVESGGG LVQPGGSLRL SCEASGFTVG VNHMNWVRQA PGKGLEWVSV IFSSGRTFYG    60
DYVKGRLTIF RQTSQNTVYL QMNSLRSEDT AIYYCARGIG GLDIWGRGTM VTVSS        115
```

| | |
|---|---|
| SEQ ID NO: 150 | moltype = AA length = 123 |
| FEATURE | Location/Qualifiers |
| REGION | 1..123 |
| | note = synthetic construct; antigen binding domain |
| source | 1..123 |
| | mol_type = protein |
| | organism = synthetic construct |

SEQUENCE: 150
```
EVQLVESGGG LVQPGRSLRL SCAASGFTFD DYALHWVRQA PGKGLEWVSG ISWTGGTIDY    60
ADSVKGRFTI SRDNAKNSLY LQMSSLRTED TAIYYCTRDI RGNWKYGGWF DPWGQGTLVT   120
VSS                                                                 123
```

| | |
|---|---|
| SEQ ID NO: 151 | moltype = AA length = 120 |
| FEATURE | Location/Qualifiers |
| REGION | 1..120 |
| | note = synthetic construct; antigen binding domain |
| source | 1..120 |
| | mol_type = protein |
| | organism = synthetic construct |

SEQUENCE: 151
```
QVQLVQSGTE VKKPGASVKV SCKASGYTFT AYYMHWVRQA PGQGLDWMGW ISPNSGFTNY    60
AQKFQGRVTM TRDTSINTFY MELSGLRSDD TAVYYCAREG STHHNSFDPW GQGTLVTVSS   120
```

| | |
|---|---|
| SEQ ID NO: 152 | moltype = AA length = 114 |
| FEATURE | Location/Qualifiers |
| REGION | 1..114 |
| | note = synthetic construct; antigen binding domain |
| source | 1..114 |
| | mol_type = protein |
| | organism = synthetic construct |

SEQUENCE: 152
```
EVQLVESGGG LVQPGGSLRL SCAASGFTVG TNFMNWVRQA PGKGLEWVSA IYSGGTANYA    60
DSVKGRFTIS RDTSRNTLYL QMNSLRTEDT AVYYCARGGG MDVWGQGTTV TVSS         114
```

| | |
|---|---|
| SEQ ID NO: 153 | moltype = AA length = 118 |
| FEATURE | Location/Qualifiers |
| REGION | 1..118 |
| | note = synthetic construct; antigen binding domain |
| source | 1..118 |
| | mol_type = protein |
| | organism = synthetic construct |

SEQUENCE: 153
```
QVQLVQSGAE VKKPGSSVKV SCKASGGTFN TYVLSWVRQA PGQGLEWMGE IIPILGAANY    60
AQNFQGRVTF TTDESTNTAY MDLSSLRSED TAVYYCARDR TSGGFDPWGQ GTLVTVSS     118
```

| | |
|---|---|
| SEQ ID NO: 154 | moltype = AA length = 119 |
| FEATURE | Location/Qualifiers |
| REGION | 1..119 |
| | note = synthetic construct; antigen binding domain |
| source | 1..119 |
| | mol_type = protein |
| | organism = synthetic construct |

SEQUENCE: 154
```
QVQLVQSGAE VEKPGASVKV SCKASGYIFT HYGISWVRQA PGQGLEWVGW ISPYNGYTDY    60
AQKLQGRVTL TTDTSTTTAY MELRNLRSDD TAMYYCSRGR GPYWSFDLWG RGTLVTVSS   119
```

| | |
|---|---|
| SEQ ID NO: 155 | moltype = AA length = 117 |
| FEATURE | Location/Qualifiers |

```
REGION                  1..117
                        note = synthetic construct; antigen binding domain
source                  1..117
                        mol_type = protein
                        organism = synthetic construct
SEQUENCE: 155
QVQLVQSGAE VKKPGASVKV SCKASDYTFT SYGISWVRQA PGQGLEWMGW ISVYNGNINY    60
AQKFKGRVTM TTDTSTSTAY MELRSLRSDD MAVYYCARVT QFGMDVWGQG TTVTVSS     117

SEQ ID NO: 156          moltype = AA   length = 107
FEATURE                 Location/Qualifiers
REGION                  1..107
                        note = synthetic construct; antigen binding domain
source                  1..107
                        mol_type = protein
                        organism = synthetic construct
SEQUENCE: 156
DIQMTQSPSS LSASVGDRVT ITCRASQSIS SNLNWYQQNP GKAPKLLIYT TSSLQGGVPS    60
RFSGSGSGTD FTLTISSLQP EDFATYYCQQ SFRTPFTFGP GTKVDIK               107

SEQ ID NO: 157          moltype = AA   length = 128
FEATURE                 Location/Qualifiers
REGION                  1..128
                        note = synthetic construct; antigen binding domain
source                  1..128
                        mol_type = protein
                        organism = synthetic construct
SEQUENCE: 157
EVQLVESGGG LVQPGGSLKL SCAASGFTFS GSAMHWVRQA SGKGLEWVGR IRGKANSFAT    60
AYSASVKGRF TISRDDSKNT ASLQMNSLRT EDTAVYFCTR EDQQLVRPYY YHYGMDVWGQ   120
GTTVTVSS                                                           128

SEQ ID NO: 158          moltype = AA   length = 107
FEATURE                 Location/Qualifiers
REGION                  1..107
                        note = synthetic construct; antigen binding domain
source                  1..107
                        mol_type = protein
                        organism = synthetic construct
SEQUENCE: 158
DIQMTQSPSS LSASVGDRVT ITCRTSQSIT NYLNWYQQKP GKAPKLLIYA TASLQSGVPS    60
RFSGSGSETD FTLTISSLQP EDFATYYCQQ SYSTPLTFGG GTKVEIK               107

SEQ ID NO: 159          moltype = AA   length = 123
FEATURE                 Location/Qualifiers
REGION                  1..123
                        note = synthetic construct; antigen binding domain
source                  1..123
                        mol_type = protein
                        organism = synthetic construct
SEQUENCE: 159
QITLKESGPT LVKPTQTLTL TCTFSGFSLS TSGVGVGWIR QSPGRALEWL ALIYWNDHER    60
YSPSLKSRLT ITKDTSKNLV VLAMANMDPV DTATYFCAHR NIEYRRSYFF DYWGQGTLVT   120
VSS                                                                123

SEQ ID NO: 160          moltype = AA   length = 107
FEATURE                 Location/Qualifiers
REGION                  1..107
                        note = synthetic construct; antigen binding domain
source                  1..107
                        mol_type = protein
                        organism = synthetic construct
SEQUENCE: 160
DIQMTQSPSS VSASVRDRVT VTCRASQDIN NWLAWYQQKP GKAPKLLIYA ASSLQSGVPS    60
RFSGSGSGTD FTLTISSLQP EDFATYYCQQ ANTFPFTFGP GTKVDIK               107

SEQ ID NO: 161          moltype = AA   length = 118
FEATURE                 Location/Qualifiers
REGION                  1..118
                        note = synthetic construct; antigen binding domain
source                  1..118
                        mol_type = protein
                        organism = synthetic construct
SEQUENCE: 161
QVQLQESGPG LVKPSETLSL TCTVSGGSIN SYYWTWIRQP PGKGLEWIGY VYYSGSTTYN    60
PSLKSRVTIS VDTSKNQFFL NLNSVTAAET AVYYCARGTL GYYGMDVWGQ GTTVTVSS    118

SEQ ID NO: 162          moltype = AA   length = 108
FEATURE                 Location/Qualifiers
```

```
REGION                  1..108
                        note = synthetic construct; antigen binding domain
source                  1..108
                        mol_type = protein
                        organism = synthetic construct
SEQUENCE: 162
EIVLTQSPGT LSLSPGERAT LSCRASQSFS NNYLAWYQQK PGQAPRLLIY GTSIRATGIP    60
DRFSGSGSGT DFTLAISRLE PEDFAVYYCQ QYGRSPLTFG GGTKVEIK                108

SEQ ID NO: 163          moltype = AA   length = 118
FEATURE                 Location/Qualifiers
REGION                  1..118
                        note = synthetic construct; antigen binding domain
source                  1..118
                        mol_type = protein
                        organism = synthetic construct
SEQUENCE: 163
QVQLVESGGG VVQPGRSLRL SCAASGFTFS SYGMNWVRQA PGKGLEWVAV TWYDGSNKHY    60
ADSVKGRFTI SRDNSKNTLY LQMYSLRAED TAMYYCVRGG HLGAFDIWGQ GTMVTVSS    118

SEQ ID NO: 164          moltype = AA   length = 107
FEATURE                 Location/Qualifiers
REGION                  1..107
                        note = synthetic construct; antigen binding domain
source                  1..107
                        mol_type = protein
                        organism = synthetic construct
SEQUENCE: 164
EIVLTQSPGT LSLSPGERAT LSCRASQSVS SYLAWYQQKP GQAPRLLIYG ASSRATGIPD    60
RFSGGGSGTD FTLTISRLEP EDFAVYYCQQ YGSSPFTFGP GTKVDIK                107

SEQ ID NO: 165          moltype = AA   length = 121
FEATURE                 Location/Qualifiers
REGION                  1..121
                        note = synthetic construct; antigen binding domain
source                  1..121
                        mol_type = protein
                        organism = synthetic construct
SEQUENCE: 165
QVQLVQSGAE VKKPGASVKV SCKASGYTFT DYYIHWVRQA PGQGLEWMGW INPNNGVSNY    60
AQKFQGRVTM TRDTSISTAY MDLIRLRSDD TAVYYCARER ASWDYNGVDV WGQGTTVTVS  120
S                                                                  121

SEQ ID NO: 166          moltype = AA   length = 112
FEATURE                 Location/Qualifiers
REGION                  1..112
                        note = synthetic construct; antigen binding domain
source                  1..112
                        mol_type = protein
                        organism = synthetic construct
SEQUENCE: 166
DIVMTQSPLS LPVTPGEPAS ISCRSSQSLL HSNGYSYLDW YLQKPGQSPQ LLIYLGSNRA    60
SGVPDRFSGS GSGTDFTLKI SRVEAEDVGV YYCMQGLQPP NTFGQGTKLE IK          112

SEQ ID NO: 167          moltype = AA   length = 118
FEATURE                 Location/Qualifiers
REGION                  1..118
                        note = synthetic construct; antigen binding domain
source                  1..118
                        mol_type = protein
                        organism = synthetic construct
SEQUENCE: 167
QLQLQESGPG LVKPSETLSL TCIVSGGSTS SNTYYWGWIR QPPGKGLEWI GTIHYSGNPY    60
YDPSLKSRVT ISVDTSKNHF SLKLNSVTAA DTAVYYCTRQ YINFFDFWGQ GTLVTVSS   118

SEQ ID NO: 168          moltype = AA   length = 107
FEATURE                 Location/Qualifiers
REGION                  1..107
                        note = synthetic construct; antigen binding domain
source                  1..107
                        mol_type = protein
                        organism = synthetic construct
SEQUENCE: 168
EIVLTQSPAT LSLSPGERVT LSCRASQSIS RYLAWYQQKP GQAPRVLIYD ASNRATDIPA    60
RFSGSGSGTD FTLTISSLEP EDFAVYYCQQ RSNWPITFGQ GTRLEIK                107

SEQ ID NO: 169          moltype = AA   length = 121
FEATURE                 Location/Qualifiers
```

```
REGION                  1..121
                        note = synthetic construct; antigen binding domain
source                  1..121
                        mol_type = protein
                        organism = synthetic construct
SEQUENCE: 169
QVQLVESGGG VVQPGRSLRL SCAASGLTFS YYGMHWVRQA PGKGLEWVAV ISYDGSNKYY     60
ADSVKGRFTI SRDNSKNTLY LQMNSLRAED AAVYYCAKDL GGDDYYGMDV WGQGTTVTVS    120
S                                                                    121

SEQ ID NO: 170          moltype = AA  length = 108
FEATURE                 Location/Qualifiers
REGION                  1..108
                        note = synthetic construct; antigen binding domain
source                  1..108
                        mol_type = protein
                        organism = synthetic construct
SEQUENCE: 170
EIVLTQSPGT LSLSPGERAT LSCRASQSVS RTYLAWYQQK PGQAPRLLIY GAFSRATGIP     60
DRFSGSGSGT DFTLTISRLE PEDFAVYYCQ QYGSSPYTFG QGTKLEIK                 108

SEQ ID NO: 171          moltype = AA  length = 122
FEATURE                 Location/Qualifiers
REGION                  1..122
                        note = synthetic construct; antigen binding domain
source                  1..122
                        mol_type = protein
                        organism = synthetic construct
SEQUENCE: 171
QVQLVESGGG LVKPGGSLRL SCAASGFTFS DYYMTWIRQA PGKGLEWVSY ISSSGGNIFY     60
ADSVKGRFTI SRDNAKNSLY LQMNSLRGED TAVYYCARGL EPYHYYYGMD VWGQGTTVTV    120
SS                                                                   122

SEQ ID NO: 172          moltype = AA  length = 107
FEATURE                 Location/Qualifiers
REGION                  1..107
                        note = synthetic construct; antigen binding domain
source                  1..107
                        mol_type = protein
                        organism = synthetic construct
SEQUENCE: 172
DIQMTQSPSS LSASVGDRVT ITCQASQDIS NYLNWYQQKP GKAPKLLIYD ASNLETGVPS     60
RFSGSGSGTD FTFTISSLQP EDIATYFCQH YDNLPFTFGP GTKVDIK                  107

SEQ ID NO: 173          moltype = AA  length = 123
FEATURE                 Location/Qualifiers
REGION                  1..123
                        note = synthetic construct; antigen binding domain
source                  1..123
                        mol_type = protein
                        organism = synthetic construct
SEQUENCE: 173
EVQLVESGGG LVQPGGSLRL SCAASGFTLS NYVMTWVRQA PGKGLEWVSA ISGRGGNSYY     60
ADSVKGRFSI SRDHSKNTLY LQVNSLRAED TAVYYCAKAE RGYSYGFNWF DPWGQGTLVT    120
VSS                                                                  123

SEQ ID NO: 174          moltype = AA  length = 107
FEATURE                 Location/Qualifiers
REGION                  1..107
                        note = synthetic construct; antigen binding domain
source                  1..107
                        mol_type = protein
                        organism = synthetic construct
SEQUENCE: 174
DIQMTQSPSS VSASVGDRVT ITCRASQGIS SWLAWYQQKP GKAPKLLIYA ASSLQSGVPS     60
RFSGSGSGTD FTLTISSLQP EDFASYYCQQ GNNFPLTFGG GTKVEIK                  107

SEQ ID NO: 175          moltype = AA  length = 120
FEATURE                 Location/Qualifiers
REGION                  1..120
                        note = synthetic construct; antigen binding domain
source                  1..120
                        mol_type = protein
                        organism = synthetic construct
SEQUENCE: 175
QVQLVESGGG VVQPGRSLRL SCAASGFTFS TYGMHWVRQA PGKGLEWVTV IWYDGNNKYY     60
ADSVKGRFTI SRDNSKNTLY LQMNNLRAED TALYYCARGG GRLSYYHDYW GQGTLVTVSS    120

SEQ ID NO: 176          moltype = AA  length = 107
```

```
FEATURE                     Location/Qualifiers
REGION                      1..107
                            note = synthetic construct; antigen binding domain
source                      1..107
                            mol_type = protein
                            organism = synthetic construct
SEQUENCE: 176
DIQMTQSPSS LSASVGDRVT ITCRASQSIS TFLNWYQQKP GKAPNLLIYG TSSLQSGVPS    60
RFSGSGSGTD FTLTISSLQP EDFAAYYCQQ TYSTPFTFGP GTKVDIK                 107

SEQ ID NO: 177              moltype = AA   length = 119
FEATURE                     Location/Qualifiers
REGION                      1..119
                            note = synthetic construct; antigen binding domain
source                      1..119
                            mol_type = protein
                            organism = synthetic construct
SEQUENCE: 177
QVQLVQSGAE VKMSGASVRV SCKASGYTFT SYGISWMRQA PGQGLEWMGW ITAYNGNSNY    60
AQKLQGRVTM TTDTSTGTAY MELRSLTSDD TAVYYCARRG DYLGVFPYWG QGTLVTVSS    119

SEQ ID NO: 178              moltype = AA   length = 107
FEATURE                     Location/Qualifiers
REGION                      1..107
                            note = synthetic construct; antigen binding domain
source                      1..107
                            mol_type = protein
                            organism = synthetic construct
SEQUENCE: 178
DIQMTQSPSS LSASVGDRVT ITCRASQSIS SYLNWYQQKP GKAPNLLIYT ASSLQSGVPS    60
RFSGSGSGTD FTLTISSLQP EDFATYYCQQ SYSSPLTFGG GTKVEIK                 107

SEQ ID NO: 179              moltype = AA   length = 116
FEATURE                     Location/Qualifiers
REGION                      1..116
                            note = synthetic construct; antigen binding domain
source                      1..116
                            mol_type = protein
                            organism = synthetic construct
SEQUENCE: 179
EVQLVESGGG LVQPGGSLRL SCAASGFTFS NYEMSWVRQA PGKGLEWVSS IRTSGTTKYY    60
ADSMKGRFTI SRDNAKNSLY LQMNSLRAED TAVYYCAGGG TFLHYWGQGT LVTVSS       116

SEQ ID NO: 180              moltype = AA   length = 108
FEATURE                     Location/Qualifiers
REGION                      1..108
                            note = synthetic construct; antigen binding domain
source                      1..108
                            mol_type = protein
                            organism = synthetic construct
SEQUENCE: 180
DIQMTQSPSS VSASVGDRVT ITCRASQGIA SYLAWYQQKP GKAPKLLIYA ASSLQTGVPS    60
RFSGSGYGTD FTLTISSLQP EDFATYYCQQ AKSFPMYTFG QGTKLEIK                108

SEQ ID NO: 181              moltype = AA   length = 122
FEATURE                     Location/Qualifiers
REGION                      1..122
                            note = synthetic construct; antigen binding domain
source                      1..122
                            mol_type = protein
                            organism = synthetic construct
SEQUENCE: 181
QVQLQESGPG LVKPSQTLSL TCTVSGGSIT SGGYYWSWIR QHPGKGLEWI GYIFYSGITN    60
YNPSLKSRVT ISVDTSKNQF SLKLTSVTAA DTAVYYCATY NSLRLYYGMD VWGQGTTVTV   120
SS                                                                  122

SEQ ID NO: 182              moltype = AA   length = 112
FEATURE                     Location/Qualifiers
REGION                      1..112
                            note = synthetic construct; antigen binding domain
source                      1..112
                            mol_type = protein
                            organism = synthetic construct
SEQUENCE: 182
DVVMTQSPLS LPVILGQPAS ISCRSSQSLV YGDGNTYLNW FQQRPGQSPR RLIYKVSNRD    60
SGVPDRFSGS GSGTDFTLKI SRVEAEDVGV YYCMQSTHWP LTFGGGTKVE IK           112

SEQ ID NO: 183              moltype = AA   length = 120
FEATURE                     Location/Qualifiers
```

```
REGION                  1..120
                        note = synthetic construct; antigen binding domain
source                  1..120
                        mol_type = protein
                        organism = synthetic construct
SEQUENCE: 183
EVQLVESGGG LVQPGGSLRL ACAASGFTFS DYYMDWVRQV PGKGLEWVGR SRDKANSFTT    60
EYVASVKGRF TISREDSKNS VYLQMNSLKT EDTAVYYCAR TNYDFSLDVW GQGTTVTVSS   120

SEQ ID NO: 184          moltype = AA   length = 107
FEATURE                 Location/Qualifiers
REGION                  1..107
                        note = synthetic construct; antigen binding domain
source                  1..107
                        mol_type = protein
                        organism = synthetic construct
SEQUENCE: 184
DIQMTQSPSS LSASVGDRVT ITCRASQDIN NYLAWFQQKP GNAPKSLIYA ASSLQSGVPS    60
KFSGSGSGTD FTLTISSLQP EDFATYYCQQ YSTYPITFGQ GTRLEIK                107

SEQ ID NO: 185          moltype = AA   length = 118
FEATURE                 Location/Qualifiers
REGION                  1..118
                        note = synthetic construct; antigen binding domain
source                  1..118
                        mol_type = protein
                        organism = synthetic construct
SEQUENCE: 185
QVQLQESGPG LVKPSETLSL TCTVSGGSIS SYHWSWIRQP LGKGLEWIGY IYYSGSTNYN    60
PSLKSRVTIS VDTSKNQFSL KLSSVTAADT AVYYCARGGS SIWPFDYWGQ GTLVTVSS    118

SEQ ID NO: 186          moltype = AA   length = 107
FEATURE                 Location/Qualifiers
REGION                  1..107
                        note = synthetic construct; antigen binding domain
source                  1..107
                        mol_type = protein
                        organism = synthetic construct
SEQUENCE: 186
DIQMTQSPST LSASVGDRVT ITCRASQSIS SWLAWYQQKS GKAPKLLISK ASTLESGVPS    60
RFSGSGSGTE FTLTISSLQP DDFATYYCQQ YNIYSWTFGQ GTKVEIK                107

SEQ ID NO: 187          moltype = AA   length = 120
FEATURE                 Location/Qualifiers
REGION                  1..120
                        note = synthetic construct; antigen binding domain
source                  1..120
                        mol_type = protein
                        organism = synthetic construct
SEQUENCE: 187
QITLKESGPT LVKPTQTLTL TCTFSGFSLS TSGVGVGWIR QPPGVALEWL ALIYWNDDKR    60
FSPSLKSRLT ITKDTSKNQV VLTMTNMDPV DTATYYCAHR RLGLYYFDYW GQGTLVTVSS  120

SEQ ID NO: 188          moltype = AA   length = 107
FEATURE                 Location/Qualifiers
REGION                  1..107
                        note = synthetic construct; antigen binding domain
source                  1..107
                        mol_type = protein
                        organism = synthetic construct
SEQUENCE: 188
DIQLTQSPSF LSASVGDRVT ITCWASQGIS SYLAWYQQKP GKAPKLLIYA ASTLQSGVPS    60
RFSGSGSGTE FTLTISSLQP EDFATYYCQQ VHIYPFTFGP GTKVDIK                107

SEQ ID NO: 189          moltype = AA   length = 122
FEATURE                 Location/Qualifiers
REGION                  1..122
                        note = synthetic construct; antigen binding domain
source                  1..122
                        mol_type = protein
                        organism = synthetic construct
SEQUENCE: 189
QVQLVQSGAE VKKPGASVKV SCKASGYTLS SYGISWVRQA PGQGLEWMGW ISAYNGNTNY    60
AQKLQGRLTM TTDTSTSTAY MELRSLRSDD TAVYYCSRDG PFKISFFGMD VWGQGTTVTV  120
SS                                                                 122

SEQ ID NO: 190          moltype = AA   length = 108
FEATURE                 Location/Qualifiers
```

```
REGION                       1..108
                             note = synthetic construct; antigen binding domain
source                       1..108
                             mol_type = protein
                             organism = synthetic construct
SEQUENCE: 190
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ SYSTPPITFG QGTRLEIK               108

SEQ ID NO: 191               moltype = AA   length = 118
FEATURE                      Location/Qualifiers
REGION                       1..118
                             note = synthetic construct; antigen binding domain
source                       1..118
                             mol_type = protein
                             organism = synthetic construct
SEQUENCE: 191
QVQLVESGGG EVQPGRSLRL SCAASGFTFS SYGMHWVRQA PGKGLEWVAV IWYDGRNKHY   60
VDSVKGRFTI SRDNSKNTVY LQMNSLRAED SAVYYCVRGG QLGAFDYWGQ GTLVTVSS   118

SEQ ID NO: 192               moltype = AA   length = 108
FEATURE                      Location/Qualifiers
REGION                       1..108
                             note = synthetic construct; antigen binding domain
source                       1..108
                             mol_type = protein
                             organism = synthetic construct
SEQUENCE: 192
EIVLTQSPGT LSLSPGERAT LSCRASQSVS SSYLAWYQQK PGQAPRLLIY GASSRATGIP   60
DRFSGSGSGT DFTLTISRLE PEDFAVYYCQ QYGSSPWTFG QGTKVEIK               108

SEQ ID NO: 193               moltype = AA   length = 118
FEATURE                      Location/Qualifiers
REGION                       1..118
                             note = synthetic construct; antigen binding domain
source                       1..118
                             mol_type = protein
                             organism = synthetic construct
SEQUENCE: 193
QVQLVESGGG VVQPGRSLRL SCAASGFTSS SYGIHWVRQA PGKGLEWVAV IWYDGSNKYY   60
ADSVKGRFTI SRDNSKNTLY LQMNSLRAED TAVYYCARGG PWGAFDIWGQ GTMVTVSS   118

SEQ ID NO: 194               moltype = AA   length = 108
FEATURE                      Location/Qualifiers
REGION                       1..108
                             note = synthetic construct; antigen binding domain
source                       1..108
                             mol_type = protein
                             organism = synthetic construct
SEQUENCE: 194
DIRMTQSPSS LSASVGDRVT ITCRASQTVN TFLNWYQQKP GKAPKLLIFG ASSLQSGVPS   60
RFSGSGSGTD FTLTISGLQP EDFAIYYCQQ SYSVPPITFG QGTRLEIE               108

SEQ ID NO: 195               moltype = AA   length = 122
FEATURE                      Location/Qualifiers
REGION                       1..122
                             note = synthetic construct; antigen binding domain
source                       1..122
                             mol_type = protein
                             organism = synthetic construct
SEQUENCE: 195
QVQLHESGPG LVKPSQTLSL TCSVSGGSIS NGGYYWSWIR QHPGQGLEWI GYIYYIGNTY   60
YNPSLESRVT MSIDTSKNQF SLKLSSVTAA DTAIYYCARQ EFVPGAEYFL HWGQGILVTV  120
SS                                                                122

SEQ ID NO: 196               moltype = AA   length = 107
FEATURE                      Location/Qualifiers
REGION                       1..107
                             note = synthetic construct; antigen binding domain
source                       1..107
                             mol_type = protein
                             organism = synthetic construct
SEQUENCE: 196
DIQMTQSPSS LSASVGDRVT ITCRASQDIR NDLGWHQQKS GKAPKSLIYA ASSLQSGAPS   60
RFSGSGSGTE FTLTISSLQP EDSATYYCLQ QNSYPPTFGQ GTKVEIK                107

SEQ ID NO: 197               moltype = AA   length = 122
FEATURE                      Location/Qualifiers
```

```
REGION                  1..122
                        note = synthetic construct; antigen binding domain
source                  1..122
                        mol_type = protein
                        organism = synthetic construct
SEQUENCE: 197
EVQLVESGGG LVQPGRSLRL SCAGTGFIFD DYAMHWVRQA PGKGLEWVSG ISWNSNSLGY    60
ADSVKGRFTI SRDNAKKSLY LQMSSLRAED TALYYCVKDV TRLELRGFLD YWGQGTQVTV   120
SS                                                                  122

SEQ ID NO: 198          moltype = AA  length = 108
FEATURE                 Location/Qualifiers
REGION                  1..108
                        note = synthetic construct; antigen binding domain
source                  1..108
                        mol_type = protein
                        organism = synthetic construct
SEQUENCE: 198
EIVLTQSPDT LSLSPGERAT LSCRASQSVS SSFLAWYQQK PGQAPRLLIY GASSRATGIP    60
DRFSGSGSGT DFTLTISRLE PEDFAVYYCQ QYGRSPWTFG QGTKVAIK                108

SEQ ID NO: 199          moltype = AA  length = 118
FEATURE                 Location/Qualifiers
REGION                  1..118
                        note = synthetic construct; antigen binding domain
source                  1..118
                        mol_type = protein
                        organism = synthetic construct
SEQUENCE: 199
DRQMVESGGG VVQPGRSLRL SCIASGFIIS RYGMHWVRQA PGKGLEWVAV IWYDGRNKNY    60
ADSVKGRFTI SRDNSKNTLY LEMNSLRAED TAVYYCGRVH QFGAFDIWGQ GTMVTVSS    118

SEQ ID NO: 200          moltype = AA  length = 108
FEATURE                 Location/Qualifiers
REGION                  1..108
                        note = synthetic construct; antigen binding domain
source                  1..108
                        mol_type = protein
                        organism = synthetic construct
SEQUENCE: 200
DIQMTQSPSS LSASVGDRIT ITCRGSQNIG SFLSWYQQRP GKAPKLLIFG AYNLQGGVPS    60
RFSGSGSGTD FTLTISSLQP EDFATYFCQQ SYSTPPITFG QGTRLEIK                108

SEQ ID NO: 201          moltype = AA  length = 121
FEATURE                 Location/Qualifiers
REGION                  1..121
                        note = synthetic construct; antigen binding domain
source                  1..121
                        mol_type = protein
                        organism = synthetic construct
SEQUENCE: 201
QVQLQESGPG LVKPSQTLSL TCTVSGGSIN NGGHYWTWIR QHPGKGLEWI GYIYYIGTTY    60
YNPSLESRLS LSVDTSKNQF SLKLSSVTAA DTAIYYCARS SLSVSEAFDV WGQGTMVTVS   120
S                                                                   121

SEQ ID NO: 202          moltype = AA  length = 108
FEATURE                 Location/Qualifiers
REGION                  1..108
                        note = synthetic construct; antigen binding domain
source                  1..108
                        mol_type = protein
                        organism = synthetic construct
SEQUENCE: 202
DIQMTQSPSS LSASVGDRFT ITCRASQSIG SFLSWYQQKP GKAPKLLIYA ASSLQSGVPS    60
RFSGSGSGTD FTLTISSLQP EDFATYYCQQ SYNTPPITFG QGTRLEIK                108

SEQ ID NO: 203          moltype = AA  length = 121
FEATURE                 Location/Qualifiers
REGION                  1..121
                        note = synthetic construct; antigen binding domain
source                  1..121
                        mol_type = protein
                        organism = synthetic construct
SEQUENCE: 203
QVQLQESGPG LVRPSQTLSL TCTVSGGSIS NGGYYWTWIR QNPGKGLEWI GYIYYIGTTY    60
YNPSLESRLS LSVDTSKNQF SLKLTSVTAA DTAVYYCARS SLAVSEAFDI WGQGTMVTVS   120
S                                                                   121

SEQ ID NO: 204          moltype = AA  length = 108
```

```
FEATURE                 Location/Qualifiers
REGION                  1..108
                        note = synthetic construct; antigen binding domain
source                  1..108
                        mol_type = protein
                        organism = synthetic construct
SEQUENCE: 204
DIQLTQSPSS LSASVGDRVT ITCRASQTIS TYLNWYQQKP GNAPKLLIYA ASSLQSGVPS    60
RFSGRGSGTD FTLTISSLQP EDFATYYCQQ GYTTPPITFG QGTRLEIK                108

SEQ ID NO: 205          moltype = AA  length = 121
FEATURE                 Location/Qualifiers
REGION                  1..121
                        note = synthetic construct; antigen binding domain
source                  1..121
                        mol_type = protein
                        organism = synthetic construct
SEQUENCE: 205
QVQLVQSGTE VKRPGASVKV SCKASGFTFT GYYIYWVRQA PGEGLEWMGW INPHSGGTKY    60
AQKFQGRVTL TRDTSINTAY LDLISLRSDD TAVYYCARIG GGGYSSYFDY WGQGTLVTVS   120
S                                                                  121

SEQ ID NO: 206          moltype = AA  length = 107
FEATURE                 Location/Qualifiers
REGION                  1..107
                        note = synthetic construct; antigen binding domain
source                  1..107
                        mol_type = protein
                        organism = synthetic construct
SEQUENCE: 206
DIQMTQSPSS VSASVGDRVT ITCRASQDIS SWLAWYQQKP GKAPKLLIYT TANLQSGVPS    60
RFSGSGSGTD FTLTISSLQS EDFATYYCQQ ANSFPFTFGS GTKVDIK                 107

SEQ ID NO: 207          moltype = AA  length = 121
FEATURE                 Location/Qualifiers
REGION                  1..121
                        note = synthetic construct; antigen binding domain
source                  1..121
                        mol_type = protein
                        organism = synthetic construct
SEQUENCE: 207
EVQLLESGGG LVQPGGSLRL SCAASGFTFS SYAMSWVRQA PGKGLEWVSD ISGSGLSTYY    60
ADSVKGRFAI SRDNSKNMLY LQMNRLRAED TAVYYCAKEP SHWNGEAFDI WGQGTMVTVS   120
S                                                                  121

SEQ ID NO: 208          moltype = AA  length = 108
FEATURE                 Location/Qualifiers
REGION                  1..108
                        note = synthetic construct; antigen binding domain
source                  1..108
                        mol_type = protein
                        organism = synthetic construct
SEQUENCE: 208
EIVLTQSPDT LSLSPGERAT LSCRASQTVS NSHLAWYQQK PGQAPRLLIY GTSSRATGIP    60
DRFSGSGSGT DFSLTIIRLE PDDFAVYFCQ QHESSPPTFG QGAKLEIK                108

SEQ ID NO: 209          moltype = AA  length = 122
FEATURE                 Location/Qualifiers
REGION                  1..122
                        note = synthetic construct; antigen binding domain
source                  1..122
                        mol_type = protein
                        organism = synthetic construct
SEQUENCE: 209
QLQLQESGPG LVKPSETLSF TCTVSGGSIS SNYYYWGWVR QSPGKGLEWI GSIYHTGNAY    60
DNPSLKSRVT ISVDTSKNQF SLNLNSVTAA DTAIYYCARH HSSSSWWYFD VWGRGTLVIV   120
SS                                                                 122

SEQ ID NO: 210          moltype = AA  length = 108
FEATURE                 Location/Qualifiers
REGION                  1..108
                        note = synthetic construct; antigen binding domain
source                  1..108
                        mol_type = protein
                        organism = synthetic construct
SEQUENCE: 210
EIVLTQSPGT LSLSPGERAT LSCRASQWIS SSYLAWYQQK PGQAPRLLIY GAFSRAPGIP    60
GRFSGSGSGT DFTLTISRLE PEDFAVYYCQ QYGSSPYTFG QGTKLEIN                108
```

```
SEQ ID NO: 211            moltype = AA  length = 121
FEATURE                   Location/Qualifiers
REGION                    1..121
                          note = synthetic construct; antigen binding domain
source                    1..121
                          mol_type = protein
                          organism = synthetic construct
SEQUENCE: 211
QVQLVESGGG VVQPGRSLRL SCAASGITFS SYGMHWVRQA PGKGLEWVAL TSYDGSKKYY   60
SDSVKGRFTI SRDNSKNTLY LQMNSLRPED TAVYYCAKDK GGDDYYGMDV WGQGTTVTVS  120
S                                                                 121

SEQ ID NO: 212            moltype = AA  length = 108
FEATURE                   Location/Qualifiers
REGION                    1..108
                          note = synthetic construct; antigen binding domain
source                    1..108
                          mol_type = protein
                          organism = synthetic construct
SEQUENCE: 212
DIQMTQSPSS LSASVGDRVT ITCRASQSIS TYLNWYQQKP GKAPKLLIYA ASTLQSGVPS   60
RFGGSGSGTD FTLTVSSLQP EDFATYYCQQ SYSTPPITFG QGTRLEIN              108

SEQ ID NO: 213            moltype = AA  length = 122
FEATURE                   Location/Qualifiers
REGION                    1..122
                          note = synthetic construct; antigen binding domain
source                    1..122
                          mol_type = protein
                          organism = synthetic construct
SEQUENCE: 213
QVQLVQSGAE VKKPGASVKV SCKTSGYTFT NNGISWVRQV PGQGLEWMGW ISPYNGNTKY   60
AQKFQGRVTM TTDTSTTTVY MDVRSLRSDD TAVYFCARDG PITISYFGMD VWGQGTTVTV  120
SS                                                                122

SEQ ID NO: 214            moltype = AA  length = 108
FEATURE                   Location/Qualifiers
REGION                    1..108
                          note = synthetic construct; antigen binding domain
source                    1..108
                          mol_type = protein
                          organism = synthetic construct
SEQUENCE: 214
EIVLTQSPDT LSLSPGERAT LSCRASQSVA GSYLAWYQQK PGQAPRLLIY GASSRATGIP   60
DRFSGSGSGT DFTLTISRLE PEDFAVYYCQ QYGTSPWTFG QGTKVEIT              108

SEQ ID NO: 215            moltype = AA  length = 118
FEATURE                   Location/Qualifiers
REGION                    1..118
                          note = synthetic construct; antigen binding domain
source                    1..118
                          mol_type = protein
                          organism = synthetic construct
SEQUENCE: 215
QVQLVESGGG VVQPGRSLRL SCAASGFTVN RYGIHWVRQA PGKGLEWVAV TWYDGRNKYF   60
ADSVKGRFSF SRDSSTNTLY LQMNSLRAED TAVYYCARGG LFGYFDYWGQ GTLVTVSS   118

SEQ ID NO: 216            moltype = AA  length = 107
FEATURE                   Location/Qualifiers
REGION                    1..107
                          note = synthetic construct; antigen binding domain
source                    1..107
                          mol_type = protein
                          organism = synthetic construct
SEQUENCE: 216
EIVLTQSPGT LSLSPGERAT LSCRASQSVS SYLAWYQQKP GQAPRLLIYG ASSRATGIPD   60
RFSGSGSGTD FILTINRLEP EDFAVYYCQH YGNSPWTFGQ GTKVEIK               107

SEQ ID NO: 217            moltype = AA  length = 118
FEATURE                   Location/Qualifiers
REGION                    1..118
                          note = synthetic construct; antigen binding domain
source                    1..118
                          mol_type = protein
                          organism = synthetic construct
SEQUENCE: 217
QVQLVESGGG VVQPGRSLRL SCAASGFTFS SYGIHWVRQA PGKGLEWVAV IWYGGNNKYY   60
ADSVKGRFTI SRDNSKNTLY LQMNSLRAED TALYHCARSG NFGAFDIWGQ GTMVTVSS   118
```